United States Patent
Capra et al.

(10) Patent No.: US 9,610,185 B2
(45) Date of Patent: Apr. 4, 2017

(54) SYSTEMS, METHODS, AND DEVICES FOR AUTOMATIC CLOSURE OF MEDICAL DEVICES

(71) Applicant: Boa Technology, Inc., Denver, CO (US)

(72) Inventors: James Capra, Steamboat Springs, CO (US); Ilya Minkin, Denver, CO (US); Rebecca Peterson, Denver, CO (US); Mark Soderberg, Conifer, CO (US); Aaron Venturini, Denver, CO (US); Brett Vladika, Golden, CO (US); Daniel Hipwood, Denver, CO (US)

(73) Assignee: Boa Technology Inc., Denver, CO (US)

( * ) Notice: Subject to any disclaimer, the term of this patent is extended or adjusted under 35 U.S.C. 154(b) by 379 days.

(21) Appl. No.: 14/198,419

(22) Filed: Mar. 5, 2014

(65) Prior Publication Data

US 2014/0257156 A1    Sep. 11, 2014

Related U.S. Application Data

(60) Provisional application No. 61/772,935, filed on Mar. 5, 2013.

(51) Int. Cl.
*A61F 5/00*    (2006.01)
*A61F 5/01*    (2006.01)
(Continued)

(52) U.S. Cl.
CPC .......... *A61F 5/0102* (2013.01); *A43B 3/0005* (2013.01); *A43B 11/00* (2013.01); *A43C 11/165* (2013.01)

(58) Field of Classification Search
CPC ..... A43B 11/00; A43B 3/0005; A43C 11/008; A43C 11/165; A61F 5/01; A61F 5/028;
(Continued)

(56) References Cited

U.S. PATENT DOCUMENTS

| 59,332 A | 10/1866 | White et al. |
| 80,834 A | 8/1868 | Prussia |

(Continued)

FOREIGN PATENT DOCUMENTS

| CA | 2112789 | 8/1994 |
| CA | 2114387 | 8/1994 |

(Continued)

OTHER PUBLICATIONS

International Search Report and Written Opinion for International Patent Application No. PCT/US2014/020894 filed Mar. 5, 2014, 12 pages.

(Continued)

*Primary Examiner* — Michael Brown
(74) *Attorney, Agent, or Firm* — Kilpatrick Townsend & Stockton LLP

(57) ABSTRACT

According to an embodiment, a brace may include a motorized tensioning device, a tensioning member operationally coupled with the motorized tensioning device to tighten the brace about the limb, and a control unit communicatively coupled with the motorized tensioning device to control adjustment of a tension of the tensioning member. A method for providing therapy with the brace fitted about a limb may include communicating a first instruction from the control unit to the motorized tensioning device to adjust the tension of the tensioning member according to a therapeutic regimen that is designed to aid in recovery of the limb via repetitive movement of the limb.

25 Claims, 48 Drawing Sheets

(51) Int. Cl.
*A43B 3/00* (2006.01)
*A43B 11/00* (2006.01)
*A43C 11/16* (2006.01)

(58) Field of Classification Search
CPC ...... A61F 5/0101; A61F 5/0102; A61F 5/024; A61F 2002/5003; A61F 2/38; A61F 2/3859; A61F 2/389; A61F 2002/2835; A61F 2002/30398; A61F 2002/30934; A61F 2002/4635; A61F 2002/5007; A61F 2002/5018; A61F 2002/503; B65H 59/382; A41D 13/0531; A61B 2562/0219; A61B 2562/028; A61B 5/02042; A61B 5/02055; A61B 5/11; A61B 5/6803; A61B 5/6804; A61B 5/6805; A61B 5/68
USPC ........................................ 602/26, 27, 32–36
See application file for complete search history.

(56) References Cited

U.S. PATENT DOCUMENTS

| | | |
|---|---|---|
| 117,530 A | 8/1871 | Foote |
| 228,946 A | 6/1880 | Schulz |
| 230,759 A | 8/1880 | Drummond |
| 379,113 A | 3/1888 | Hibberd |
| 746,563 A | 12/1903 | McMahon |
| 819,993 A | 5/1906 | Haws et al. |
| 908,704 A | 1/1909 | Sprinkle |
| 1,060,422 A | 4/1913 | Bowdish |
| 1,062,511 A | 5/1913 | Short |
| 1,083,775 A | 1/1914 | Thomas |
| 1,090,438 A | 3/1914 | Worth et al. |
| 1,170,472 A | 2/1916 | Barber |
| 1,288,859 A | 12/1918 | Feller et al. |
| 1,390,991 A | 9/1921 | Fotchuk |
| 1,393,188 A | 10/1921 | Whiteman |
| 1,469,661 A | 2/1922 | Migita |
| 1,412,486 A | 4/1922 | Paine |
| 1,416,203 A | 5/1922 | Hobson |
| 1,429,657 A | 9/1922 | Trawinski |
| 1,481,903 A | 4/1923 | Hart |
| 1,466,673 A | 9/1923 | Solomon et al. |
| 1,530,713 A | 2/1924 | Clark |
| 1,502,919 A | 7/1924 | Seib |
| 1,862,047 A | 6/1932 | Boulet et al. |
| 1,995,243 A | 6/1934 | Clarke |
| 2,088,851 A | 8/1937 | Gantenbein |
| 2,109,751 A | 3/1938 | Matthias et al. |
| 2,124,310 A | 9/1938 | Murr, Jr. |
| 2,316,102 A | 4/1943 | Preston |
| 2,539,026 A | 1/1951 | Mangold |
| 2,611,940 A | 9/1952 | Cairns |
| 2,673,381 A | 3/1954 | Dueker |
| 2,907,086 A | 10/1959 | Ord |
| 2,991,523 A | 7/1961 | Del Conte |
| 3,028,602 A | 4/1962 | Miller |
| 3,035,319 A | 5/1962 | Wolff |
| 3,106,003 A | 10/1963 | Herdman |
| 3,112,545 A | 12/1963 | Williams |
| 3,122,810 A | 3/1964 | Lawrence et al. |
| 3,163,900 A | 1/1965 | Martin |
| D200,394 S | 2/1965 | Hakim |
| 3,169,325 A | 2/1965 | Fesl |
| 3,193,950 A | 7/1965 | Shu-Lien Liou |
| 3,197,155 A | 7/1965 | Chow |
| 3,221,384 A | 12/1965 | Aufenacker |
| 3,276,090 A | 10/1966 | Nigon |
| D206,146 S | 11/1966 | Hendershot |
| 3,345,707 A | 10/1967 | Rita |
| D210,649 S | 4/1968 | Getgay |
| 3,401,437 A | 9/1968 | Christpohersen |
| 3,430,303 A | 3/1969 | Perrin et al. |
| 3,491,465 A | 1/1970 | Martin |
| 3,545,106 A | 12/1970 | Martin |
| 3,618,232 A | 11/1971 | Shnuriwsky |
| 3,668,791 A | 6/1972 | Salzman et al. |
| 3,678,539 A | 7/1972 | Graup |
| 3,703,775 A | 11/1972 | Gatti |
| 3,729,779 A | 5/1973 | Porth |
| 3,738,027 A | 6/1973 | Schoch |
| 3,793,749 A | 2/1974 | Gertsch et al. |
| 3,808,644 A | 5/1974 | Schoch |
| 3,934,346 A | 1/1976 | Sasaki et al. |
| 3,975,838 A | 8/1976 | Martin |
| 4,084,267 A | 4/1978 | Zadina |
| 4,130,949 A | 12/1978 | Seidel |
| 4,142,307 A | 3/1979 | Martin |
| 4,227,322 A | 10/1980 | Annovi |
| 4,261,081 A | 4/1981 | Lott |
| 4,267,622 A | 5/1981 | Burnett-Johnston |
| 4,408,403 A | 10/1983 | Martin |
| 4,417,703 A | 11/1983 | Weinhold |
| 4,433,456 A | 2/1984 | Baggio |
| 4,463,761 A | 8/1984 | Pols et al. |
| 4,480,395 A | 11/1984 | Schoch |
| 4,507,878 A | 4/1985 | Semouha |
| 4,516,576 A | 5/1985 | Kirchner |
| 4,551,932 A | 11/1985 | Schoch |
| 4,555,830 A | 12/1985 | Petrini et al. |
| 4,574,500 A | 3/1986 | Aldinio et al. |
| 4,616,432 A | 10/1986 | Bunch et al. |
| 4,616,524 A | 10/1986 | Bidoia |
| 4,619,057 A | 10/1986 | Sartor et al. |
| 4,620,378 A | 11/1986 | Sartor |
| 4,631,839 A | 12/1986 | Bonetti et al. |
| 4,631,840 A | 12/1986 | Gamm |
| 4,633,599 A | 1/1987 | Morell et al. |
| 4,644,938 A | 2/1987 | Yates et al. |
| 4,654,985 A | 4/1987 | Chalmers |
| 4,660,300 A | 4/1987 | Morell et al. |
| 4,660,302 A | 4/1987 | Arieh et al. |
| 4,680,878 A | 7/1987 | Pozzobon et al. |
| 4,719,670 A | 1/1988 | Kurt |
| 4,719,709 A | 1/1988 | Vaccari |
| 4,719,710 A | 1/1988 | Pozzobon |
| 4,722,477 A | 2/1988 | Floyd |
| 4,741,115 A | 5/1988 | Pozzobon |
| 4,748,726 A | 6/1988 | Schoch |
| 4,760,653 A | 8/1988 | Baggio |
| 4,780,969 A | 11/1988 | White, Jr. |
| 4,787,124 A | 11/1988 | Pozzobon et al. |
| 4,790,081 A | 12/1988 | Benoit et al. |
| 4,796,829 A | 1/1989 | Pozzobon et al. |
| 4,799,297 A | 1/1989 | Baggio et al. |
| 4,802,291 A | 2/1989 | Sartor |
| 4,811,503 A | 3/1989 | Iwama |
| 4,826,098 A | 5/1989 | Pozzobon et al. |
| 4,841,649 A | 6/1989 | Baggio et al. |
| 4,856,207 A | 8/1989 | Datson |
| 4,862,878 A | 9/1989 | Davison |
| 4,870,723 A | 10/1989 | Pozzobon et al. |
| 4,870,761 A | 10/1989 | Tracy |
| 4,884,760 A | 12/1989 | Baggio et al. |
| 4,901,938 A | 2/1990 | Cantley et al. |
| 4,924,605 A | 5/1990 | Spademan |
| D308,282 S | 6/1990 | Bergman et al. |
| 4,937,953 A | 7/1990 | Walkhoff |
| 4,961,544 A | 10/1990 | Bidoia |
| 4,979,953 A | 12/1990 | Spence |
| 4,989,805 A | 2/1991 | Burke |
| 5,001,817 A | 3/1991 | De Bortoli et al. |
| 5,016,327 A | 5/1991 | Klausner |
| 5,042,177 A | 8/1991 | Schoch |
| 5,062,225 A | 11/1991 | Gorza |
| 5,065,480 A | 11/1991 | DeBortoli |
| 5,065,481 A | 11/1991 | Walkhoff |
| 5,108,216 A | 4/1992 | Geyer et al. |
| 5,117,567 A | 6/1992 | Berger |
| 5,152,038 A | 10/1992 | Schoch |
| 5,157,813 A | 10/1992 | Carroll |
| 5,158,428 A | 10/1992 | Gessner et al. |
| 5,177,882 A | 1/1993 | Berger |
| 5,181,331 A | 1/1993 | Berger |

(56) References Cited

U.S. PATENT DOCUMENTS

| | | |
|---|---|---|
| 5,184,378 A | 2/1993 | Batra |
| D333,552 S | 3/1993 | Berger et al. |
| 5,205,055 A | 4/1993 | Harrell |
| 5,233,767 A | 8/1993 | Kramer |
| 5,249,377 A | 10/1993 | Walkhoff |
| 5,259,094 A | 11/1993 | Zepeda |
| 5,315,741 A | 5/1994 | Dubberke |
| 5,319,868 A | 6/1994 | Hallenbeck |
| 5,319,869 A | 6/1994 | McDonald et al. |
| 5,325,613 A | 7/1994 | Sussmann |
| 5,327,662 A | 7/1994 | Hallenbeck |
| 5,335,401 A | 8/1994 | Hanson |
| 5,341,583 A | 8/1994 | Hallenbeck |
| 5,345,697 A | 9/1994 | Quellais |
| 5,355,596 A | 10/1994 | Sussmann |
| 5,357,654 A | 10/1994 | Hsing-Chi |
| 5,371,957 A | 12/1994 | Gaudio |
| 5,381,609 A | 1/1995 | Hieblinger |
| 5,392,535 A | 2/1995 | Van Noy et al. |
| D357,576 S | 4/1995 | Steinweis |
| 5,425,161 A | 6/1995 | Schoch |
| 5,425,185 A | 6/1995 | Gansler |
| 5,430,960 A | 7/1995 | Richardson |
| 5,433,648 A | 7/1995 | Frydman |
| 5,463,822 A | 11/1995 | Miller |
| 5,477,593 A | 12/1995 | Leick |
| D367,755 S | 3/1996 | Jones |
| D367,954 S | 3/1996 | Dion |
| 5,502,902 A | 4/1996 | Sussmann |
| 5,511,325 A | 4/1996 | Hieblinger |
| 5,526,585 A | 6/1996 | Brown et al. |
| 5,535,531 A | 7/1996 | Karabed et al. |
| 5,537,763 A | 7/1996 | Donnadieu et al. |
| 5,557,864 A | 9/1996 | Marks |
| 5,566,474 A | 10/1996 | Leick et al. |
| D375,831 S | 11/1996 | Perry |
| 5,596,820 A | 1/1997 | Edauw et al. |
| 5,599,000 A | 2/1997 | Bennett |
| 5,599,288 A | 2/1997 | Shirley et al. |
| 5,600,874 A | 2/1997 | Jungkind |
| 5,606,778 A | 3/1997 | Jungkind |
| 5,607,448 A | 3/1997 | Stahl et al. |
| D379,113 S | 5/1997 | McDonald et al. |
| 5,638,588 A | 6/1997 | Jungkind |
| 5,640,785 A | 6/1997 | Egelja |
| 5,647,104 A | 7/1997 | James |
| 5,651,198 A | 7/1997 | Sussmann |
| 5,669,116 A | 9/1997 | Jungkind |
| 5,692,319 A | 12/1997 | Parker et al. |
| 5,718,021 A | 2/1998 | Tatum |
| 5,718,065 A | 2/1998 | Locker |
| 5,720,084 A | 2/1998 | Chen |
| 5,732,483 A | 3/1998 | Cagliari |
| 5,732,648 A | 3/1998 | Aragon |
| 5,736,696 A | 4/1998 | Del Rosso |
| 5,737,854 A | 4/1998 | Sussmann |
| 5,755,044 A | 5/1998 | Veylupek |
| 5,756,298 A | 5/1998 | Burczak |
| 5,761,777 A | 6/1998 | Leick |
| 5,772,146 A | 6/1998 | Kawamoto et al. |
| 5,784,809 A | 7/1998 | McDonald |
| 5,791,068 A | 8/1998 | Bernier et al. |
| 5,819,378 A | 10/1998 | Doyle |
| 5,833,640 A | 11/1998 | Vazquez, Jr. et al. |
| 5,839,210 A | 11/1998 | Bernier et al. |
| 5,845,371 A | 12/1998 | Chen |
| 5,909,946 A | 6/1999 | Okajima |
| D413,197 S | 8/1999 | Faye |
| 5,934,599 A | 8/1999 | Hammerslag |
| 5,937,542 A | 8/1999 | Bourdeau |
| 5,956,823 A | 9/1999 | Borel |
| 5,971,946 A | 10/1999 | Quinn et al. |
| 6,015,110 A | 1/2000 | Lai |
| 6,038,791 A | 3/2000 | Cornelius et al. |
| 6,052,921 A | 4/2000 | Oreck |
| 6,070,886 A | 6/2000 | Cornelius et al. |
| 6,070,887 A | 6/2000 | Cornelius et al. |
| 6,083,857 A | 7/2000 | Bottger et al. |
| 6,088,936 A | 7/2000 | Bahl |
| 6,102,412 A | 8/2000 | Staffaroni |
| D430,724 S | 9/2000 | Matis et al. |
| 6,119,318 A | 9/2000 | Maurer |
| 6,119,372 A | 9/2000 | Okajima |
| 6,128,835 A | 10/2000 | Ritter et al. |
| 6,128,836 A | 10/2000 | Barret |
| 6,148,489 A | 11/2000 | Dickie et al. |
| 6,202,953 B1 | 3/2001 | Hammerslag |
| 6,219,891 B1 | 4/2001 | Maurer et al. |
| 6,240,657 B1 | 6/2001 | Weber et al. |
| 6,256,798 B1 | 7/2001 | Egolf et al. |
| 6,267,390 B1 | 7/2001 | Maravetz et al. |
| 6,286,233 B1 | 9/2001 | Gaither |
| 6,289,558 B1 | 9/2001 | Hammerslag |
| 6,311,633 B1 | 11/2001 | Keire |
| D456,130 S | 4/2002 | Towns |
| 6,370,743 B2 | 4/2002 | Choe |
| 6,401,364 B1 | 6/2002 | Burt |
| 6,416,074 B1 | 7/2002 | Maravetz et al. |
| 6,467,195 B2 | 10/2002 | Pierre et al. |
| 6,477,793 B1 | 11/2002 | Pruitt et al. |
| 6,502,286 B1 | 1/2003 | Dubberke |
| 6,543,159 B1 | 4/2003 | Carpenter et al. |
| 6,568,103 B2 | 5/2003 | Durocher |
| 6,606,804 B2 | 8/2003 | Kaneko et al. |
| 6,694,643 B1 | 2/2004 | Hsu |
| 6,708,376 B1 | 3/2004 | Landry |
| 6,711,787 B2 | 3/2004 | Jungkind et al. |
| 6,735,829 B2 | 5/2004 | Hsu |
| 6,757,991 B2 | 7/2004 | Sussmann |
| 6,775,928 B2 | 8/2004 | Grande et al. |
| 6,792,702 B2 | 9/2004 | Borsoi et al. |
| 6,802,439 B2 | 10/2004 | Azam et al. |
| 6,823,610 B1 | 11/2004 | Ashley |
| 6,871,812 B1 | 3/2005 | Chang |
| 6,877,256 B2 | 4/2005 | Martin et al. |
| 6,899,720 B1 | 5/2005 | McMillan |
| 6,922,917 B2 | 8/2005 | Kerns et al. |
| 6,938,913 B2 | 9/2005 | Elkington |
| 6,945,543 B2 | 9/2005 | De Bortoli et al. |
| D510,183 S | 10/2005 | Tresser |
| 6,976,972 B2 | 12/2005 | Bradshaw |
| 6,993,859 B2 | 2/2006 | Martin et al. |
| D521,226 S | 5/2006 | Douglas et al. |
| 7,073,279 B2 | 7/2006 | Min |
| 7,076,843 B2 | 7/2006 | Sakabayashi |
| 7,082,701 B2 | 8/2006 | Dalgaard et al. |
| 7,096,559 B2 | 8/2006 | Johnson et al. |
| 7,134,224 B2 | 11/2006 | Elkington et al. |
| 7,266,911 B2 | 9/2007 | Holzer et al. |
| 7,281,341 B2 | 10/2007 | Reagan et al. |
| 7,293,373 B2 | 11/2007 | Reagan et al. |
| 7,331,126 B2 | 2/2008 | Johnson |
| 7,343,701 B2 | 3/2008 | Pare et al. |
| 7,367,522 B2 | 5/2008 | Chen |
| 7,386,947 B2 | 6/2008 | Martin et al. |
| 7,392,602 B2 | 7/2008 | Reagan et al. |
| 7,401,423 B2 | 7/2008 | Reagan et al. |
| 7,490,458 B2 | 2/2009 | Ford |
| 7,568,298 B2 | 8/2009 | Kerns |
| 7,582,102 B2 | 9/2009 | Heinz et al. |
| 7,584,528 B2 | 9/2009 | Hu |
| 7,591,050 B2 | 9/2009 | Hammerslag |
| 7,597,675 B2 | 10/2009 | Ingimundarson et al. |
| 7,600,660 B2 | 10/2009 | Kasper et al. |
| 7,617,573 B2 | 11/2009 | Chen |
| 7,624,517 B2 | 12/2009 | Smith |
| 7,648,404 B1 | 1/2010 | Martin |
| 7,650,705 B2 | 1/2010 | Donnadieu et al. |
| 7,694,354 B2 | 4/2010 | Philpott et al. |
| 7,752,774 B2 | 7/2010 | Ussher |
| 7,757,412 B2 | 7/2010 | Farys |
| 7,774,956 B2 | 8/2010 | Dua et al. |
| D626,322 S | 11/2010 | Servettaz |
| 7,841,106 B2 | 11/2010 | Farys |

(56) References Cited

U.S. PATENT DOCUMENTS

| | | |
|---|---|---|
| 7,871,334 B2 | 1/2011 | Young et al. |
| 7,877,845 B2 | 2/2011 | Signori |
| 7,900,378 B1 | 3/2011 | Busse |
| 7,908,769 B2 | 3/2011 | Pellegrini |
| 7,947,061 B1 | 5/2011 | Reis |
| 7,950,112 B2 | 5/2011 | Hammerslag et al. |
| 7,954,204 B2 | 6/2011 | Hammerslag et al. |
| 7,963,049 B2 | 6/2011 | Messmer |
| 7,992,261 B2 | 8/2011 | Hammerslag et al. |
| D646,790 S | 10/2011 | Castillo et al. |
| 8,056,150 B2 | 11/2011 | Stokes et al. |
| 8,074,379 B2 | 12/2011 | Robinson, Jr. et al. |
| 8,091,182 B2 | 1/2012 | Hammerslag et al. |
| 8,109,015 B2 | 2/2012 | Signori |
| D663,850 S | 7/2012 | Joseph |
| D663,851 S | 7/2012 | Joseph |
| 8,215,033 B2 | 7/2012 | Carboy et al. |
| 8,231,074 B2 | 7/2012 | Hu et al. |
| D665,088 S | 8/2012 | Joseph |
| 8,235,321 B2 | 8/2012 | Chen |
| 8,245,371 B2 | 8/2012 | Chen |
| 8,257,293 B2 | 9/2012 | Ingimundarson et al. |
| 8,266,827 B2 | 9/2012 | Dojan et al. |
| 8,277,401 B2 | 10/2012 | Hammerslag et al. |
| 8,302,329 B2 | 11/2012 | Hurd et al. |
| 8,303,527 B2 | 11/2012 | Joseph |
| 8,308,098 B2 | 11/2012 | Chen |
| 8,353,087 B2 | 1/2013 | Chen |
| 8,353,088 B2 | 1/2013 | Ha |
| D677,045 S | 3/2013 | Voskuil |
| D679,019 S | 3/2013 | Siddle et al. |
| 8,434,200 B2 | 5/2013 | Chen |
| 8,490,299 B2 | 7/2013 | Dua et al. |
| 8,516,662 B2 | 8/2013 | Goodman et al. |
| 8,578,632 B2 | 11/2013 | Bell et al. |
| 8,652,164 B1 | 2/2014 | Aston |
| 8,713,820 B2 | 5/2014 | Kerns et al. |
| 8,984,719 B2 | 3/2015 | Soderberg et al. |
| 9,072,341 B2 | 7/2015 | Jungkind |
| D735,987 S | 8/2015 | Hsu |
| 9,101,181 B2 | 8/2015 | Soderberg et al. |
| 9,125,455 B2 | 9/2015 | Kerns et al. |
| 9,138,030 B2 | 9/2015 | Soderberg et al. |
| 2002/0050076 A1 | 5/2002 | Borsoi et al. |
| 2002/0062579 A1 | 5/2002 | Caeran |
| 2002/0095750 A1 | 7/2002 | Hammerslag |
| 2002/0129518 A1 | 9/2002 | Borsoi et al. |
| 2002/0148142 A1 | 10/2002 | Oorei et al. |
| 2002/0166260 A1 | 11/2002 | Borsoi |
| 2002/0178548 A1 | 12/2002 | Freed |
| 2003/0079376 A1 | 5/2003 | Oorei et al. |
| 2003/0144620 A1 | 7/2003 | Sieller |
| 2003/0150135 A1 | 8/2003 | Liu |
| 2003/0177662 A1 | 9/2003 | Elkington et al. |
| 2003/0204938 A1 | 11/2003 | Hammerslag |
| 2004/0041452 A1 | 3/2004 | Williams |
| 2004/0211039 A1 | 10/2004 | Livingston |
| 2005/0054962 A1 | 3/2005 | Bradshaw |
| 2005/0060912 A1 | 3/2005 | Holzer et al. |
| 2005/0081339 A1 | 4/2005 | Sakabayashi |
| 2005/0081403 A1 | 4/2005 | Mathieu |
| 2005/0087115 A1 | 4/2005 | Martin |
| 2005/0098673 A1 | 5/2005 | Huang |
| 2005/0102861 A1 | 5/2005 | Martin |
| 2005/0126043 A1 | 6/2005 | Reagan et al. |
| 2005/0172463 A1 | 8/2005 | Rolla |
| 2005/0184186 A1 | 8/2005 | Tsoi et al. |
| 2005/0198866 A1 | 9/2005 | Wiper et al. |
| 2006/0135901 A1 | 6/2006 | Ingimundarson et al. |
| 2006/0156517 A1 | 7/2006 | Hammerslag et al. |
| 2006/0179685 A1 | 8/2006 | Borel et al. |
| 2006/0185193 A1 | 8/2006 | Pellegrini |
| 2006/0287627 A1 | 12/2006 | Johnson |
| 2007/0006489 A1* | 1/2007 | Case .................. A43B 3/0005 36/132 |
| 2007/0063459 A1 | 3/2007 | Kavarsky |
| 2007/0068040 A1 | 3/2007 | Farys |
| 2007/0084956 A1 | 4/2007 | Chen |
| 2007/0113524 A1 | 5/2007 | Lander |
| 2007/0128959 A1 | 6/2007 | Cooke |
| 2007/0169378 A1 | 7/2007 | Sodeberg et al. |
| 2008/0016717 A1 | 1/2008 | Ruban |
| 2008/0060167 A1 | 3/2008 | Hammerslag et al. |
| 2008/0060168 A1 | 3/2008 | Hammerslag et al. |
| 2008/0066272 A1* | 3/2008 | Hammerslag ........... A43C 11/14 24/712 |
| 2008/0066345 A1 | 3/2008 | Hammerslag et al. |
| 2008/0066346 A1 | 3/2008 | Hammerslag et al. |
| 2008/0068204 A1 | 3/2008 | Carmen et al. |
| 2008/0083135 A1 | 4/2008 | Hammerslag et al. |
| 2008/0092279 A1 | 4/2008 | Chiang |
| 2008/0172848 A1 | 7/2008 | Chen |
| 2008/0196224 A1 | 8/2008 | Hu |
| 2009/0019734 A1 | 1/2009 | Reagan et al. |
| 2009/0071041 A1 | 3/2009 | Hooper |
| 2009/0090029 A1 | 4/2009 | Kishino |
| 2009/0172928 A1 | 7/2009 | Messmer et al. |
| 2009/0184189 A1 | 7/2009 | Soderberg et al. |
| 2009/0272007 A1* | 11/2009 | Beers .................. A43B 3/0005 36/50.1 |
| 2009/0277043 A1 | 11/2009 | Graser et al. |
| 2010/0064547 A1 | 3/2010 | Kaplan |
| 2010/0101061 A1 | 4/2010 | Ha |
| 2010/0139057 A1 | 6/2010 | Soderberg et al. |
| 2010/0154254 A1 | 6/2010 | Fletcher |
| 2010/0175163 A1 | 7/2010 | Litke |
| 2010/0251524 A1 | 10/2010 | Chen |
| 2010/0299959 A1 | 12/2010 | Hammerslag |
| 2010/0319216 A1 | 12/2010 | Grenzke et al. |
| 2011/0000173 A1 | 1/2011 | Lander |
| 2011/0071647 A1 | 3/2011 | Mahon |
| 2011/0162236 A1 | 7/2011 | Voskuil et al. |
| 2011/0167543 A1 | 7/2011 | Kovacevich et al. |
| 2011/0191992 A1 | 8/2011 | Chen |
| 2011/0197362 A1 | 8/2011 | Chella et al. |
| 2011/0225843 A1 | 9/2011 | Kerns et al. |
| 2011/0258876 A1 | 10/2011 | Baker et al. |
| 2011/0266384 A1 | 11/2011 | Goodman et al. |
| 2012/0000091 A1 | 1/2012 | Cotterman et al. |
| 2012/0004587 A1 | 1/2012 | Nickel et al. |
| 2012/0005995 A1 | 1/2012 | Emery |
| 2012/0023717 A1 | 2/2012 | Chen |
| 2012/0047620 A1 | 3/2012 | Ellis et al. |
| 2012/0101417 A1 | 4/2012 | Joseph |
| 2012/0102783 A1 | 5/2012 | Swigart et al. |
| 2012/0138882 A1 | 6/2012 | Moore et al. |
| 2012/0157902 A1 | 6/2012 | Castillo et al. |
| 2012/0167290 A1 | 7/2012 | Kovacevich et al. |
| 2012/0174437 A1 | 7/2012 | Heard |
| 2012/0228419 A1 | 9/2012 | Chen |
| 2012/0246974 A1 | 10/2012 | Hammerslag et al. |
| 2012/0310273 A1 | 12/2012 | Thorpe |
| 2013/0012856 A1 | 1/2013 | Hammerslag et al. |
| 2013/0014359 A1 | 1/2013 | Chen |
| 2013/0019501 A1 | 1/2013 | Gerber |
| 2013/0025100 A1 | 1/2013 | Ha |
| 2013/0091667 A1 | 4/2013 | Zerfas et al. |
| 2013/0091674 A1 | 4/2013 | Chen |
| 2013/0092780 A1 | 4/2013 | Soderberg et al. |
| 2013/0269219 A1 | 10/2013 | Burns et al. |
| 2013/0277485 A1 | 10/2013 | Soderberg et al. |
| 2013/0340283 A1 | 12/2013 | Bell et al. |
| 2013/0345612 A1* | 12/2013 | Bannister .............. A61B 5/1116 602/19 |
| 2014/0082963 A1 | 3/2014 | Beers |
| 2014/0094728 A1 | 4/2014 | Soderberg et al. |
| 2014/0117140 A1 | 5/2014 | Goodman et al. |
| 2014/0123440 A1 | 5/2014 | Capra et al. |
| 2014/0123449 A1 | 5/2014 | Soderberg et al. |
| 2014/0208550 A1 | 7/2014 | Neiley |
| 2014/0221889 A1 | 8/2014 | Burns et al. |
| 2014/0257156 A1 | 9/2014 | Capra et al. |
| 2014/0290016 A1 | 10/2014 | Lovett et al. |
| 2014/0359981 A1 | 12/2014 | Cotterman et al. |

(56) References Cited

U.S. PATENT DOCUMENTS

| | | |
|---|---|---|
| 2015/0007422 A1 | 1/2015 | Cavanagh et al. |
| 2015/0014463 A1 | 1/2015 | Converse et al. |
| 2015/0026936 A1 | 1/2015 | Kerns et al. |
| 2015/0033519 A1 | 2/2015 | Hammerslag et al. |
| 2015/0059206 A1 | 3/2015 | Lovett et al. |
| 2015/0076272 A1 | 3/2015 | Trudel et al. |
| 2015/0089779 A1 | 4/2015 | Lawrence et al. |
| 2015/0089835 A1 | 4/2015 | Hammerslag et al. |
| 2015/0101160 A1 | 4/2015 | Soderberg et al. |
| 2015/0150705 A1 | 6/2015 | Capra et al. |
| 2015/0151070 A1 | 6/2015 | Capra et al. |
| 2015/0190262 A1 | 7/2015 | Capra et al. |
| 2015/0223608 A1 | 8/2015 | Capra et al. |
| 2015/0237962 A1 | 8/2015 | Soderberg et al. |
| 2015/0335458 A1 | 11/2015 | Romo |

FOREIGN PATENT DOCUMENTS

| | | |
|---|---|---|
| CH | 199766 | 9/1938 |
| CH | 204 834 A | 5/1939 |
| CN | 2613167 | 4/2004 |
| CN | 201015448 | 2/2008 |
| DE | 641976 | 2/1937 |
| DE | 23 41 658 | 3/1974 |
| DE | 29 00 077 A1 | 7/1980 |
| DE | 31 01 952 A1 | 9/1982 |
| DE | 38 13 470 | 11/1989 |
| DE | 43 02 401 A1 | 8/1994 |
| DE | 43 05 671 A1 | 9/1994 |
| DE | 9308037 | 10/1994 |
| DE | 43 26 049 A1 | 2/1995 |
| DE | 9315776 | 2/1995 |
| DE | 29503552.8 | 4/1995 |
| DE | 196 24 553 | 1/1998 |
| DE | 19945045 A1 | 3/2001 |
| DE | 20 2010 000 354 U1 | 6/2010 |
| DE | 11 2013 005 273 T5 | 9/2015 |
| EP | 0 056 953 | 8/1982 |
| EP | 0 099 504 | 2/1984 |
| EP | 0 123 050 | 10/1984 |
| EP | 0 155 596 | 9/1985 |
| EP | 0 201 051 | 11/1986 |
| EP | 0 255 869 | 2/1988 |
| EP | 0 393 380 | 10/1990 |
| EP | 0 589 232 A1 | 3/1994 |
| EP | 0 589 233 A1 | 3/1994 |
| EP | 0 614 625 A1 | 9/1994 |
| EP | 0 651 954 A1 | 5/1995 |
| EP | 0 679 346 | 11/1995 |
| EP | 0 693 260 B1 | 1/1996 |
| EP | 0 734 662 A1 | 10/1996 |
| EP | 0 848 917 | 6/1998 |
| EP | 0 923 965 | 6/1999 |
| EP | 0 937 467 | 8/1999 |
| EP | 1163860 | 12/2001 |
| EP | 1 219 195 | 7/2002 |
| EP | 1 236 412 A | 9/2002 |
| EP | 2298107 B1 | 3/2011 |
| EP | 2359708 | 8/2011 |
| FR | 1 404 799 | 7/1965 |
| FR | 2 019 991 A | 7/1970 |
| FR | 2 598 292 A1 | 11/1987 |
| FR | 2 726 440 A1 | 5/1996 |
| FR | 2 770 379 A1 | 5/1999 |
| FR | 2 814 919 A1 | 4/2002 |
| GB | 189911673 | 7/1899 |
| GB | 216400 | 5/1924 |
| GB | 2 449 722 A | 12/2008 |
| IT | 1220811 | 6/1990 |
| JP | 51-121375 | 10/1976 |
| JP | 53-124987 | 3/1977 |
| JP | 54-108125 | 2/1978 |
| JP | H02-236025 | 9/1990 |
| JP | 6-284906 | 2/1996 |
| JP | 3030988 | 11/1996 |
| JP | 3031760 | 12/1996 |
| JP | 10-199366 | 7/1998 |
| JP | 2004-016732 | 1/2004 |
| JP | 2004-041666 | 2/2004 |
| JP | 2009-504210 | 2/2009 |
| KR | 20-0367882 | 11/2004 |
| KR | 20-0400568 | 8/2005 |
| KR | 10-0598627 | 7/2006 |
| KR | 10-0953398 | 4/2010 |
| KR | 10-1025134 B1 | 3/2011 |
| KR | 10-1028468 | 4/2011 |
| KR | 10-1053551 | 7/2011 |
| PA | 2003 A 000197 | 4/2003 |
| PA | 2003 A 000198 | 3/2005 |
| WO | WO 94/27456 | 12/1994 |
| WO | WO 95/11602 | 5/1995 |
| WO | WO 95/03720 | 9/1995 |
| WO | WO 98/33408 | 8/1998 |
| WO | WO 98/37782 | 9/1998 |
| WO | WO 99/09850 | 3/1999 |
| WO | WO 99/15043 | 4/1999 |
| WO | WO 99/43231 | 9/1999 |
| WO | WO 00/53045 | 9/2000 |
| WO | WO 00/76337 A1 | 12/2000 |
| WO | WO 01/08525 | 2/2001 |
| WO | WO 01/15559 | 3/2001 |
| WO | WO 02/051511 | 7/2002 |
| WO | WO 2004/093569 | 11/2004 |
| WO | WO 2005/013748 A1 | 2/2005 |
| WO | WO/2007/016983 | 2/2007 |
| WO | WO 2008/015214 | 2/2008 |
| WO | WO/2008/033963 | 3/2008 |
| WO | 2009/134864 A2 | 11/2009 |
| WO | WO/2009/134858 | 11/2009 |
| WO | WO 2010/059989 A2 | 5/2010 |
| WO | WO 2012/165803 A2 | 12/2012 |
| WO | 2013/025704 A1 | 2/2013 |
| WO | 2014/036371 A1 | 3/2014 |
| WO | WO/2015/035885 | 3/2015 |
| WO | WO 2015/179332 A1 | 11/2015 |
| WO | WO 2015/181928 A1 | 12/2015 |

OTHER PUBLICATIONS

U.S. Appl. No. 09/956,601, filed Sep. 18, 2001, Hammerslag.
Asolo® Boot Brochure Catalog upon information and belief date is as early as Aug. 22, 1997, 12 pages.
La Sportiva, A Technical Lightweight Double Boot for Cold Environments, 1 page. Accessed on May 27, 2015. Retrieved from http://www.sportiva.com/products/footwear/mountain/spantik.
"Strength of materials used to make my Safety Harnesses," Elaine, Inc. Jul. 9, 2012. Retrieved from <https://web.archive.org/web/20120709002720/http://www.childharness.ca/strength_data.html> on Mar. 17, 2014, 2 pages.
International Search Report and Written Opinion for PCT/US2013/032326 mailed Jun. 14, 2013, 27 pages.
International Preliminary Report on Patentability for PCT/US2013/032326 issued Sep. 16, 2014, 6 pages.
International Search Report and Written Opinion for PCT/US2013/057637 mailed Apr. 7, 2014, 34 pages.
International Preliminary Report on Patentability for PCT/US2013/057637 issued Mar. 3, 2015, 9 pages.
International Search Report and Written Opinion for PCT/US2013/068342 mailed Apr. 7, 2014, 29 pages.
International Preliminary Report on Patentability for PCT/US2013/068342 issued May 5, 2015, 9 pages.
International Search Report and Written Opinion for PCT/US2014/014952 mailed Apr. 25, 2014, 17 pages.
International Preliminary Report on Patentability for PCT/US2014/014952 issued Aug. 11, 2015, 9 pages.
International Search Report and Written Opinion for PCT/US2014/066212 mailed Apr. 22, 2015, 16 pages.
International Search Report and Written Opinion for PCT/US2014/032574 mailed Oct. 31, 2014, 19 pages.
International Search Report and Written Opinion for PCT/US2014/045291 mailed Nov. 6, 2014, 12 pages.

(56) References Cited

OTHER PUBLICATIONS

International Search Report and Written Opinion for PCT/US2014/013458 mailed May 19, 2014, 12 pages.
International Preliminary Report on Patentability for PCT/US2014/013458 issued Jul. 28, 2015, 7 pages.
International Search Report and Written Opinion for PCT/US2013/068814 mailed Jun. 9, 2014, 18 pages.
International Preliminary Report on Patentability for PCT/US2013/068814 issued May 12, 2015, 12 pages.
Notice of Reasons for Rejection from the Japanese Patent Office dated Feb. 26, 2015 for design application No. 2014-015570, 4 pages.
Receipt of Certificate of Design Registration No. 1529678 from the Japanese Patent Office for design application No. 2014-015570 dated Jun. 26, 2015, 1 page.
International Search Report and Written Opinion for PCT/US2014/055710 mailed Jul. 6, 2015, 19 pages.
International Search Report and Written Opinion for PCT/US2014/054420 mailed Jul. 6, 2015, 21 pages.
The Preliminary Rejections from the Korean Intellectual Property Office for Application No. 30/2014-34959 received Aug. 7, 2015, is not translated into English. The document requests a renaming of the application to be in accordance with Korean patent law, 5 pages total.
The Preliminary Rejections from the Korean Intellectual Property Office for Application No. 30-2014-34959 received Apr. 7, 2015, is not translated into English. The document requests a revision of the drawings to be in accordance with Korean patent law, 6 pages total.
Certificate of Design Registration No. 30-809409 on Aug. 3, 2015 from the Korean Intellectual Property Office for Appln No. 30-2015-11475, 2 pages.
Certificate of Design Registration No. 30-809410 on Aug. 3, 2015 from the Korean Intellectual Property Office for Appln No. 30-2015-11476, 2 pages.
European Search Report for EP 14168875 mailed Oct. 29, 2014, 9 pages.
International Search Report and Written Opinion for PCT/US2014/020894 mailed Jun. 20, 2014, 12 pages.
International Preliminary Report on Patentability for PCT/US2014/020894 issued Sep. 8, 2015, 7 pages.
International Search Report and Written Opinion for PCT/US2014/041144 mailed Dec. 10, 2014, 13 pages.
International Preliminary Report on Patentability for PCT/US2014/032574 issued Oct. 6, 2015, 12 pages.
International Search Report and Written Opinion for PCT/US2014/046238 mailed Nov. 21, 2014, 17 pages.
Office Action received Oct. 8, 2015 from the German Patent and Trademark Office for Appln No. 402015100191.2, regarding the title of the invention, 2 pages.
Anonymous, "Shore durometer," Wikipedia, the free encyclopedia, Mar. 10, 2012, XP002747470, Retrieved from the Internet: URL: https://en.wikipedia.org/w/index.php?title=Shore_durometer&oldid=481128180 [retrieved on Oct. 20, 2015] *shore A, shore D, durometer, polymer, rubber, gel; the whole document *, 6 pages.
Notice of Reasons for Rejection from the Japanese Patent Office dated Oct. 5, 2015 for design application No. 2015-004923, 4 pages.
"Save Tourniquet," 3 pages. Copyright 2015. Accessed on Dec. 11, 2015. Retrieved from http://www.savetourniquet.com/.
International Preliminary Report on Patentability for PCT/US2014/041144 issued Dec. 8, 2015, all pages.
Supplementary European Search Report for EP 13761841 dated Oct. 21, 2015, all pages.
European Search Report for EP 14 76 0642 dated Aug. 5, 2016, 8 pages.

* cited by examiner

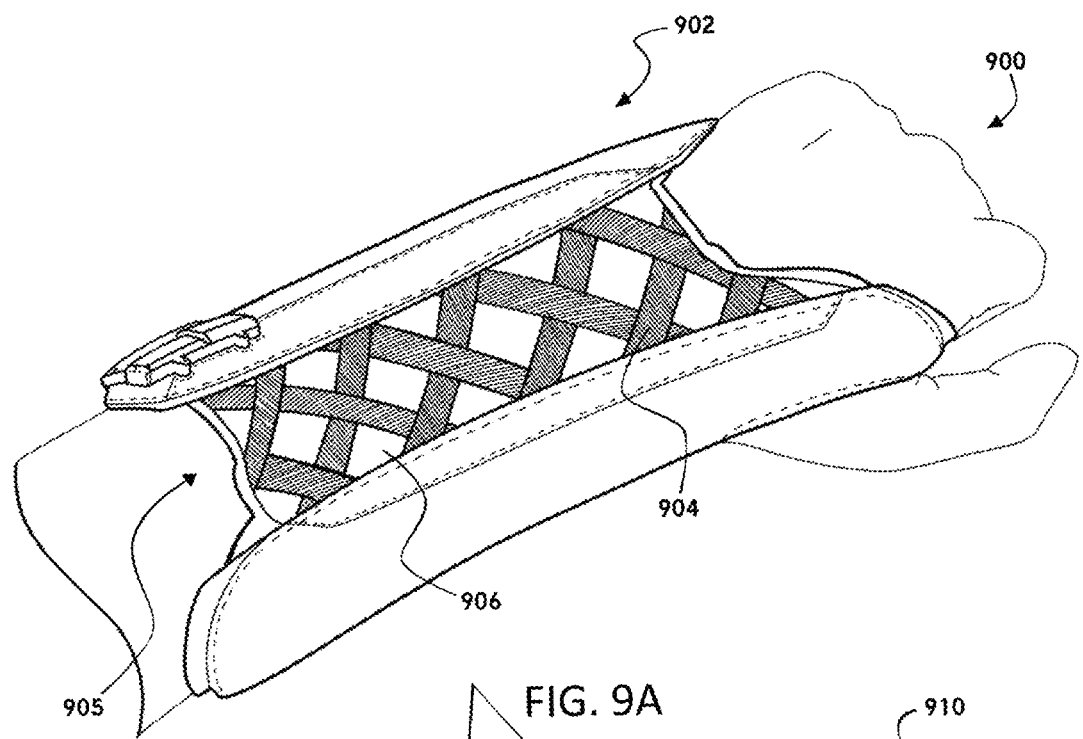
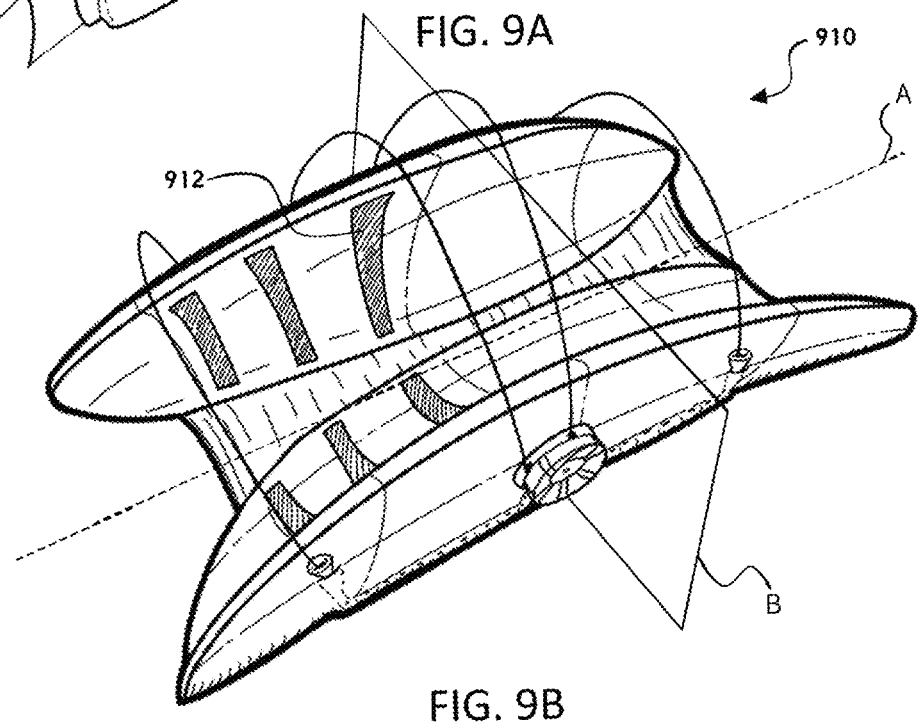

Time Worn
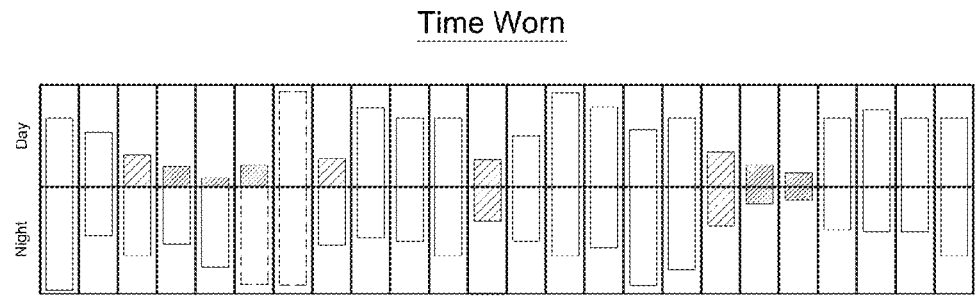
FIG. 13A
While Worn:
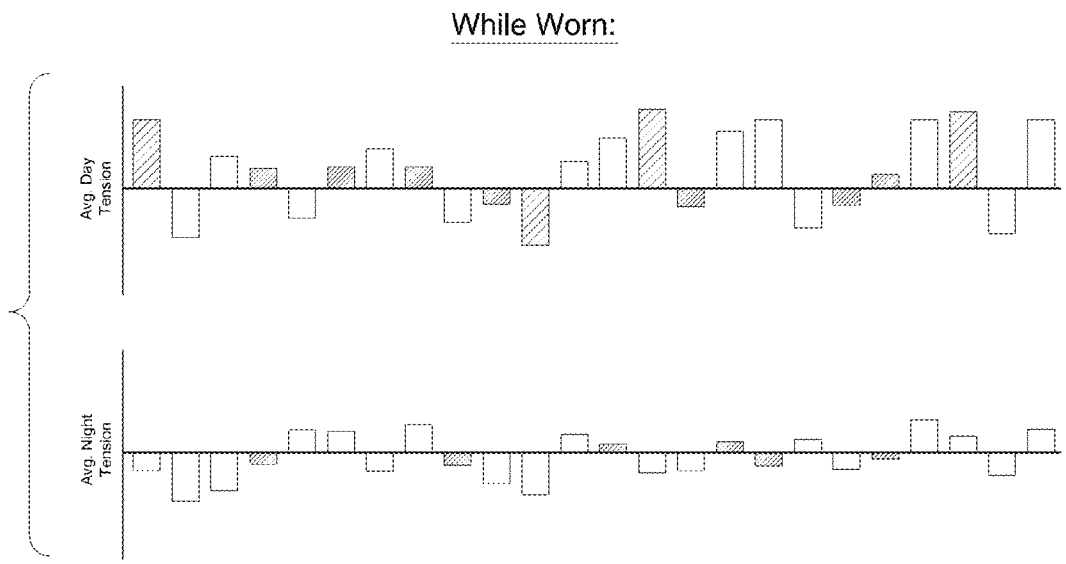
FIG. 13B
Activity Level:
| Reported events per day Targets: | | | | | | | | | | | | | | | | | | | | | | | |
|---|---|---|---|---|---|---|---|---|---|---|---|---|---|---|---|---|---|---|---|---|---|---|---|
| High <1 | HIGH | 0 | 0 | 0 | 0 | 0 | 1 | 0 | 0 | 0 | 0 | 0 | 0 | 0 | 0 | 0 | 0 | 0 | 0 | 1 | 0 | 0 | 0 |
| Med <6 | MED | 3 | 4 | 3 | 5 | 8 | 2 | 3 | 3 | 3 | 3 | 5 | 4 | 7 | 5 | 4 | 3 | 3 | 2 | 3 | 4 | 4 | 6 | 1 | 3 |
| Low <10 | LOW | 8 | 7 | 8 | 7 | 10 | 7 | 7 | 7 | 7 | 7 | 7 | 7 | 7 | 7 | 7 | 7 | 7 | 7 | 7 | 7 | 7 | 7 | 7 |
FIG. 13C

SYSTEMS, METHODS, AND DEVICES FOR AUTOMATIC CLOSURE OF MEDICAL DEVICES

CROSS-REFERENCES TO RELATED APPLICATIONS

This application claims the benefit of U.S. Provisional Application No. 61/772,935, filed on Mar. 5, 2013, and titled "Systems, Methods, and Devices for Automatic Closure of Medical Devices." The entire disclosure of that application is incorporated by reference herein for all purposes.

BACKGROUND OF THE INVENTION

The present embodiments relate generally to medical braces, devices, and other articles including tensioning systems.

Medical braces are typically fit about a limb and tightened to secure the brace about the limb. Conventional tightening for braces often require a user to use both hands in securing the brace about a limb. For example, Velcro® straps and buckles often require the user to grasp the strap or the body of the brace to hold the brace or strap in position while the strap is secured to the brace. Properly fitting such braces may be difficult and/or challenging for patients, especially when the patient is dexterity challenged or the brace is being fit to the arm or hand.

BRIEF SUMMARY OF THE INVENTION

The present invention generally provides improved motorized closure devices, systems, and methods that may be used to tighten a brace or other apparel about a limb. According to one aspect, a method for automatically opening and closing a brace about a limb is provided. The method includes a brace that is in an initially open configuration to aid in donning of the brace about the limb. The brace includes a motorized tensioning device, a control unit communicatively coupled with the motorized tensioning device, and an opening mechanism that opens the brace as the tension of the tensioning member tension is reduced. The motorized tensioning device and control unit are configured to adjust a tension of a tensioning member of the brace. The method includes receiving a first input at the control unit and communicating a first instruction from the control unit to the motorized tensioning device. The first instruction includes a tension value for the tensioning member that is greater than an initial tension of the tensioning member. The method also includes tensioning the tensioning member to substantially the tension value via the motorized tensioning device so as to close and tighten the brace about the limb. The method further includes receiving a second input via the control unit and communicating a second instruction from the control unit to the motorized tensioning device. The method additionally includes reducing the tension of the tensioning member via the motorized tensioning device so as to loosen the brace about the limb and to enable opening of the brace via the opening mechanism to aid in doffing of the brace.

According to another aspect, a method for tightening a brace about a limb is provided. The method includes a brace having a motorized tensioning device and a control unit communicatively coupled with the motorized tensioning device. The motorized tensioning device and control unit are configured to adjust a tension of a tensioning member of the brace to tighten the brace about the limb. The method includes receiving, at the control unit, a prescribed parameter for the brace that is determined to therapeutically benefit the limb and communicating a first instruction from the control unit to the motorized tensioning device to tension the tensioning member to a tension value determined from the prescribed parameter. The method also includes tensioning, via the motorized tensioning device, the tensioning member to substantially the tension value so as to adjust a fit of the brace about the limb in accordance with the prescribed parameter. The method further includes monitoring, via the control unit, the fit of the brace about the limb over a period of time and comparing the monitored fit of the brace to the prescribed parameter to determine that the fit of the brace exceeds a variance threshold for the fit. The method additionally includes communicating a second instruction from the control unit to the motorized tensioning device to adjust the fit of the brace about the limb and adjusting the tension of the tensioning member via the motorized tensioning device so that the fit of the brace about the limb is in accordance with the prescribed parameter.

According to another aspect, a method for providing therapy with a brace fitted about a limb is provided. The method includes a brace having a motorized tensioning device, a tensioning member operationally coupled with the motorized tensioning device to tighten the brace about the limb, and a control unit communicatively coupled with the motorized tensioning device to control adjustment of a tension of the tensioning member. The method includes communicating a first instruction from the control unit to the motorized tensioning device to cyclically or repetitively adjust the tension of the tensioning member according to a therapeutic regimen that is designed to aid in recovery of the limb via cyclical or repetitive movement of the limb. The method may also include receiving the therapeutic regimen at the control unit and cyclically or repetitively controlling the tension of the tensioning member via the motorized tensioning device in accordance with the therapeutic regimen to enable flexing of the brace to promote repetitive or cyclical movement and therapeutic healing of the limb.

BRIEF DESCRIPTION OF THE DRAWINGS

The present invention is described in conjunction with the appended figures:

FIGS. 5F-6E illustrates various methods of using a control unit and/or motorized tensioning device to fit a brace about a limb.

FIGS. 9A-C illustrate various sensors that may be used with the brace and/or motorized tensioning device to monitor conditions of the user.

FIGS. 9D-P illustrate various embodiments of devices, systems, or controls that may be used to determine a tension that is applied to the lace via a motorized tensioning device.

FIGS. 13A-C illustrates an exemplary report of a patient's usage of a brace based on data collected during use of the brace.

Figure 1A:
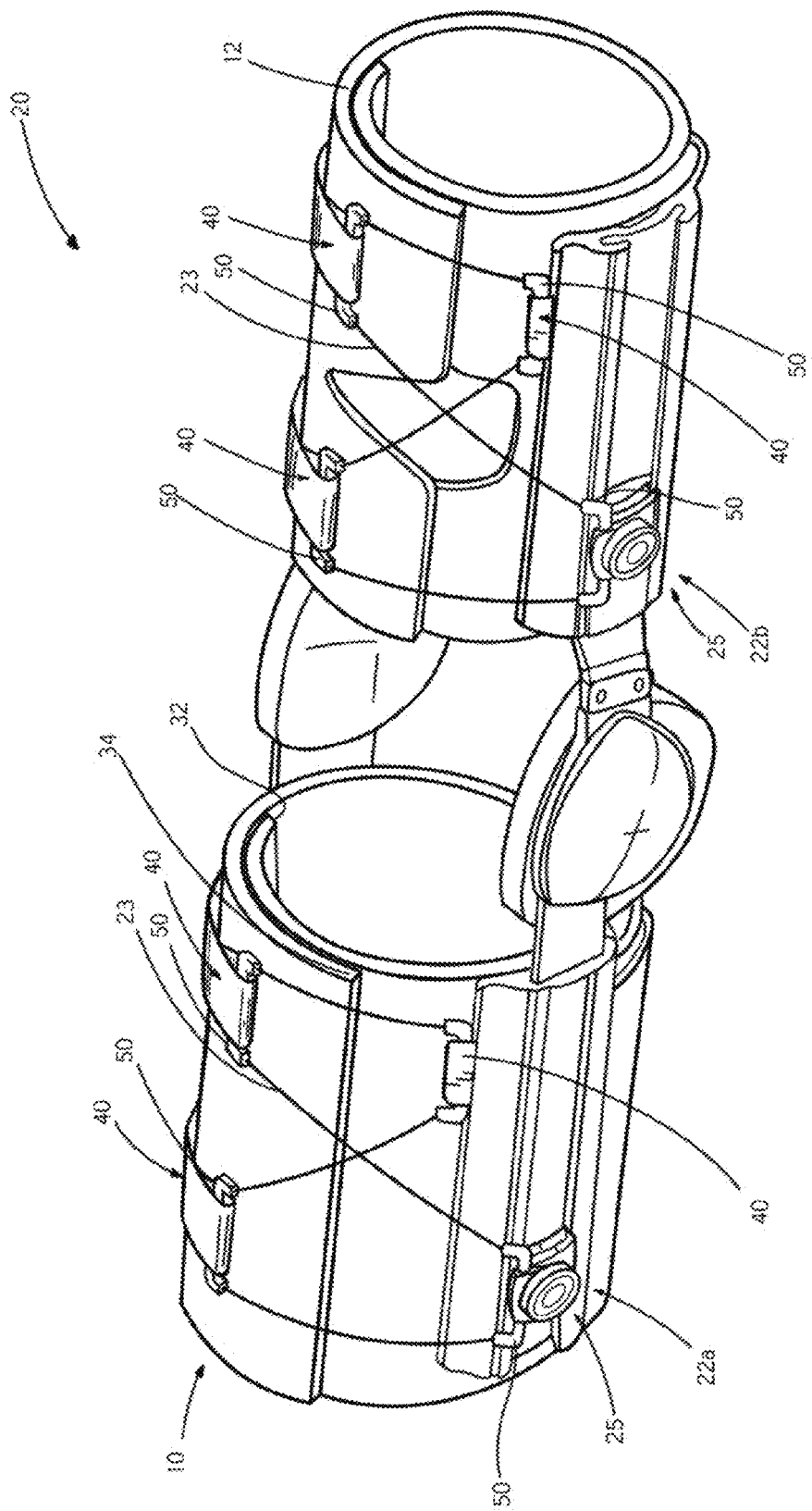
FIGS. 1A-3 illustrate embodiments of a brace and motorized tensioning device that may be used to close and tighten the brace.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The embodiments described herein provide various motorized closure devices that may be used with braces (medical, sports, and the like), or various other apparel, such as footwear, hats, gloves, and the like. The embodiments described herein may find particular usefulness in medical braces and for ease in describing the embodiments, the disclosure will focus mainly on medical braces. It should be realized, however, that the embodiments are not limited to use for only medical braces. The embodiments may provide devices that are configured to open and close a brace to allow a user to don and doff the brace. The motorized closure devices described herein provide several benefits over conventional closure devices. One benefit among many of the motorized closure devices is the ability of the brace to have repeatable closure. Stated differently, the motorized closure devices allow the brace to be closed approximately equivalent each time the brace is closed. Repeatable closure makes donning and doffing of the brace simple for a patient because the patient merely needs to actuate the motorized closure device, such as by pressing a button, to open or close the brace. Repeatable closure also allows the physician to prescribe a "dosage" or fit of the brace. For example, the physician may prescribe that the brace be "fit" with a defined tension or pressure, which motorized closure device may provide.

Another benefit of the motorized closure device is the ability to display the tension or brace tightness achieved by the closure device. In some embodiments the tension may be digitally displayed or otherwise communicated to the patient. Displaying the tension allows the patient to repeatably dose or tighten the brace to a preferred tension and allows the patient to quickly determine if the tension or fit of the brace has changed, such as due to stretch of the product, change in body size, and the like. In some embodiments, the motorized closure device may be configured to automatically adjust the tension of the brace to keep the brace within a defined tension or fit. For example, as the patient's limb shrinks and swells and the tension or fit of the brace increases or decreases, the motorized closure device may operate to tension or loosen the brace as needed to keep the brace within a defined tension range.

An additional benefit of the motorized closure device is that the brace may be easily fit about a patient's body part. For example, in some embodiments, the brace may include a mechanism that allows the brace to automatically open. The mechanism may include a spring positioned between opposing edges or stays (i.e., rigid portions of the brace adjacent an opening) to keep the brace open. This allows the brace to be easily donned, which may be convenient for disabled or otherwise dexterity challenged individuals. The automatic opening stays also reduce lace tangling by proactively keeping the lace tensioned as the brace is opened. In some embodiments, the brace may be automatically opened by pressing a button or other mechanism of the brace.

As briefly described above, the motorized closure device helps reduce or eliminate dexterity issues that are common with conventional braces. This is achieved by removing manual closure mechanisms and/or by providing a brace that automatically opens. Stated differently, the controls that allow a patient to don the brace and close the brace about a body part are greatly simplified when compared to conventional braces.

In some embodiments, the motorized closure device may be configured to measure an internal tension or pressure and may be further configured to automatically adjust in response to the measured tension so as to maintain a prescribed or preferred tension level. Automatically tensioning the brace in this manner helps prevent issues with over tensioned braces, such as compartment syndrome when a limb swells while in a confined space. Automatic tensioning also allows the brace to adjust to a limb as it shrinks or expands due to swelling and/or atrophy. In addition, the tension may be automatically adjusted to provide additional support if and/or when the brace detects that additional support is needed such as when a user is falling on the injured limb. The brace may include an accelerometer or other sensing device that is able to detect when additional support is needed and provide this information to a control unit of the motorized closure device to allow the closure device to quickly and accurately tension the brace.

In other embodiments, the brace may be used to proactively provide compression to the limb as desired. For example, the brace may be designed to compress the limb on a timed interval so as to change tension within zones of the limb and thereby encourage blood or fluid flow into or out of the limb to promote healing. In another embodiment, the brace may be able to detect the activity level of the patient and adjust to the predetermined tension levels. For example, the brace may be able to detect if the patient is sitting, standing, or performing an activity (e.g., walking, running, and the like). Each of these activities may require a different level of tension for the brace and the brace may be configured to respond accordingly. For example, when the brace determines that the patient is sitting, the tension in the brace may be relaxed to provide additional comfort. Likewise, when it is determined that the patient is walking or running, the tension of the brace may be tightened to provide additional support.

In some embodiments, the motorized closure device may be configured to gather data recorded as the patient wears the brace and to provide this data to a centralized server. This data may be used to monitor a patient's compliance in wearing the brace according to a prescribed regimen, to monitor progress in healing, to monitor the effectiveness of a prescribed fit in terms of healing and/or comfort, and the like. Other details or conditions could be monitored via the brace as well, including swelling, atrophy, and the like of the limb, or the donning and doffing of the brace, the time of use, the patient's compliance with a prescribed regimen, and the like. Data collection may involve wired or wireless techniques including the use of USB, data cords, Bluetooth, and the like. The data may be provided to a physician so as to allow a physician to monitor the progress of the patient and/or adjust a prescribed therapy or to recommend a new therapy.

The motorized closure device embodiments provide many additional benefits over conventional brace closure devices in relation to a patient's compliance with wearing the brace. For example, the motorized closure device may be programmed to react only to user inputs that occur during certain time periods so as to manage the ability of the patient to open and close the brace. In other embodiments, the patient may be allowed to adjust the tension of the brace, but only within a prescribed range. The brace may likewise be configured to only allow the patient to remove the brace a specified number of times in a given period and/or per day. The duration the patient actually wears the brace and/or the tension levels applied to the brace may likewise be monitored and transmitted to a physician and/or stored in a central server. In some embodiments, the physician may send messages to the user, which are displayed on a user interface of the brace, such as a reminder to wear the brace and/or perform a prescribed physical therapy regimen.

In some embodiments, the physician may be able to adjust one or more parameters of the brace remotely, such as the tension applied or the range within which the patient may tighten or loosen the brace. The physician may change these parameters on an electronic device (e.g., personal or laptop computer, tablet PC, smart phone, and the like) and instructions may be transmitted to the motorized closure device to adjust the fit of the brace or other parameters in accordance with the physician's changes. For example, via Bluetooth communication, the physician may change a setting of the motorized closure device to allow the patient to only lower the tension by five percent. The physician may also set a time frame of two weeks in which the tension may be adjusted. After this time period, the patient may be allowed to remove the brace. In some embodiments, the physician may control the time periods (e.g., morning hours, evening hours, etc.) in which the fit of the brace may be manipulated by the patient, or may control a duration of time that the brace may be adjusted (e.g., fifteen minutes per hour, etc.).

The motorized closure device may include an alarm that sounds when the brace is not being worn as recommended by the physician. In some embodiments, the alarm may sound until the patient complies with the physician's recommendations. In addition, a message may be transmitted to the physician to inform the physician that the patient is not complying with the recommendations or prescribed regimen. The device may monitor the duration in which the patient does not comply with the physician's recommendations and record these events.

In some embodiments, the controls of the medical closure device may be provided on a smart phone or other electronic device to allow the patient to quickly and easily tighten or loosen the brace. In another embodiment, the electronic device may monitor the tension applied to the lace by the patient. An application of the electronic device may learn the tensioning patterns of the patient and automatically apply tension to the lace in accordance with the patient's tensioning patterns. Stated differently, the electronic device, or an application of the electronic device, may automatically tension the brace at a set time and/or loosen the brace at a set time in accordance with patterns that the electronic device learns by monitoring the patient's lace tensioning patterns.

In some embodiments, the motorized closure device may include a tension indicator. The tension indicator may be a mechanical tension indicator (e.g., spring and scale, compliant foam or other material, and the like) or a digital indicator that is coupled with a tension measuring device. The measured tension could be transmitted to the physician and/or the brace's tension level may be adjusted to within a range prescribed by the physician.

In some embodiments, the brace may be used to assist in pumping blood back to the heart from one of the extremities (i.e., legs, arms, and the like), or used for pumping other fluids throughout the body. Sensors may be coupled with pneumatic pads, gel pads, and the like, that are tensionable and/or inflatable to provide local pressure and thereby force the blood or other fluids back toward the heart. The sensors may monitor the local pressure within the brace so that blood pumping assistance may be monitored. Such embodiments may be part of an edema management program to keep fluids flowing within the body and prevent fluids, such as blood, from pooling in a localized area. In a specific embodiment, the sensors may be part of a sock that the patient wears to assist in pumping blood back to the heart from the leg. In some embodiments, the motorized closure device may be replaced with nitinol wires or barrels/strips that wind around the brace and that are activated (i.e., electrified) to cause the wires to shrink and apply a local pressure to the brace and/or body part. In a specific embodiment, 80-100 such nitinol wires, and in a specific embodiment 90 wires, may function similar to a motorized closure device to assist in pumping blood back to the heart from the extremities of the body. One advantage of using the nitinol wires is that the brace and closure device may be significantly smaller than a similar brace using other closure devices. The nitinol wires may also be less noisy than conventional pneumatic or other closure devices and/or may allow for additional pressure zones to be created within the brace.

Having describe several embodiments of motorize closure devices and braces, additional details will become more evident with reference to the figures described below.

For convenience, the disclosure will focus mainly on braces, although it should be realized that the embodiments described herein (i.e., the closure device and/or other devices) may be used with virtually any type of apparel, garment, or other structure. For example, the embodiments (i.e., closure and other devices) may be used on shoes, boots, gloves, hats, medical devices, protective guards used in sports, and the like.

In addition, for convenience in describing the embodiments, the disclosure generally describes the devices, or components thereof, being closed via a reel or dial mechanism. The reel or dial mechanism typically closes the device, or components thereof, by tensioning a lace. As described herein, the dial is typically rotated to wind a lace into a spool. However, although the disclosure generally describes the closure devices, or components thereof, using a reel or dial mechanism, it should be realized that any tightening mechanism may be used and the disclosure is not limited to embodiments that only use a reel or dial.

Before describing specific details of the various embodiments, a general description of a brace and closure device or system will be provided. Referring to FIG. 1A, illustrated is an embodiment of an orthopedic brace 20. The orthopedic brace 20 generally comprises a knee brace that is tightened around a wearer's leg such that the knee brace substantially surrounds and protects the wearer's knee. Brace 20 may be tightened using a lacing configuration comprising two lacing systems 22a, 22b. The orthopedic brace of the illustrated embodiment is particularly concerned with relieving and/or supporting the knee joint. Although this illustrated embodiment shows the lacing systems applied to knee braces, it is to be understood that the principles discussed herein are readily applicable to any of a variety of orthopedic braces, including ankle braces, wrist braces, foot braces, elbow braces and many other types of orthopedic braces well known to those of skill in the art.

Figure 1B:
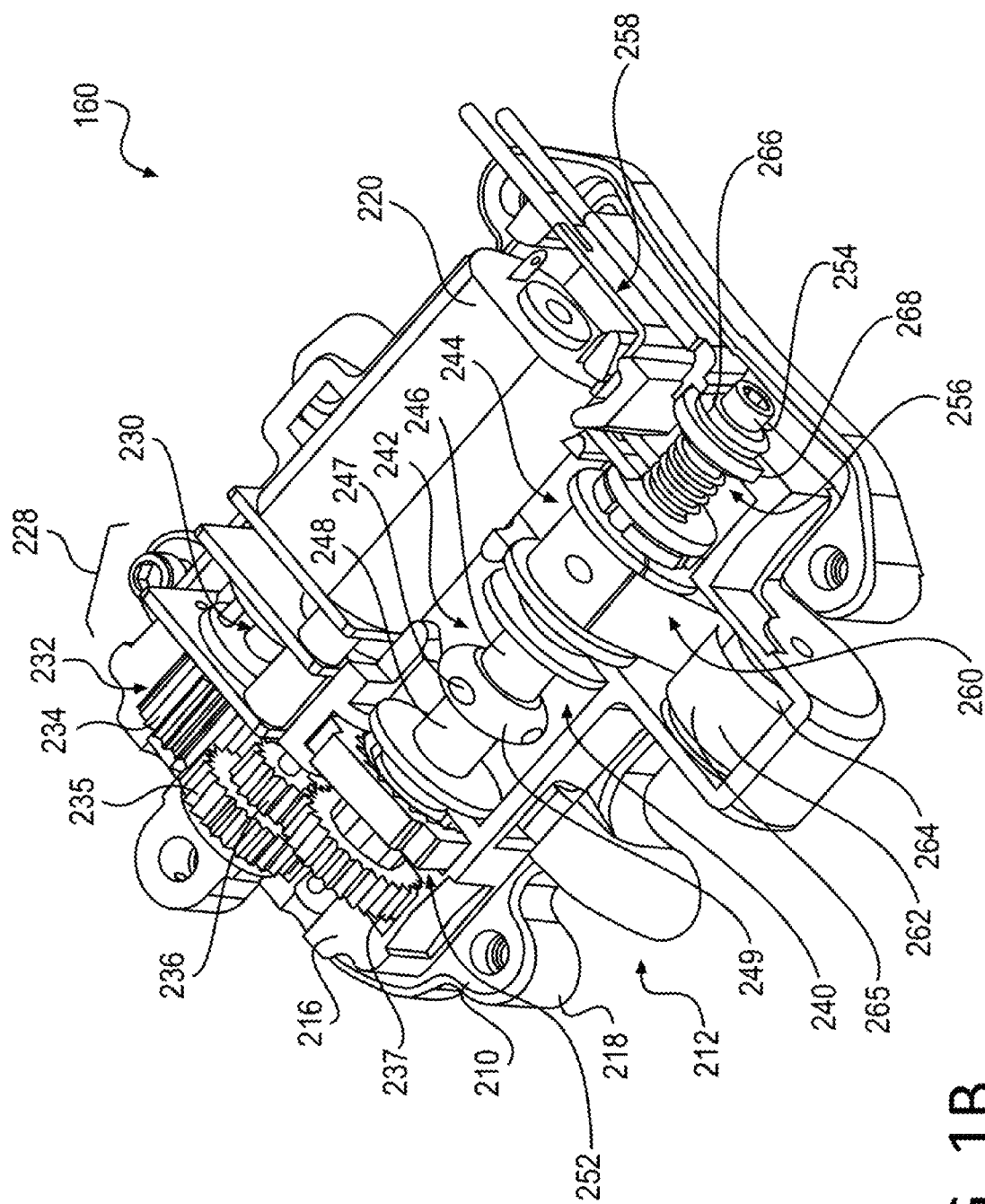

In some embodiments, the lacing configuration of closure system comprises two distinct lacing systems 22a, 22b. In some embodiments, each lacing system 22 includes a lace or cable 23 that is threaded through portions of the orthopedic brace and attached at opposite ends to a tightening mechanism 25 or reel, which includes a control such as a lever, crank or knob, which can be manipulated to retract the lace 23. FIG. 1A illustrates a manual tightening mechanism 25, or stated differently, a tightening mechanism that is operated via manual actuation of a component of the tightening mechanism (e.g., manual rotation of a knob). While FIG. 1A is provided to illustrate an embodiment of a brace fitted with a closure system, it should be realized that the embodiments described herein employ motorized closure devices that replace manual tightening mechanism, such as mechanism 25 of FIG. 1A. FIG. 1B illustrates an embodiment of a motorized closure system (hereinafter motorized tensioning device 160) that may be used in place of, or in addition to, tightening mechanism 25. The components of motorized tensioning device 160 are shown within a portion of a housing unit 212. Housing unit 212 may further include an inner housing portion 216 and an outer housing portion 218. Outer housing portion 218 may include a base panel 210 as well as an outer cover (not shown), and generally provides a protective outer covering for components of motorized tensioning device 160. Inner housing portion 216 may be shaped to support components of motorized tensioning device 160.

In some embodiments, motorized tensioning system 160 may comprise a motor 220. In some embodiments, motor 220 may be an electric motor. Examples of different motors that can be used include, but are not limited to: DC motors (such as permanent-magnet motors, brushed DC motors, brushless DC motors, switched reluctance motors, etc.), AC motors (such as motors with sliding rotors, synchronous electrical motors, asynchronous electrical motors, induction motors, etc.), universal motors, stepper motors, piezoelectric motors, as well as any other kinds of motors known in the art. Motor 220 may further include a motor crankshaft (not shown) that can be used to drive one or more components of motorized tensioning system 160. A battery or batteries is used to power motor 220 as is known in the art.

In some embodiments, motorized tensioning system 160 can include provisions for reducing the output speed of, and increasing the torque generated by, motor 220. In some embodiments, motorized tensioning system 160 can include one or more gear reduction assemblies and/or gear reduction systems. In one embodiment, motorized tensioning system 160 includes first gear reduction assembly 230 and second gear reduction assembly 232, which may be collectively referred to as gear reduction system 228. First gear reduction assembly 230 may be an in-line spur gear reduction assembly that is generally aligned with motor 220 and/or crankshaft (not shown). In contrast, second gear reduction assembly 232 may provide additional gear reduction that extends in a generally perpendicular direction to the orientation of the crankshaft. With respect to housing unit 212, first gear reduction assembly 230 may extend in a longitudinal direction of housing unit 212 while second gear reduction assembly 232 may extend in a lateral (or horizontal) direction of housing unit 212. By using a combination of in-line gears and horizontally spaced gears, relative to the orientation of the crankshaft, motor 220 can be arranged in parallel with a spool and corresponding spool shaft. This arrangement may reduce the longitudinal space required to fit all the components of motorized tensioning device 160 within housing unit 212.

Each gear reduction assembly can comprise one or more gears. In the exemplary embodiment, first gear reduction assembly 230 comprises one or more in-line spur gears. Moreover, first gear reduction assembly 230 may be driven by the crankshaft and itself drives a first gear 234 of second gear reduction assembly 232.

In one embodiment, second gear reduction assembly 232 may be configured with 4 stages of spur gears, including a first gear 234, a second gear 235, a third gear 236 and a fourth gear 237. In this embodiment, fourth gear 237 acts as a clamping gear for turning additional components of motorized tensioning device 160. The current embodiment of second gear reduction assembly 232 includes four gears. The number, type and arrangement of gears for gear reduction system 228 may be selected to achieve the desired tradeoff between size, torque and speed of the motorized tensioning system 160.

In some embodiments, motorized tensioning system 160 can include provisions for winding and unwinding portions of a lace. In some embodiments, motorized tensioning system 160 can include spool 240. In some cases, spool 240 may further comprise a first receiving portion 242 and a second receiving portion 244 for receiving a lace and a portion of a spring, respectively. Moreover, in some cases, first receiving portion 242 may comprise a first lace winding region 246 and a second lace winding region 248, which in some cases can be used to separately wind two ends of a lace. Since torque output goes down as the lace builds up in diameter, using separate winding regions for each lace end may help decrease the diameter of wound lace on spool 240 and thereby minimize torque output reduction. In some cases, first lace winding region 246 and second lace winding region 248 may be separated by a dividing portion 249, which may include a lace receiving channel 247 for permanently retaining a portion of the lace on spool 240. In other cases, however, first receiving portion 242 may comprise a single lace winding region.

Motorized lacing system 160 may include provisions for transferring torque between a final drive gear of second gear reduction assembly 232 and spool 240. In some embodiments, motorized lacing system 160 may include provisions for transferring torque from second gear reduction assembly 232 (or more generally from gear reduction system 228) to spool 240 in a manner that allows for incremental tightening, incremental loosening and full loosening of a lace. In one embodiment, motorized lacing system 160 may be configured with a torque transmitting system that facilitates the transmission of torque from fourth gear 237 of second gear reduction assembly 232 to spool 240.

The torque transmitting system may further comprise various assemblies and components. In some embodiments, the torque transmitting system may include a ratcheting assembly 252, a shaft 254 and a rotation control assembly 256. As discussed in further detail below, the components of the torque transmitting system operate to transmit torque from fourth gear 237 of second gear reduction assembly 232 to spool 240. More specifically, these components operate in a manner that allows for incremental tightening (spool winding), incremental loosening (spool unwinding) as well as full tension release (during which time substantially no torque is transferred from fourth gear 237 to spool 240).

In some embodiments, motorized tensioning device 160 may further include a secondary winding assembly 260. In some embodiments, secondary winding assembly 260 may be configured to apply torque to spool 240 independently of any torque applied by motor 220. In some cases, for example, secondary winding assembly 260 comprises a spring member 262 and a rotatable spring bearing 264. Spring member 262 may extends between second receiving portion 244 of spool 240 and spring bearing 264. In particular, a first end portion of spring member 262 may be associated with spool 240 while a second end portion 265 of spring member 262 may be associated with spring bearing 264. In operation, spring member 262 may be configured to apply a biasing torque that may tend to rotate spool 240 in the lace winding direction in the absence of other forces or torques (for example when there is slack in the lace). Spring member 262 could be a wind-up spring, a constant force spring, a constant torque spring, a clock spring as well as any other kind of spring.

Some embodiments can also include a fixed bearing 266, which may be associated with an end of shaft 254. In some embodiments, fixed bearing 266 may be received within a recess 268 of inner housing portion 216. In some embodiments, an end of shaft 254 may be disposed within an opening of fixed bearing 266, and may be configured so that shaft 254 can slide through the opening to provide some axial movement for shaft 254.

In some embodiments, motorized tensioning device 160 may include provisions for adjusting the operation of motor 220 according to one or more feedback signals. In some embodiments, for example, motorized tensioning device 160 may include a limit switch assembly 258. Generally, limit switch assembly 258 may detect current across portions of rotation control assembly 256 and vary the operation of motor 220 according to the detected current.

A brief overview of the operation of motorized tensioning device 160 is described here. A detailed description of the operation is given below. In an incremental tighten mode, motor 220 may begin operating in order to rotate the crankshaft. The crankshaft may turn an input gear of first gear reduction assembly 230, such that the output gear of first gear reduction assembly 230 drives first gear 234 of second gear reduction assembly 232. The intermediate second gear 235 and third gear 236 both rotate, which drives fourth gear 237 in the first rotational direction. As fourth gear 237 rotates, fourth gear 237 may engage and drive the torque transmitting system such that spool 240 may eventually begin to rotate in the first rotational direction. This causes lace to wind onto first receiving portion 242 of spool 240.

In an incremental loosen mode, motor 220 may operate to rotate the crankshaft. In the loosening mode, motor 220 and the crankshaft turn in an opposite direction of the direction associated with tightening. The gear reduction system 228 is then driven such that fourth gear 237 of second gear reduction assembly 232 rotates in the second rotational direction. In contrast to the incremental tighten mode, in the incremental loosen mode fourth gear 237 does not directly drive portions of the torque transmitting system and spool 240. Instead, the motion of fourth gear 237 in the second rotational direction causes the torque transmitting system to momentarily release spool 240, allowing spool 240 to unwind by a predetermined amount after which the torque transmitting system reengages spool 240 and prevents further unwinding. This sequence of releasing and catching spool 240 occurs over and over as long as fourth gear 237 rotates in the second rotational direction.

Finally, in an open or fully loosen mode, the torque transmitting system operates so that substantially no torque is transmitted to spool 240 from any components of the torque transmitting system. During this mode, spool 240 may rotate more easily in the unwinding direction about shaft 254 (for example, as a wearer manually loosens lace to take off a brace). As slack forms along the lace, secondary winding assembly 260 may apply a small amount of torque to second receiving portion 244 of spool 240, which acts to wind up slack in lace. A more detailed description of the motorized tensioning device 160 is provided in U.S. application Ser. No. 14/015,807, filed Aug. 30, 2013, entitled "Motorized Tensioning System for Medical Braces and Devices," the entire disclosure of which is incorporated by reference herein.

Referring again to FIG. 1A, as shown, the lace 23 may be threaded in a crossing pattern along a generally forward-facing portion of the brace 20, between two generally parallel rows of side retaining members or straps 40. In another embodiment, the lace 23 may be threaded or run laterally across the brace 20. The straps 40 may consist of a strip of material attached to the brace 20 so as to define a space in which guides 50 are positioned. The lace 23 slides through the guides 50 during tightening and untightening of the lace 23. A more thorough description of the brace 20 and lacing systems, 22*a* & 22*b*, is provided in U.S. Pat. No. 8,277,401, the entire disclosure of which is incorporated by reference herein.

The orthopedic brace 20 shown in FIG. 1A is constructed to fit a wearer's leg. The upper cuff 10 is formed to fit the wearer's thigh and curves around the thigh, generally conforming to the wearer's musculature. The lower cuff 12 is similar in construction to the upper cuff 10, and is formed to fit and curve around the wearer's calf. In some embodiments, the upper and lower cuffs 10, 12 are formed from a relatively lightweight, breathable material. In some embodiments, the cuffs 10, 12 are manufactured from a cloth, fabric, or foam-like material, or a thermoformable or non-thermoformable plastic material as would be well-known to those skilled in the art.

As shown, each of the cuffs 10, 12 are generally formed from a single piece of material that is wrapped around itself, forming two ends 32, 34 that are drawn towards each other and, in fact, may overlap. Although the ends 32, 34 are shown in an overlapping position, it should be understood that these ends might also be sized to be separated by some distance when the orthopedic brace 20 is tightened. Generally, the lace 23 may be tensioned to draw the ends 32, 34 past each other and thereby tighten the orthopedic brace 20 about the wearer's limbs. As is readily understood in the art, the two ends 32, 34 of brace 20 are designed to be open and fit about a patient's leg. The two ends 32, 34 are then positioned over the leg and brace 20 is tightened as described above.

Figure 2:
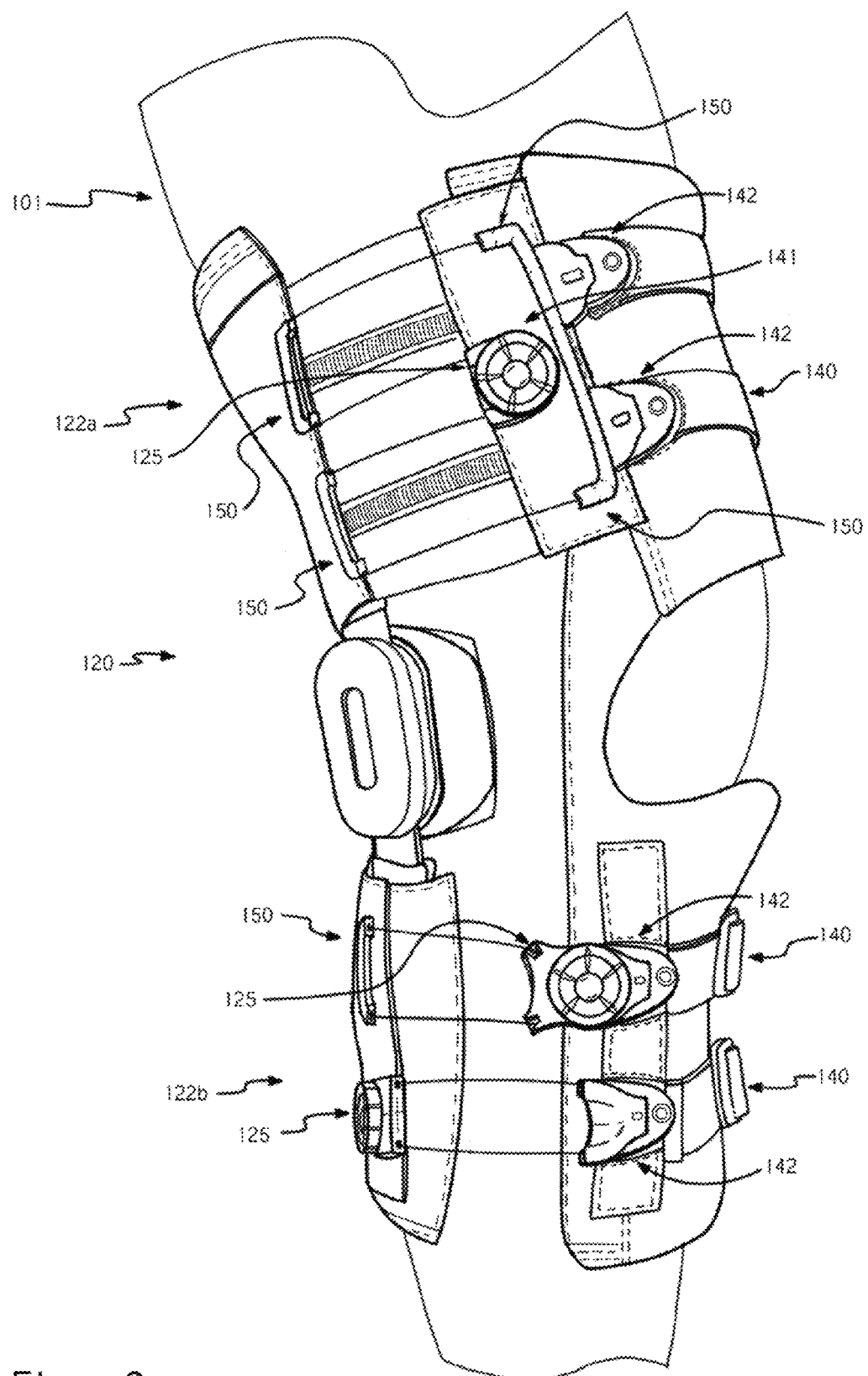
Figure 3:
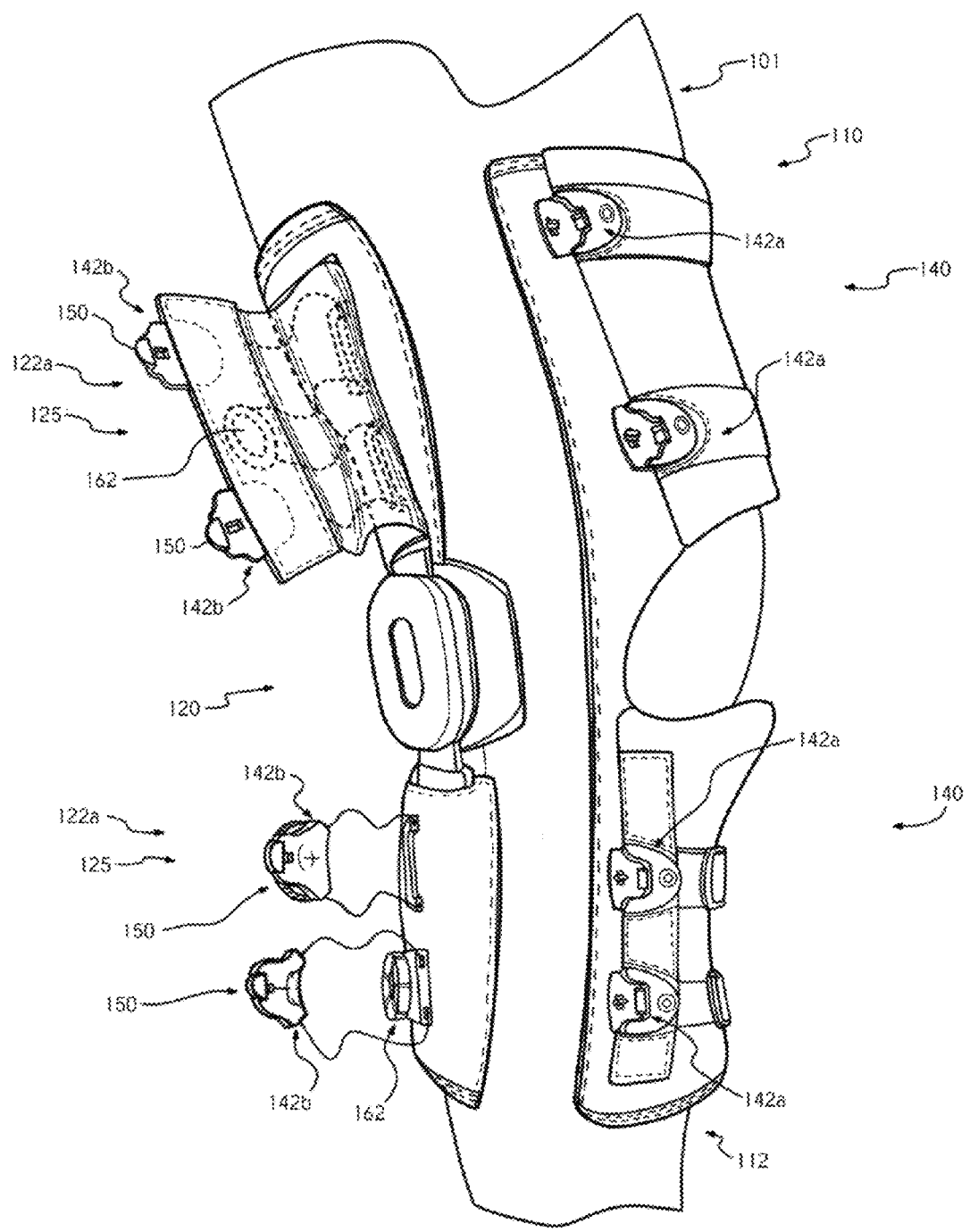

FIGS. 2 and 3 illustrate another brace 120 being fit over a wearer's leg 101. Brace 120 includes a closure system (e.g., 122a and 122b) that may include a motorized tensioning device 160, as described above. Brace 120 also includes a rough adjustment feature that permits further opening of the brace 120 to facilitate attachment of the brace 120 to a wearer's leg 101, while still providing the tightening mechanism 160 for final tightening. The rough adjustment feature may be variable length retaining members 140 that allow brace 120 to fit a wider variety of wearers' legs. In one embodiment, the variable length retaining member 140 includes adjustable straps. In other embodiments, a panel 141, such as those described herein, may be used. The panel 141 may be coupled with a tightening mechanism 160, such as a motorized system, to provide gross or macro adjustment of the brace 120. In some embodiments, retaining members 140 are configured to be releasably engaged with guides 150 opposite the tightening mechanism 160. The engagement may be by way of a quick release mechanism 142, for example the detachable guides described herein. In other embodiments, Fastex® buckles (shown), Velcro® or other similar mechanisms known to those of skill in the art may be used. As shown in greater detail in FIG. 3, each quick release mechanism 142 may include a female component 142a and a male component 142b that are coupled over the wearer's leg 101 to allow brace 120 to be donned and doffed. Exemplary embodiments of male and female components, 142b and 142a, are described in U.S. application Ser. No. 14/071,435, filed Nov. 4, 2013, entitled "Coupling Members for Closure Devices and Methods", the entire disclosure of which is incorporated by reference herein. In some embodiments, the female component 142 a may be attached to the guide 150 while the male component 142b is attached to the retaining member, though the arrangement of components may be switched as needed. The opposite end of the retaining member 140 may be attached to the brace such that tension in the lacing system 122 causes tension on the retaining member 140 when the quick released mechanism 142 is engaged, thereby compressing the cuffs around the wearer's limb.

Closure system 122 may include additional gross adjustment features in combination with the quick release mechanism 142 to provide a rough or gross adjustment of the closing pressure of the brace 120 prior to use of the tightening mechanism 125. For example, the closure system 122 may include ladder locks 144 (e.g., Fastex Slider®) which allow the retaining members 140 to be lengthened or shortened as needed. Though shown with two retaining members 140, as with the other embodiments disclosed herein in some embodiments, the number of retaining members 140 may vary. In some embodiments, three, four, five, six or more retaining members 140 may be desirable.

FIG. 3 shows one embodiment of the brace 120 in a partially open configuration. The quick release mechanism 142 have been disconnected leaving the guides 150 attached to the brace and releasing one end of the retaining member 140. To remove the brace 120, the user may then open the cuffs 110, 112 and slide the brace from the user's leg 101. Prior to releasing the quick release mechanism 142, the user may release tension in the closure system 122 by actuating the tightening mechanisms 160, for example, by pressing a release tension button. Alternatively, the user may release the tightening mechanisms 160 after releasing the quick release mechanism 142 to facilitate reattachment of the brace 120 by providing additional slack in the system without adjusting the retaining members 140 themselves.

Figure 4A:
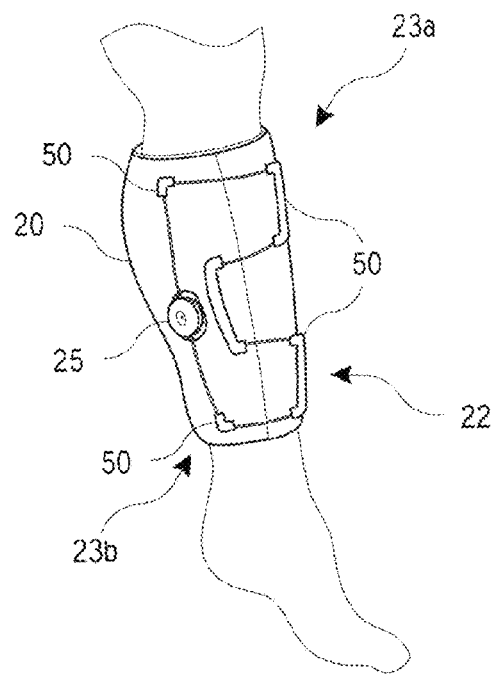
FIGS. 4A-C illustrate a lacing system that enables a brace to adjust to a flex of a user's limb.
Figure 4B:
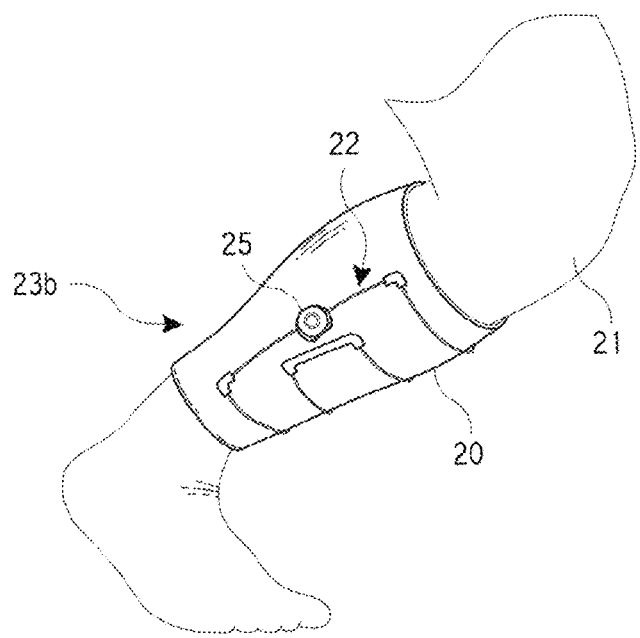
Figure 4C:
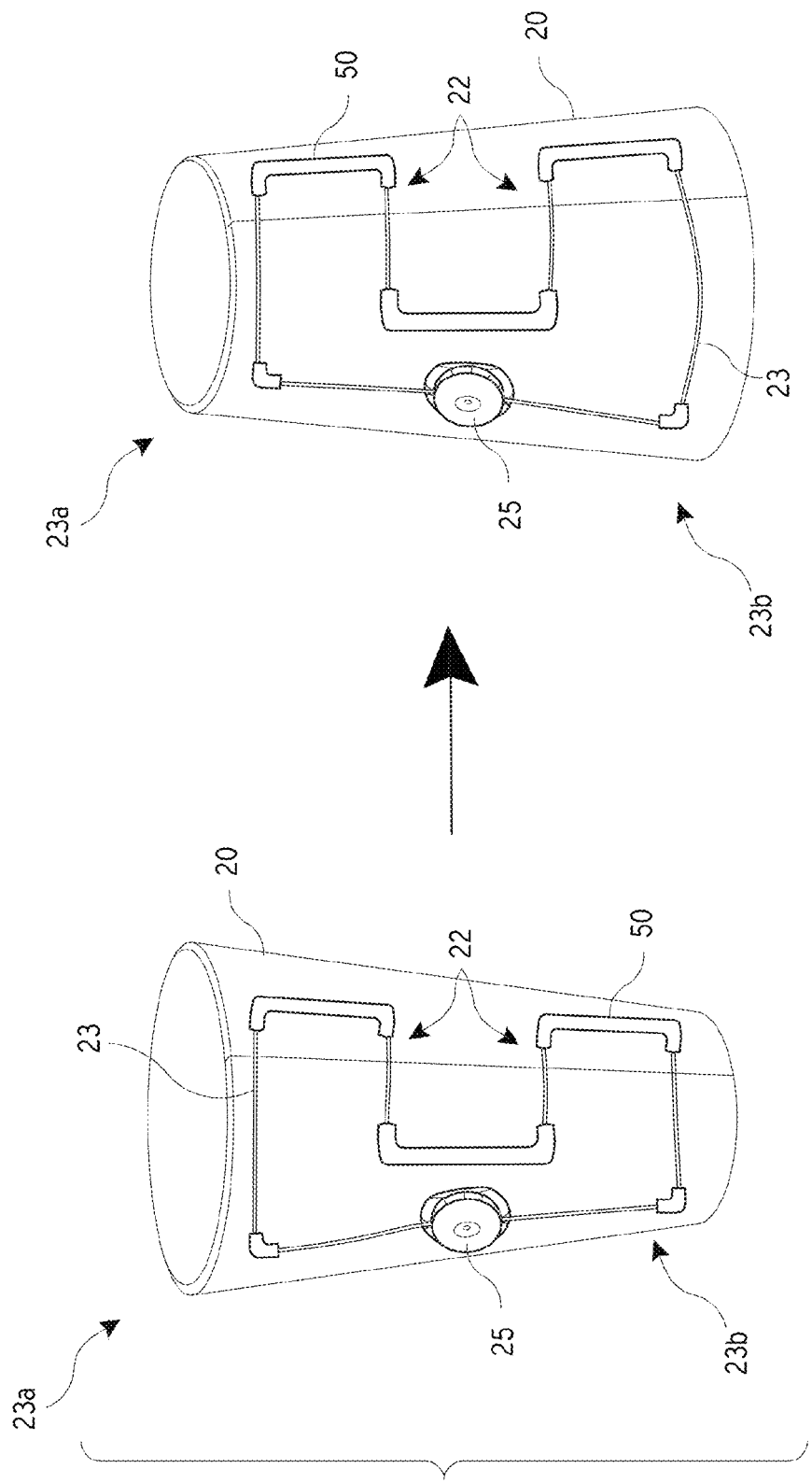

As shown in FIGS. 4A-C, one advantage of using the above described brace 20 is the increased ability of the brace 20 to fit a conical shape or an adjusting shape, such as a leg 21, arm, or any other body part of the patient. The ability of the brace 20 to fit a conical shape is provided by the lacing system 22. As the brace 20 is fit about a conical shape (e.g., the leg 21) and the lace 23 wound via the reel 25, and preferably motorized tensioning device 160, an upper portion 23a of the brace 20 contacts the conically shaped object. As the lace 23 is wound, the lace 23 adjusts until the lower portion 23b of the brace 20 also contacts the conically shaped object (e.g., the leg 21). Additional winding of the lace 23 will result in an approximately equal tension throughout the lace 23, which provides a relative even pressure on the conically shaped object. As such, the brace 20 fits well on a conical shape.

Similarly, the brace 20 is able to adjust to changes in the shape of the object, such as changes in the shape of a leg 21 (or other body part) due to flexing and/or relaxing of the muscle. For example, as leg 21 is flexed and assumes a more cylindrical shape, the lace 23 is able to slide within, or relative to, the guides 50 so that a bottom portion 23b of the brace opens or widens as a top portion 23a contracts or shrinks Conventional braces typically do not adjust in this manner and as such, when a patient flexes their leg 21 (or other body part) the brace 20 is typically forced to move or migrate, such as downward against the knee or ankle. In the embodiments described herein, because the lace 23 is able to slide relative to the brace 20 and guides 50, and the brace 20 is able to adjust to changes in shape, the fit or hold of the brace about the body part is increased and the migration of the brace 20 is limited or eliminated.

Figure 5A:
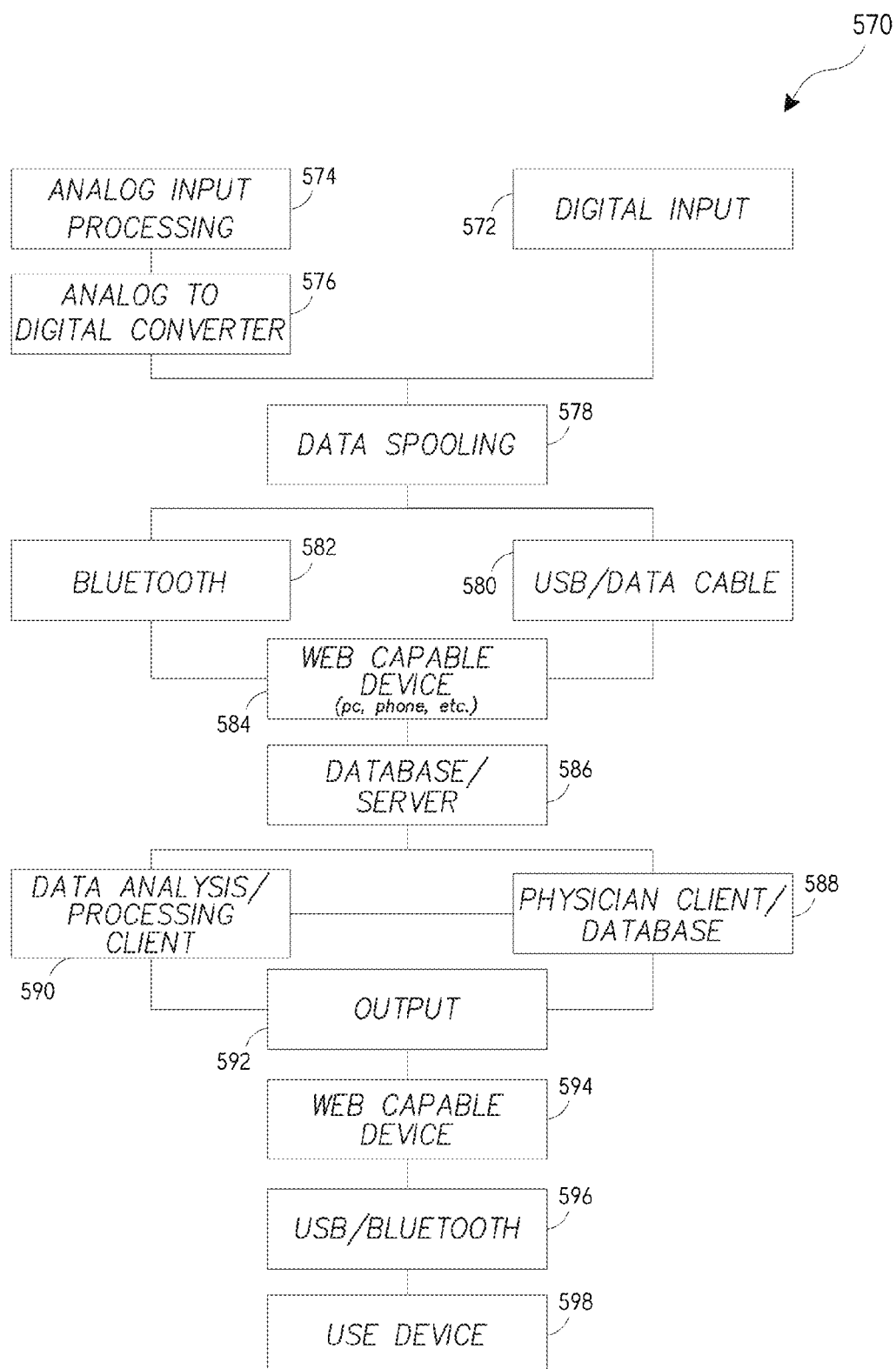
FIGS. 5A-C illustrate various embodiments of communicating information to a control unit of a brace and/or tracking data with the control unit.
Figure 5B:
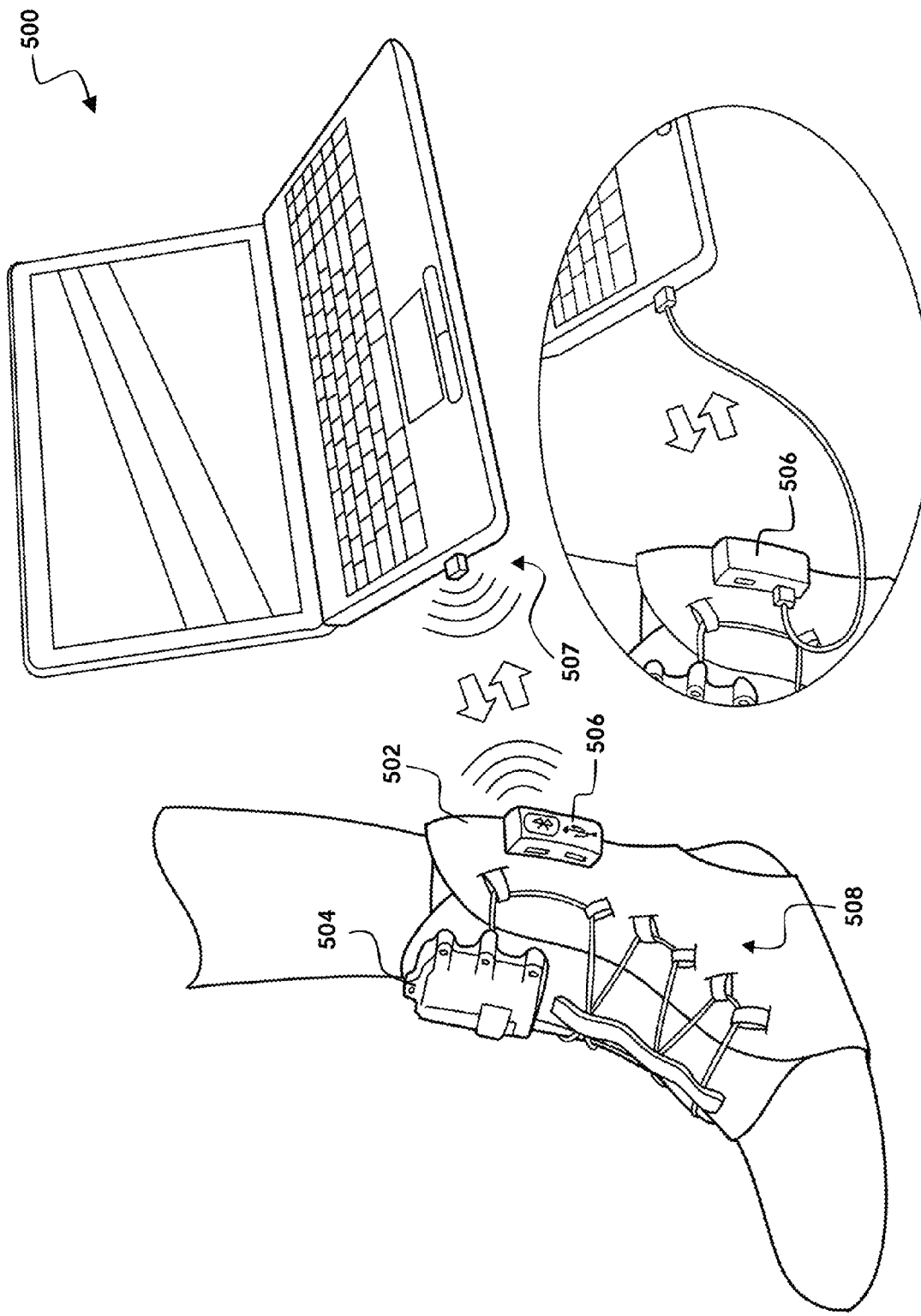

Referring now to FIGS. 5A-F, illustrated are various embodiments of a brace and a motorized closure device. FIG. 5B illustrates a first embodiment 500 of a brace 502 having a motorized closure device 504 that is configured to tension lace 508 to close brace 502 about a patient's limb, such as an ankle as shown. Motorized closure device 504 includes a spool (not shown) around which the lace 508 is wound as previously described. An electric motor (not shown) is coupled to the spool, either directly or via one or more gears (not shown), to automatically wind the lace 508 around the spool. Motorized closure device 504 responds to inputs that are provided by a user or provided according to one or more programmed therapies or therapeutic regimens. The programmed therapies may be input and or adjusted by a physician as described herein.

As shown in the method 570 of FIG. 5A, the inputs may be digital signals 572 or analog signals 574 that are subsequently converted to digital signals 576 via a digital converter. In some embodiments, motorized closure device 504 may include a control unit having a memory device and processor that are configured to store inputs that are to be immediately or subsequently implemented. Stated differently, in some embodiments, most of the electronic components may be located somewhere other than motorized closure device 504 so as to minimize the overall size of motorized closure device 504. The processor and memory device of motorized closure device 504 may be relatively small and configured to receive and store only those inputs that are to be immediately implemented such that the programmed therapy is stored on a different and larger memory device. This may be referred to as data spooling 578.

In some embodiments, the program therapy may be stored on another device 506 that is attached to the brace or positioned elsewhere. Device 506 may be a control unit that is communicatively coupled with the motorized closure device 504 and that is configured to communicate instructions thereto, such as a tighten instruction, loosen instruction, and the like. Device 506 may include an input mechanism that allows inputs to be provided to device 506. For example, in some embodiments device 506 may include a communication port 580 (e.g., USB port and the like), a wireless transmitter 582, and the like that allows device 506 to send and receive data to an external computing component 584, such as a laptop 507, tablet 509, mobile device, smart phone, and the like. In other embodiments, data, such as the programmed therapy or prescribed therapeutic regimen, may be stored on an external database or server and may be transmitted to device 506 as described above. Device 506 may monitor the tension of brace 502, the number of times brace 502 is donned and doffed, tension parameters as applied by the patient, the patient's compliance with a prescribed therapy, and the like. This information may be transmitted to an external computing device 586 via device 506 for subsequent review by a physician 588, or by a data analysis or processing program 590, and the like. The analysis or results from the analysis may be output 592 to a web capable device 594 via a wired or wireless transmission 596. The usage of the device 598 may then be monitored or a program or therapeutic regimen may be updated as described herein.

Motorized closure device 504 may also include a user interface (not shown) that is configured to display information to the patient. For example, the user interface may display the applied tension, the prescribed therapy, the tension range within which the patient may tension the brace, and the like.

Figure 5C:
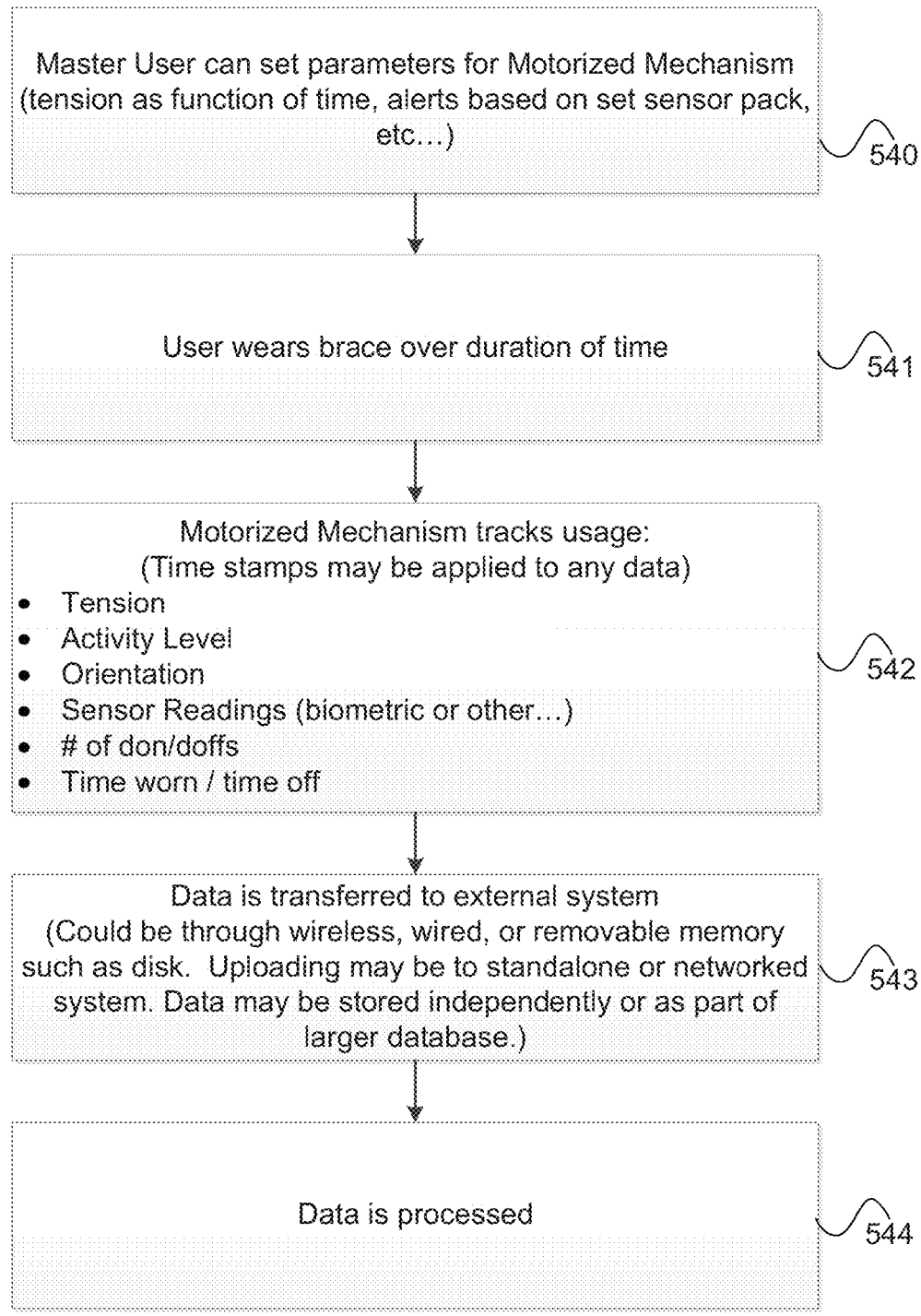

FIG. 5C illustrates motorized closure device 504 and device 506 being used to measure and transmit data as described herein. Specifically, at block 540, a master user can set parameters for the motorized closure device 504. The parameters may include tension as a function of time, alerts based on set sensor pack, and the like. The parameters may be set by the user, by a physician, and the like. Additionally, as described herein, the parameters may be prescribed or part of a therapeutic regimen to be implemented for the brace. At block 541, the user or patient wears the brace over a duration of time. At block 542, the motorized closure device 504 and/or device 506 tracks the patient's usage of the brace, such as a compliance with a prescribed therapy, the tension applied, any swelling or atrophy of the limb, a number of times the brace is donned and doffed, time of use (i.e., time worn and time off), an activity level, an orientation, and the like. A time stamp may be applied to any and/or all the data. At block 543, the information is transmitted to an external system or device and may be stored thereon, such as a centralized database. The data may be transmitted via Bluetooth, data cord, USB, and the like. At block 544, the data may then be analyzed by a physician or the patient to determine a compliance level, a level of healing, effectiveness of a prescribed therapy, and the like. In some embodiments, the data may be collected along with similar data from other patients to determine an overall effectiveness of a therapy and/or analyzed to determine additional therapies or improved therapies that may be prescribed to patients. A physician may then reconfigure or adjust a prescribed therapy, which is then transmitted back to device 506 for subsequent implementation, or the physician may allow the brace to continue to be worn as prescribed.

In some embodiments, the brace may include multiple motorized closure devices. For example, the brace may include a first motorized closure device that is used to tension a first zone of the brace and may include a second motorized closure device that is used to tension a second zone of brace. In this manner zonal tensioning of the brace may be provided. A battery pack of the motorized tensioning device may also be charged in various manners. For example, in some embodiments, the device's battery may be charged by placing the brace on an inductive coupling pad. The brace may include an inductive coupling unit that allows the brace to be charged by placing the brace on the inductive coupling pad. In some embodiments, resonant inductive coupling may be used to allow the distance between the inductive coupling pad and brace to be increased.

In another embodiment, the brace may include a charging unit that may be plugged into an electrical outlet. In yet another embodiment, the brace may include a battery pack that may be removed from brace and plugged into an electrical outlet for charging. Multiple battery packs, (e.g., a first, second, and/or third battery pack) may be used with brace so that electrical power is always provided to brace.

Figure 5D:
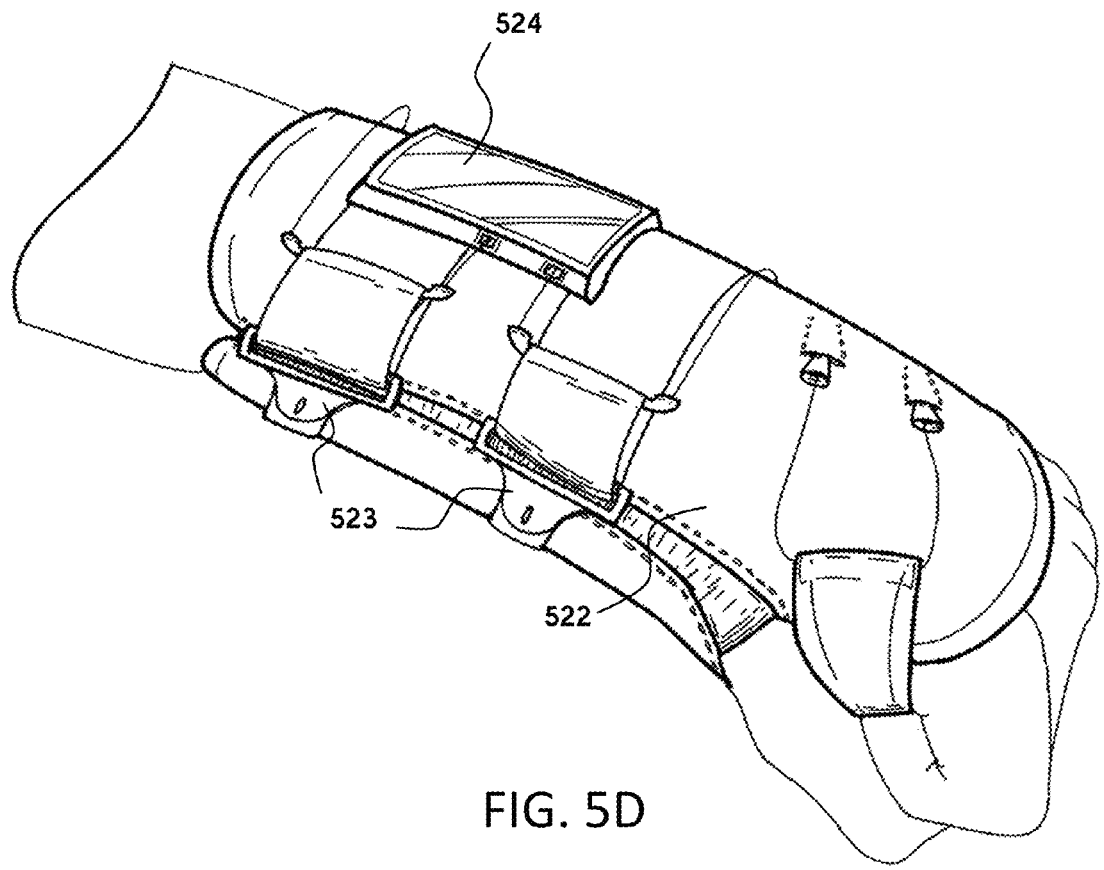
FIGS. 5D-E illustrates an embodiment of a user interface of a brace.
Figure 5E:
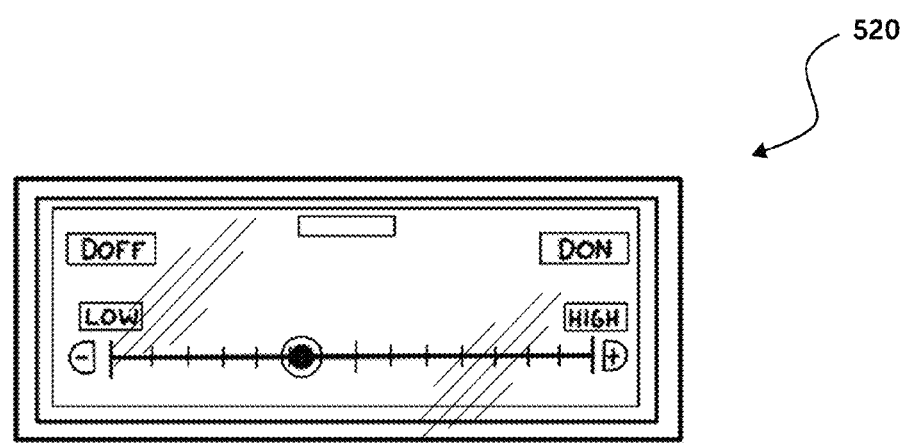

FIG. 5D illustrates another embodiment of a brace 522 that is fit about a patient's wrist. Brace 522 includes a motorized closure device 524 as previously described. Motorized closure device 524 is configured to tension lace as previously described. In some embodiments, the lace closure system may include a male and female components 523 as described in the '435 application previously incorporated herein. FIG. 5E illustrates an embodiment of a user interface 520 of motorized closure device 524. User interface 520 may be configured to show the tension applied to brace 522 and/or may include an electronic button or switch that is selected when the user wishes to don or doff the brace. Selecting the button or switch may automatically open or close the brace 522 about the patient's limb. User interface 520 may also include a slide control that allows the patient to quickly and easily adjust the tension applied to brace 522 via motorized closure device 524. User interface 520 may have various controls that may be used by the patient to adjust the tension applied to a brace. For example, in some embodiments a patient may slide his or her finger a long a linear slide control to increase or decrease the tension of the brace. In another embodiment, the patient may slide his or her forefinger around a curved slide control to increase or decrease the tension of the brace. Any other configuration of a slide control could likewise be used.

In some embodiments, the motorized closure device 504, or some other component (e.g., device 506), may include other components that are used to automatically tension the brace in accordance with one or more sensed conditions. For example, the motorized closure device 504 may be coupled with an accelerometer that is used to determine an acceleration of the body part or limb about which a brace is placed. If the accelerometer detects swift motions of the body part, motorized closure device 504 may be configured to quickly tension the brace about the body part to provide additional support to the body part. In this manner, the body part may be protected against sudden impacts that may result from falling, running, or other quick movements. In some embodiments, the motorized closure device 504 may be replaced with a nitinol device that is configured to quickly tension the brace by applying an electrical signal to a nitinol wire as described herein.

Figure 5F:
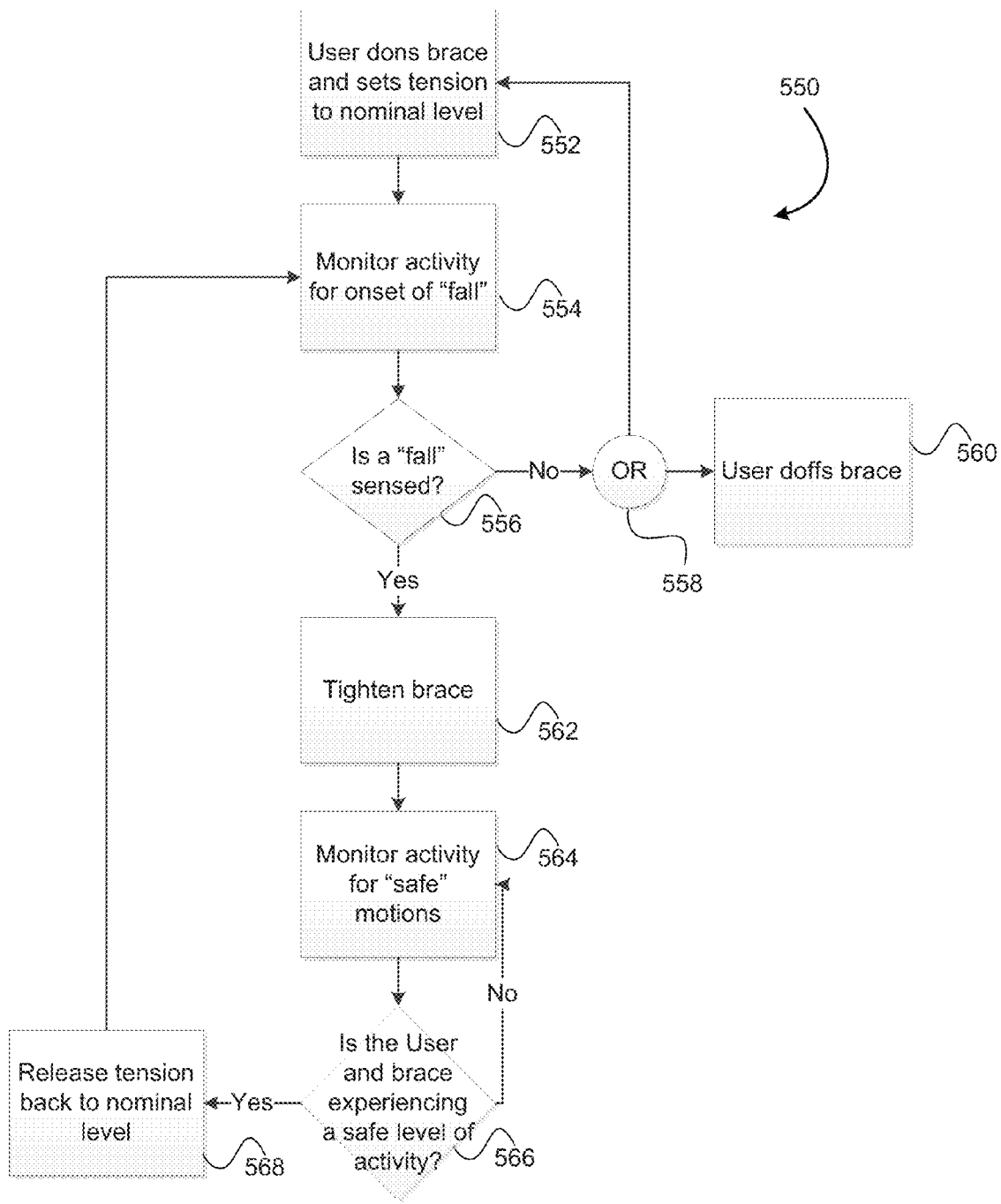

Referring now to FIG. 5F, illustrated is a method 550 of automatically tensioning a brace in response to a sensed condition, such as a fall. The automatic tensioning may be triggered via an accelerometer or some other sensor that is configured to sense the condition. At block 552, a user dons a brace and the brace tension or tightness is set to a nominal level, which may be input by the user or set according to a prescribed tightness value or therapeutic regimen as described herein. At block 554, the control unit (e.g., device 506) monitors activity for onset of the condition, such as a fall. A determination (i.e., 556) is made about whether the condition is sensed. The control unit continues to monitor the activity (e.g., block 554) if the condition is not sensed. Alternatively, at 558, the user may doff the brace (block 560), which resets the control unit.

If the condition is sensed, the process continues to block 562 and the motorized closure device 504 is triggered to tighten the brace and thereby protect the enclosed limb. The brace may be tightened by a predetermined amount (e.g., 2-5 lb pressure and the like) to stiffen the brace or otherwise protect the limb. At block 564, the control unit monitors the activity to determine if the user and/or brace are experiencing a "safe" level of activity, such as by detecting an absence of acceleration for a given period of time (e.g., 5 seconds, 2 seconds, and the like). In other embodiments, the control unit may monitor pressure and/or a stiffness of the brace to determine if a safe activity level is present. At 566, if a safe activity level is not detected, the control unit continues to monitor the activity. Alternatively, if a safe level of activity is detected, the process continues to block 568 and the motorized closure device 504 is triggered to release tension on the lace back to a nominal level.

Figure 6A:
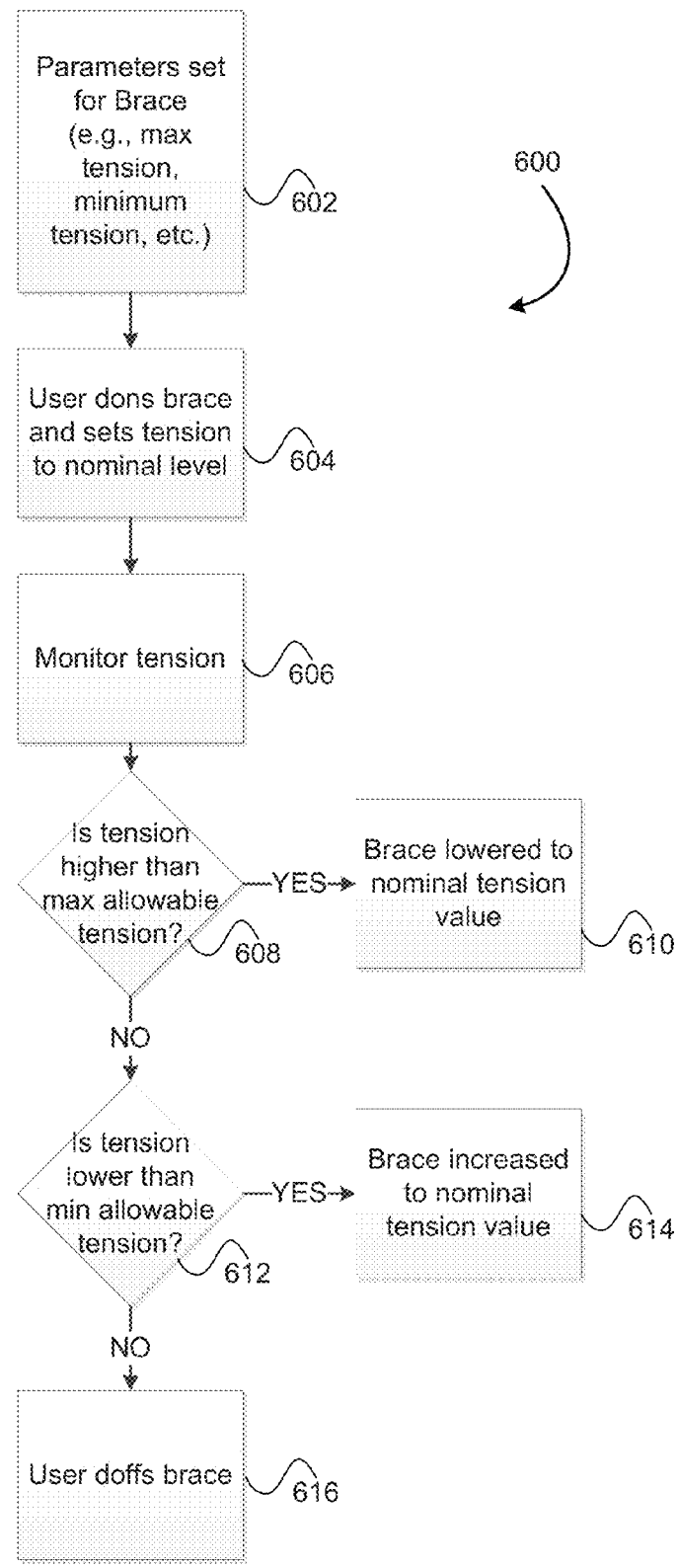
Figure 6B:
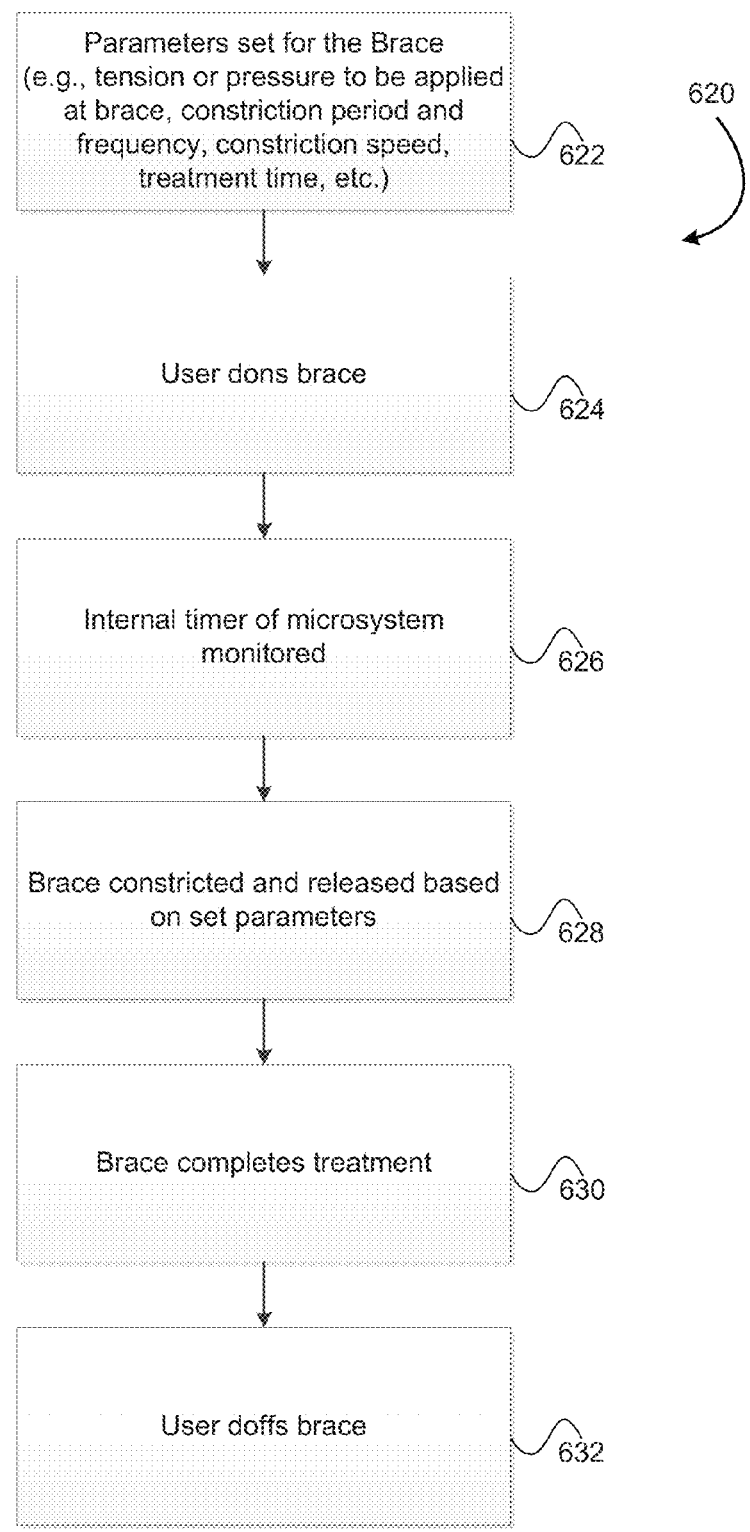
Figure 6C:
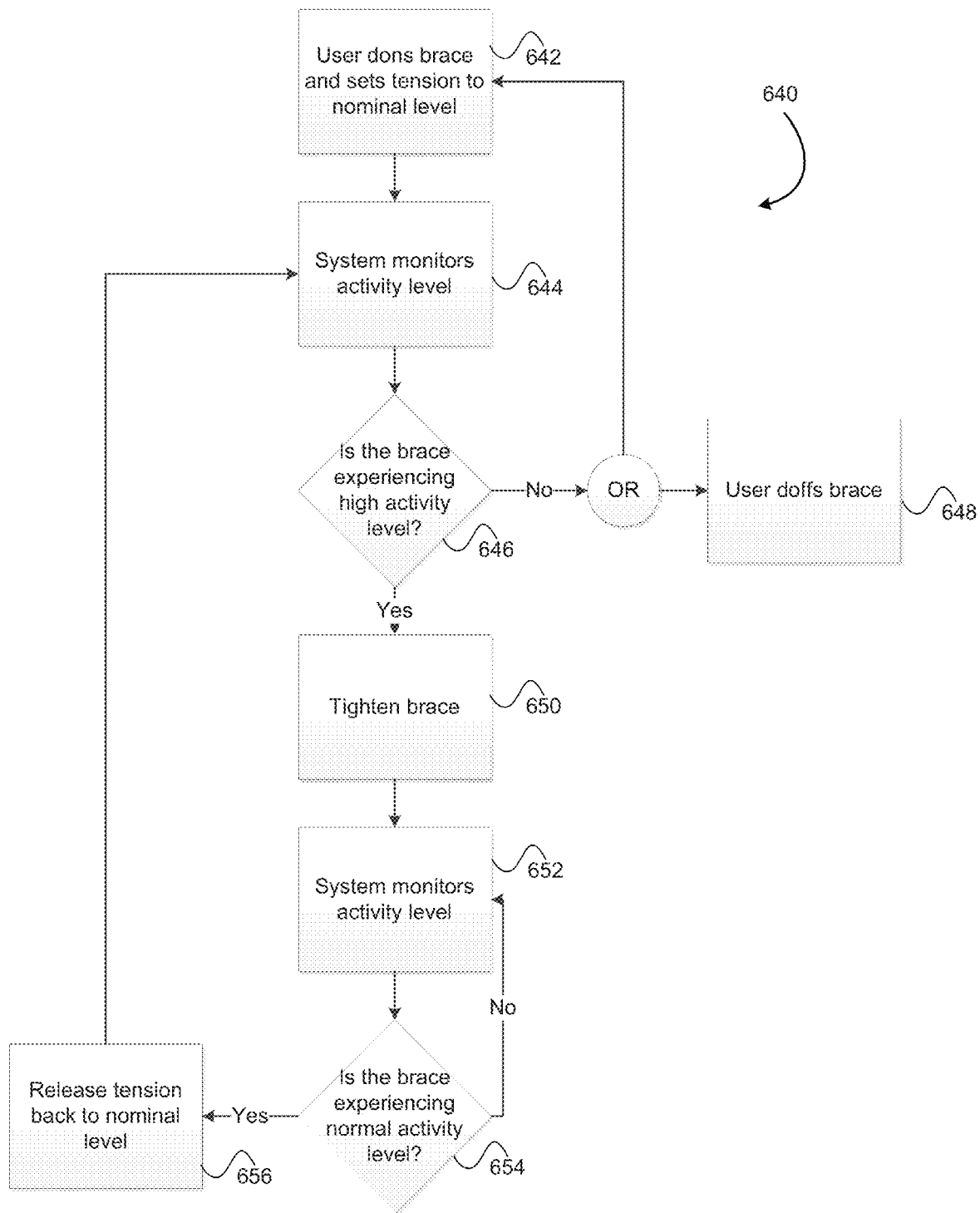

Referring now to FIGS. 6A-C, illustrated are embodiments of auto tensioning a brace. FIG. 6A illustrates a method 600 in which a motorized closure system may measure or calculate a tension of the lacing system and/or a pressure applied to the limb to determine whether the lace should be tightened or loosened. For example, at block 602, parameters for the brace are set, which may include a pressure or tightness value or range to maintain for the brace, a maximum lace tension that is allowed, a minimum lace tension that should be maintained, and the like. The parameters may be set according to a therapeutic regimen for the user and the like. At block 604 the user dons the brace and the motorized device adjust the lace tension or brace tightness/pressure to a nominal level. At block 606, the lace tension is monitored via the motorized device or a control unit communicatively coupled thereto. If the lace tension and/or brace tightness/pressure is greater than the maximum allowable tension (608), the lace tension and/or brace tightness/pressure is automatically reduced at block 610 via the motorized device. The high lace tension and/or brace tightness/pressure may be due to compartment syndrome, general swelling, user error, and the like.

If the lace tension and/or brace tightness/pressure is not greater than the maximum allowable tension, then it is determined whether the lace tension and/or brace tightness/pressure is lower than the minimum desired lace tension and/or brace tightness/pressure (612). Lower lace tensions and/or brace tightness/pressure may be due to a reduction in inflammation, atrophy, user error, and the like. If the lace tension and/or brace tightness/pressure is lower than the minimum allowable tension, the lace tension and/or brace tightness/pressure is automatically increased to the nominal level at block 614 via the motorized device. As shown in FIG. 6A, the motorized closure system may be configured to maintain the lace tension and/or brace tightness/pressure within a defined range. At block 616, the user may doff the brace after a period of time.

FIG. 6B illustrates a method 620 in which lace tension may be adjusted sequentially to facilitated fluid flow or for various other reasons. For example, the motorized closure system may be programmed to increase lace tension and/or decrease lace tension at specified intervals in order to increase blood or fluid flow into or out of the limb. According to the method 620, at block 622, parameters for the brace are set, which may include a lace tension or brace pressure to be applied, a constriction period and frequency, a constriction speed, a treatment time, and the like. The parameters may be set according to a therapeutic regimen for the user and the like. At block 624 the user dons the brace and at block 626 an internal timer of the microsystem is monitored. The internal timer may be used to determine the treatment period and/or to determine when to constrict or apply brace pressure and release the pressure. At block 628, the brace is constricted and released in accordance with the set parameters to assist in pumping or moving blood into and/or out of the limb. At block 630, the treatment is completed and at block 632 the user doffs the brace.

In other embodiments, the lace tension may be adjusted when it is determined that the activity level of the patient will be either high or low such as during periods of wake or sleep. For example, the lace tension may be decreased in the evening hours corresponding to periods of time that the patient is typically inactive, and may be increased in the morning and daytime hours corresponding to periods of time that the patient is typically active.

FIG. 6C illustrates a method 640 of auto tensioning a brace based on if the patient is currently engaged in an activity requiring support of a body part by the brace. For example, if the patient is running or using the body part in a physical activity, the lace tension may be increased to provide additional support to the limb. Conversely, if the motorized closure device determines that the patient is currently inactive, the lace tension may be loosened to allow the brace to slightly open and provide increased comfort. At block 642, the user dons the brace and sets the tension to a nominal level, or conversely, the motorized device automatically tightens the brace to the nominal level and described herein. At block 644, the system (e.g., motorized device and/or control unit) monitors the activity level of the brace via pressure sensors, accelerometers, strain gauges, and the like.

At block 646, a determination is made regarding if the brace is experiencing a high level of activity that may require additional brace tightening. If the brace is not experiencing a high level of activity, the system continues to monitor the activity at block 644. Or if the user doffs the brace (block 648) the process is reset. If the brace is experiencing a high level of activity, the lace tension is increased and/or the brace is tightened at block 650 via the motorized tensioning device. The additional tightness provided at block 650 may be based on parameters programmed into, or otherwise provided, to the system. The additional tightness may be a single value or may be scaled to the level of activity. For example, the system may be programmed to increase the tightness between a low and high range depending on the level of activity measured, or the system may be programmed to have multiple levels of increasing tightness for increasing levels of activity.

At block 652, the system monitors the activity level of the brace. At block 654, a determination is made regarding if the brace is experiencing a normal level of activity. The "normal activity level" may be programmed into or otherwise communicated to the motorized device and may include an level of acceleration per given time period, an amount of pressure per time period, and the like. If the brace is not experiencing a normal level of activity (i.e., the brace continues to experience a high level of activity), the system continues to monitor the activity at block 652. If the brace is experiencing a normal level of activity, the lace tension and/or brace tightness/pressure is reduced at block 656 to the nominal level via the motorized tensioning device. The process then returns to block 644 in which the system monitors the activity level of the brace. The process is repeated until the user doffs the brace at block 648.

Figure 6D:
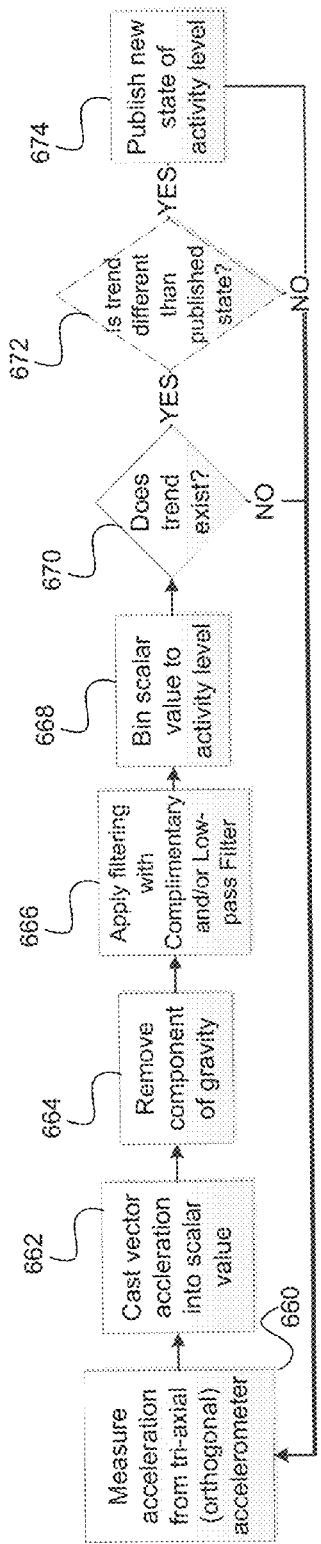

FIG. 6D illustrates a method of determining if an acceleration of the brace is sufficient to trigger tightening of a brace. At block 660, the acceleration of the brace is measured, such as from a tri-axial (orthogonal) accelerometer. At block 662, the vector acceleration is cast into a scalar value. At block 664, a component of gravity is removed if applicable. At block 666, filtering techniques are applied to the scalar value, such as a complimentary and/or low-pass filter. At block 668, the scalar value is related to an activity level. A determination is then may regarding whether a trend exists (670) and whether the trend is different than a published state (672). A negative response to either determination resets the process to block 660 while a positive response to both determinations results in setting of a new state of activity level (block 674).

Figure 6E:
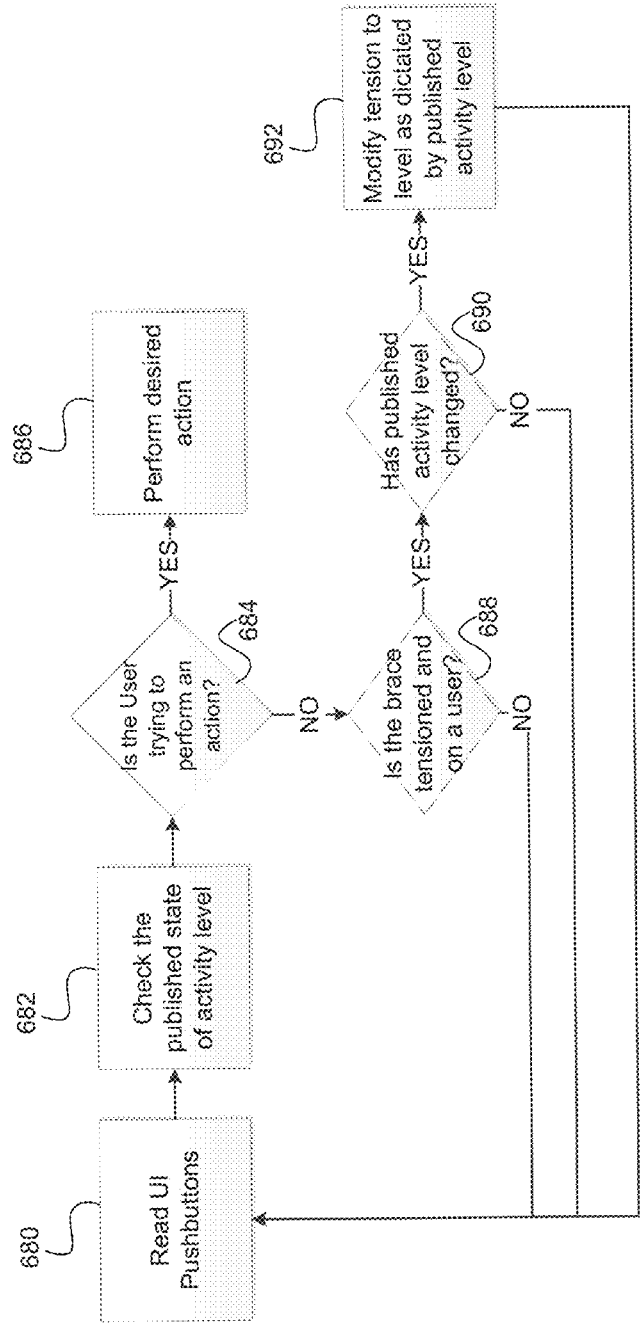

FIG. 6E illustrates a method of adjusting the fit of a brace based on the activity of a user. The method of FIG. 6E may be performed in response to a new state of activity level being published at block 674 of FIG. 6D or for various other reasons. At block 680, the system reads, monitors, or otherwise receives input from a pushbutton of a user interface. At block 682, the system checks the published state of activity level for the brace, which may be a nominal level, high level, low level, and the like. At block 684, a determination regarding whether the user is trying to perform an action is made. If the user is attempting to perform an action, the system performs the desire action at block 686 (e.g., tightens the brace, loosens the brace, performs a prescribed therapeutic regimen, and the like). If the user is not attempting to perform an action, a determination is made regarding whether the brace is tensioned and on a user (block 688). If the brace is tensioned and on a user, a determination is made about whether the published activity level has changed (block 690). If the published activity level has changed, the lace tension and/or brace tightness/pressure is modified to the level dictated by the published activity level. The system then resets to block 680. A negative determination at block 688 and/or 690 also resets the system to block 680.

Figure 7A:
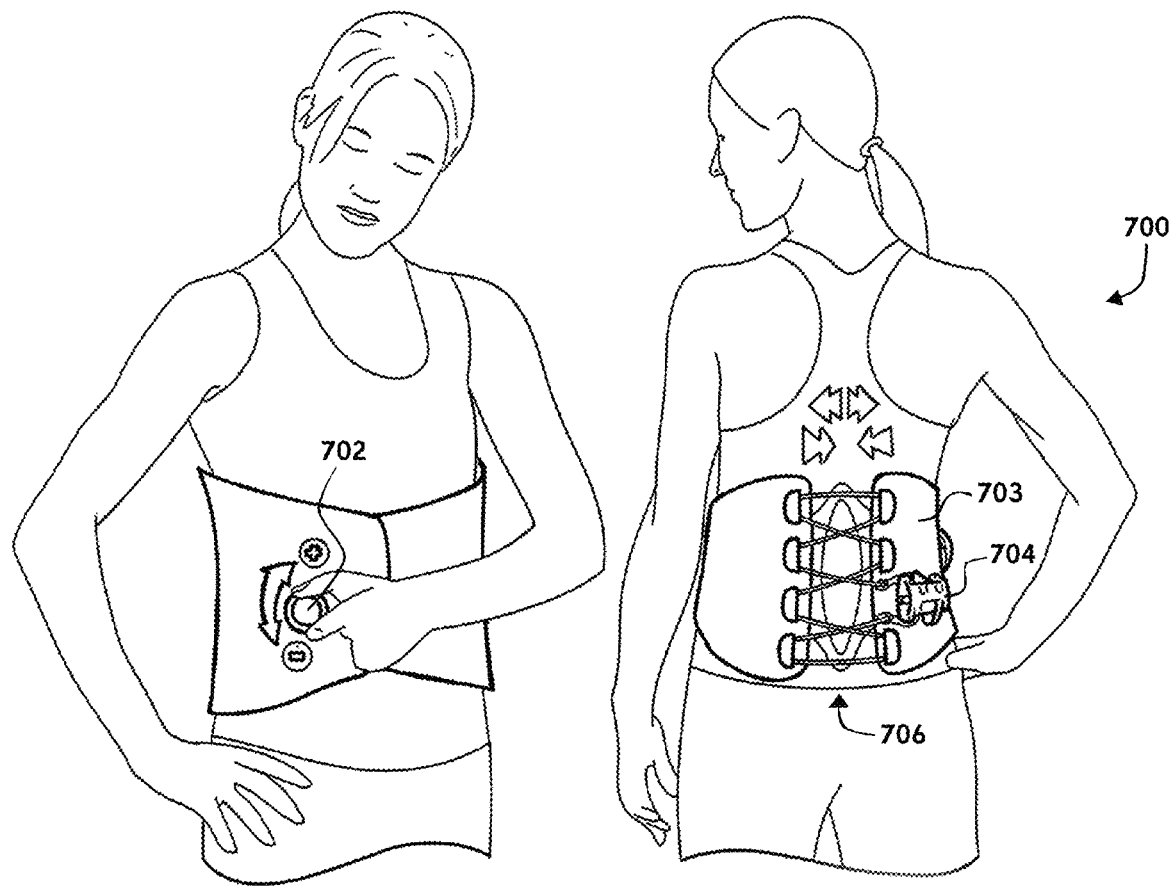
FIGS. 7A and 7B illustrates embodiments of control mechanisms that may be used to tighten a brace via a motorized tensioning device.

Referring now to FIGS. 7A-G, illustrated are embodiments of various ways in which tension may be adjusted with a motorized closure device. The tension adjustment mechanisms described in FIGS. 7A-G provide easy control for patients that may be disabled or otherwise dexterity challenged. FIG. 7A illustrates an embodiment 700 of a brace 703 having a motorized closure system 704 that is used to tension a lacing system 706 as described herein. As shown, brace 703 may be configured to fit around a waste of the patient. A dial 702 may be positioned on a front side of the brace to provide easy access to a patient. The patient may operate the dial 702 to increase and decrease the tension of the lace of lacing system 706 as desired. Dial 702 is communicatively coupled with motorized closure system 704 such that rotation of dial 702 provides manual input to the motorized closure system 704 to increase or decrease the lace tension.

Figure 7B:
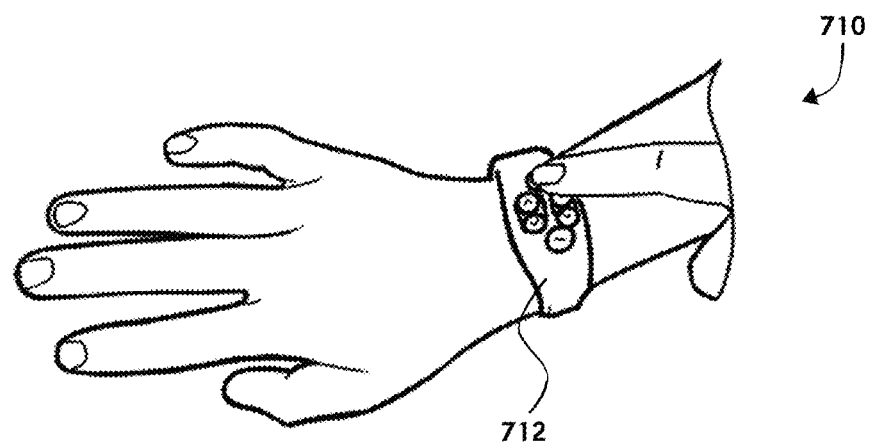
Figure 7C:
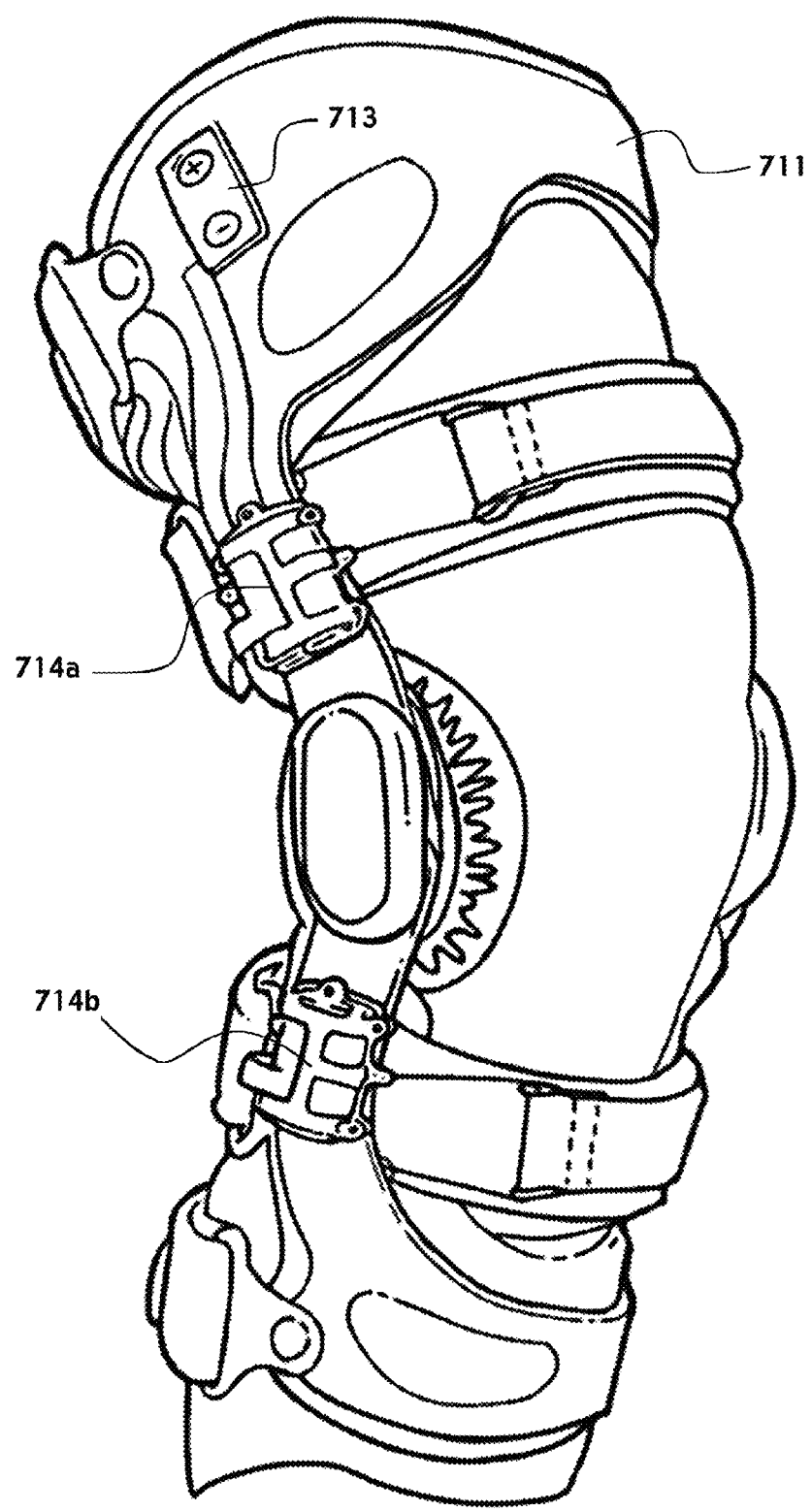
FIG. 7C illustrates a brace that includes multiple motorized tensioning devices to different separate zones of the brace.

FIG. 7C illustrates another embodiment of a brace 711 that is fit about a patient's knee. Brace 711 includes a first motorized closure system 714a and a second motorized closure system 714b. First motorized closure system 714a is configured to tension an upper region of brace 711 so that the upper portion of brace 711 presses against an upper region of the patient's leg and/or knee. Likewise second motorized closure system 714b is configured to tension a lower region of brace that so the lower portion of brace presses against a lower region of the patient's leg and/or knee. As shown in FIG. 7B, the patient may wear a wristband 712 that includes controls that allow the patient to independently tension first motorized closure system 714a and second motorized closure system 714b. The user's inputs may be wirelessly transmitted from wristband 712 to the respective first and/or second motorized closure systems, 714a and 714b.

Figure 7D:
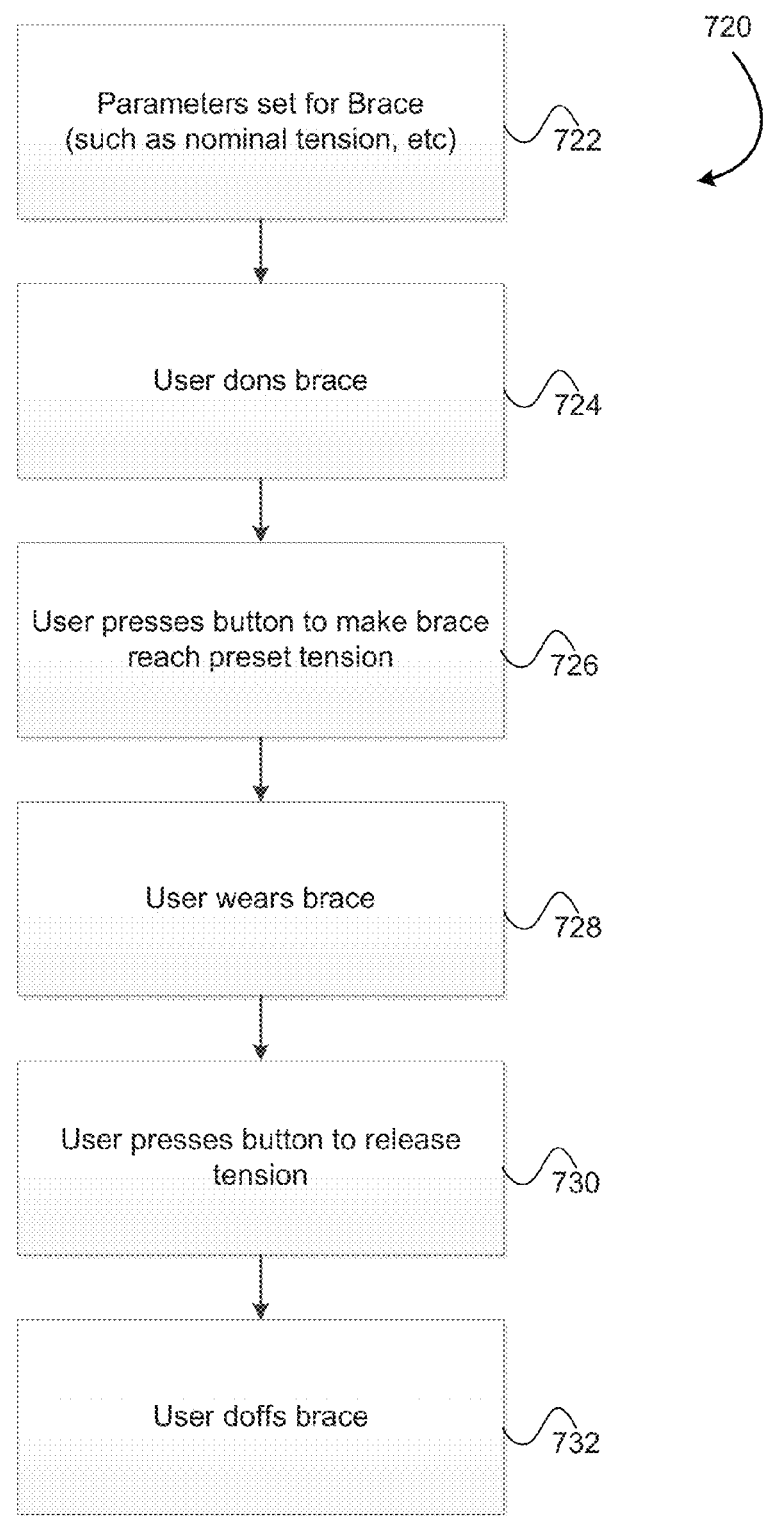
FIG. 7D illustrates a method for adjusting a tightness of a brace about a limb.

FIG. 7D illustrates a method 720 of controlling a brace's tightness or pressure with a control device, such as a wrist band, knob, and the like. At block 722, parameters are set for the brace, such as a nominal tension or brace tightness. At block 724, the user dons the brace. At block 726, the user activates a control (e.g., presses a button, rotates a knob, etc.) that triggers the motorized device to tighten the brace about the limb to the preset or nominal tension. At block 728, the user wears the brace. At block 730, the user activates a control (either the same control or a different control) that triggers the motorized device to decrease the tightness of the brace about the limb. At block 732, the user doffs the brace.

Figure 7E:
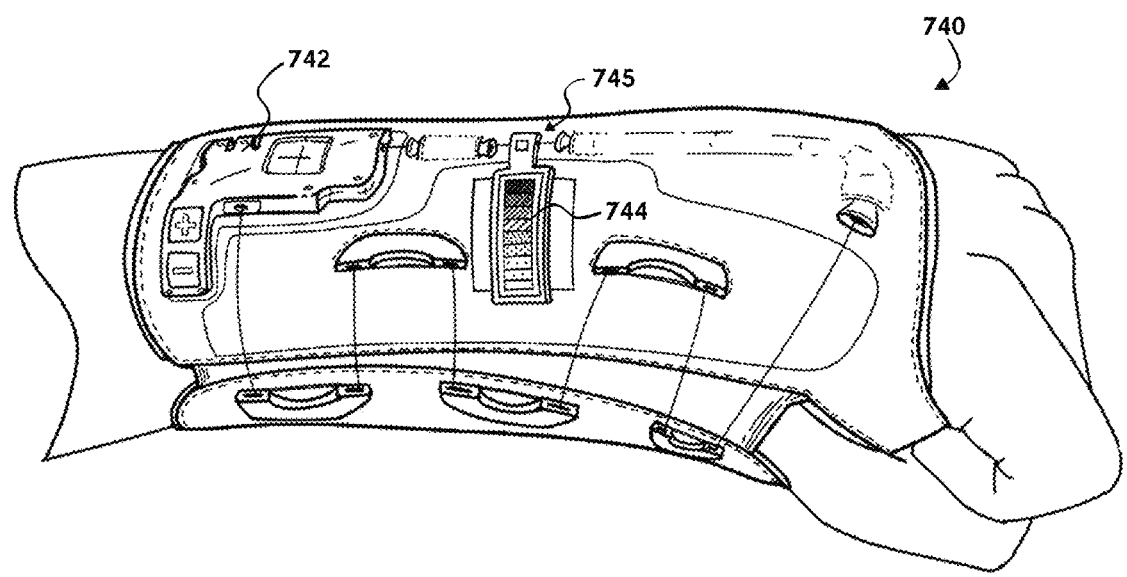
FIGS. 7E-G illustrate user interfaces that may be used to tighten a brace about a limb and/or to provide information to the user on the tightness of the brace about the limb.
Figure 7F:
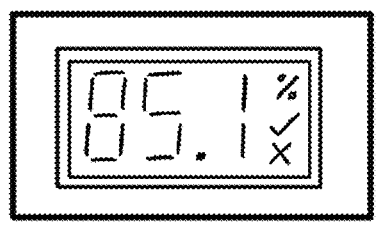
Figure 7G:
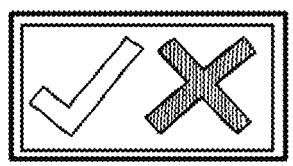

FIG. 7E illustrates another embodiment 740 of the brace that is fit about a user's wrist and that includes a motorized closure system 742 as described herein. The brace also includes a slide tension control 744 that is communicatively coupled with motorized closure system 742 to tension the lace and adjust the fit of the brace about the user's wrist. To tension the lace, the patient may simply place their finger on the slide tension control 744 and slide their finger towards one end of the control; likewise, the patient may slide their finger towards an opposite end of the control to loosen the lace. Slide tension control 744 may visually indicate the level of tension applied via motorized closure system 742 so that the patient is visually aware of the tension being applied to the body part. In some embodiments, slide tension control 744 may include indicia that visually displays when a proper amount of tension has been applied. The indicia may be as simple as a green checkmark that indicates a proper amount of tension, a red X Mark that indicates an insufficient or overly sufficient amount of tension (FIG. 7G), or the indicia may be more complex and/or include various shades of color from green to yellow to red that indicate a corresponding amount of tension. Alternatively, slide tension control 744, or some other component of the brace, may visually indicate a total amount of force applied or a percentage of a force applied in relation to a prescribed amount of force (FIG. 7F). In this manner, the patient may be able to visually determine if and when a proper amount of tension is applied. The slide tension control 744 may include a tension sensor 745 that connects or couples with the lace to measure the amount of tension in the lace.

The embodiments described above allow the brace to be closed in a repeatable manner and by a repeatable and measurable amount. Repeatable closure may be provided by measuring a tension force applied to the lace or by measuring a displacement of the lace. The embodiments described above are ideal for disabled and or dexterity challenged individuals. The controls of any of the above described embodiments may include a positive sign control button that corresponds to an increase in lace tension and a negative sign control button that corresponds to a decrease in lace tension.

Figure 8A:
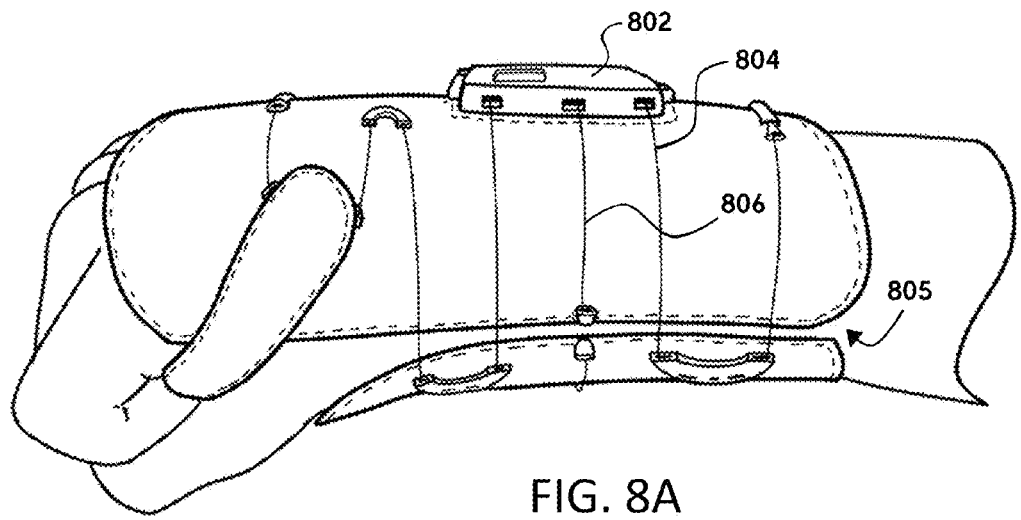
FIGS. 8A-H illustrate various embodiments of devices, systems, or controls that may be used to automatically open a brace to allow a patient to easily don or doff the brace.
Figure 8B:
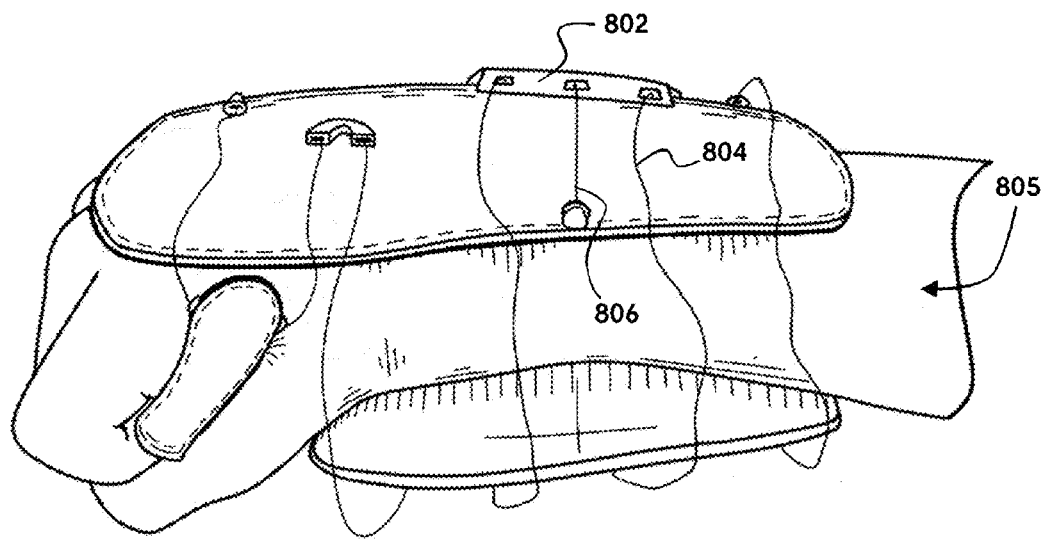

FIGS. 8A-H illustrate various embodiments of devices, systems, or controls that may be used to automatically open a brace to allow a patient to easily don or doff the brace. FIGS. 8A and 8B illustrate a first embodiment of a brace that includes a motorized closure system 802, such as those described herein. The embodiment also includes a first lacing system 804 and a second lacing system 806. The first lacing system 804 is used to tension the brace about the patient's body part as described herein. The second lacing system 806 is used to open the brace so as to allow the patient to place the brace over a body part, such as over a wrist as shown in FIGS. 8A and 8B. The first lacing system 804 may traverse across the brace and through one or more guides as described above such that when tension is applied to the lace, the brace closes about the patient's body part. The second lacing system 806 may be coupled with the brace on opposite sides of an opening 805 such that when tension is applied to the second lace, the opening 805 of the brace widens to allow the patient to easily place the brace over the body part.

Figure 8C:
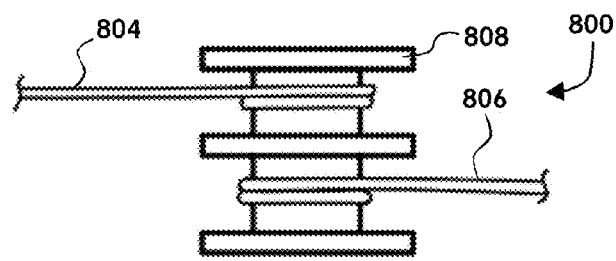

As shown in FIG. 8C, in some embodiments, the first lace 804 and second lace 806 may be wound around a single spool 808 positioned within the motorized closure system 802. Typically, each lace, 804 and 806, will be wound around a separate channel of the single spool 808. In this manner, winding of the spool causes one of the laces (e.g., lace 804) to wind around the spool 808 while the other lace (e.g., 806) unwinds from the spool 808. In such embodiments, tension is essentially always applied to the first lace 804 and/or the second lace 806 as the brace is opened and closed about the body part. This minimizes or eliminates tangling of either the first or second lace, 804 and 806, during donning and doffing of the brace and tensioning thereof. In other embodiments, the first and second laces, 804 and 806, may be wound around separate spools (not shown) that may be individually controlled to tension the first and second laces as desired.

Figure 8D:
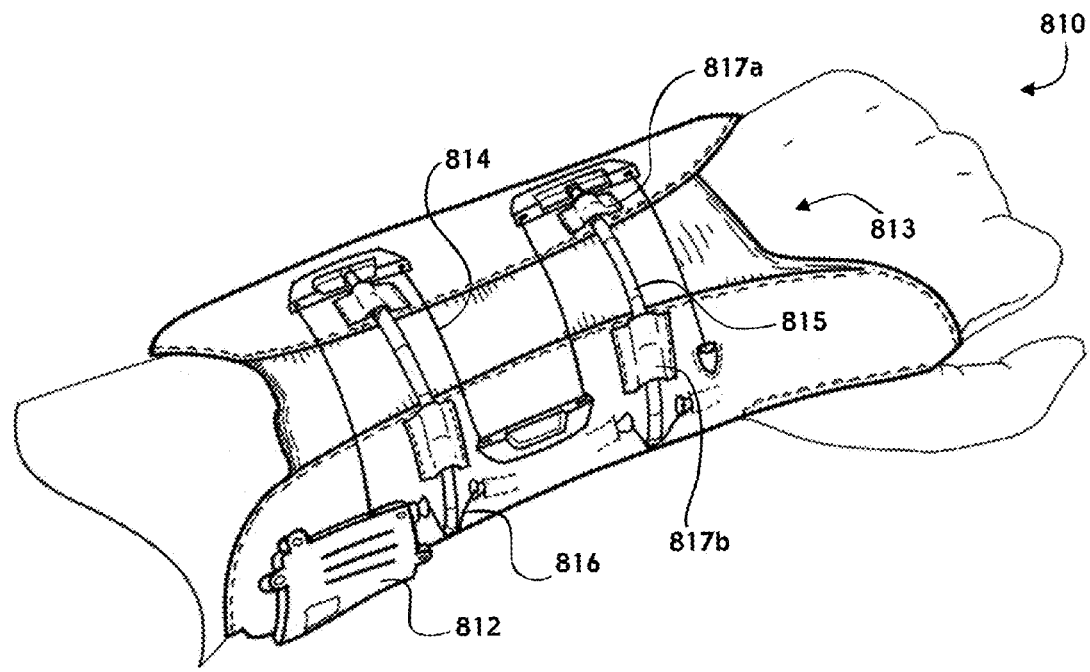
Figure 8E:
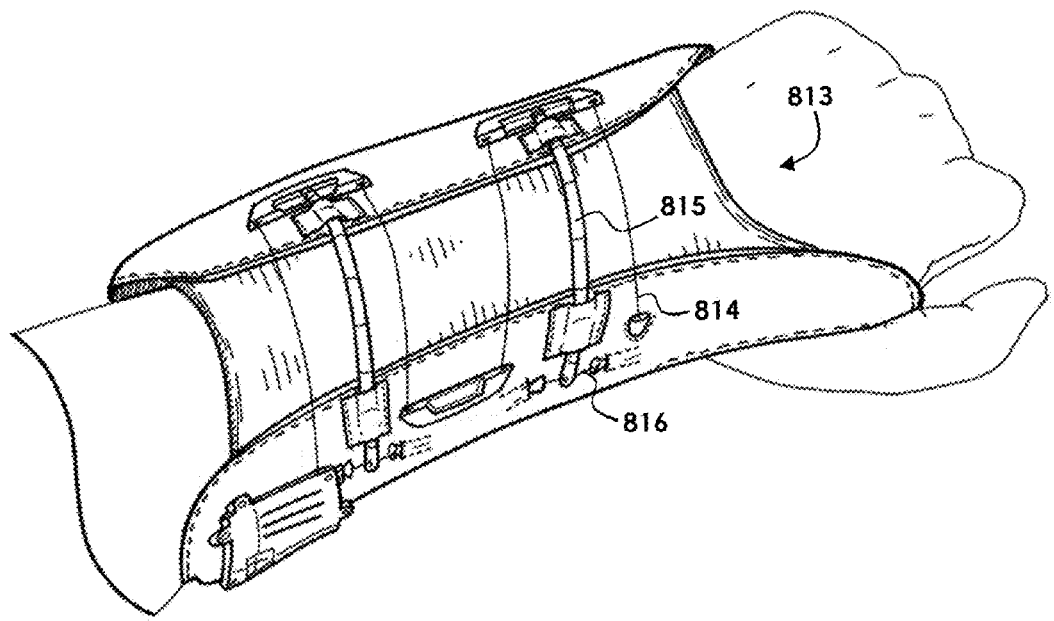

FIGS. 8D and 8E illustrate another embodiment 810 of a system for opening a brace. Like the embodiment of FIGS. 8A and 8B, embodiment 810 also includes a first lacing system 814 and a second lacing system 816 that are each coupled with a motorized closure system 812. The first lace 814 of the first lacing system is tensioned to close a gap 813 of the brace while the second lace 816 of the second lacing system is tensioned to open the gap 813 as previously described. Opening and closure of the gap 813 is performed via one or more rods 815 that span the gap 813. Each of the rods 815 is coupled at a distal end with one side of the brace and coupled at a proximal end with the second lace 816 such that tensioning the second lace 816 causes the distal end of the rods 815 to press on the side of the brace and thereby push the gap 813 open.

The rods 815 may be held in place relative to the brace via sleeves that are coupled with the brace. For example the distal portion of the rods 815 may be inserted through a first sleeve 817*a* and the proximal portion of the rods 815 may be inserted through a second sleeve 817*b* to hold the rods 815 in position relative to the brace. The rods 815 may slide relative to the first sleeve 817*a* and/or second sleeve 817*b* to allow the gap 813 to be pushed open as described above. In some embodiments, the distal portion of the rods 815 may be coupled with a guide around which the first lace 814 is positioned. Tensioning the first lace 814 causes the rods 815 to slide through at least one of the sleeves (e.g., 817*b*) and closes the gap 813. In some embodiments an opposite side of the brace may include a male and female components as described herein to allow the opposite side of the brace to be fully opened.

Figure 8F:
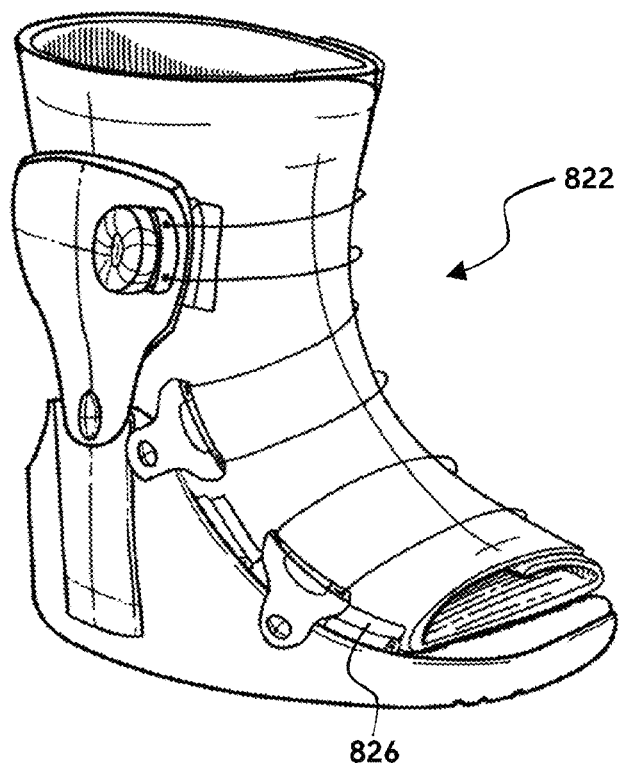
Figure 8G:
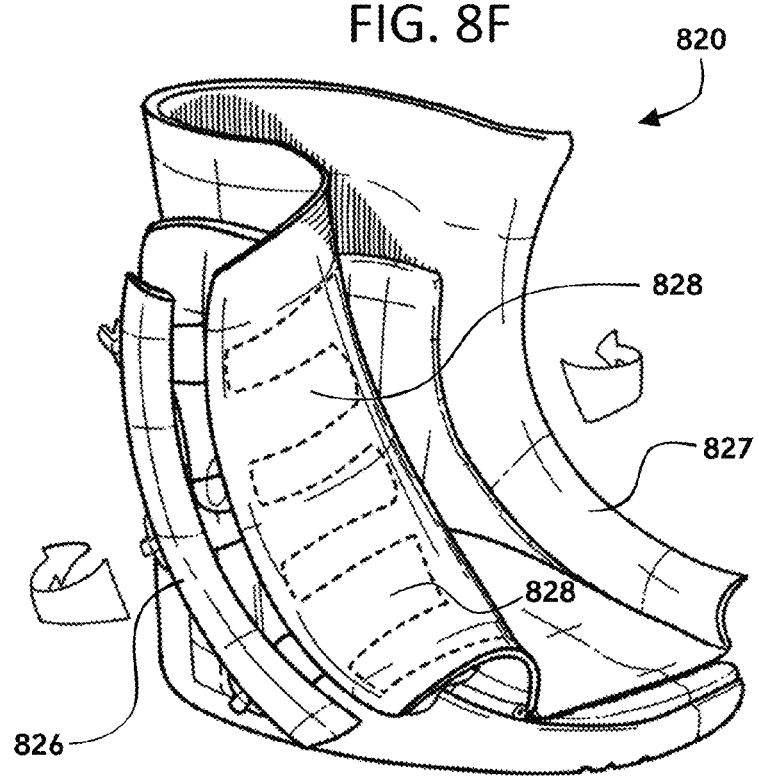

FIGS. 8F and 8G illustrates another embodiment 820 of a system for opening a brace. Embodiment 820 includes a spring that is mounted on a relatively rigid material or a portion of a brace that is further coupled with the upper material of the brace. The material of the brace may include fingers or components 828 that structurally support the material and allow the material to be opened via the spring. In some embodiments, the material may be further coupled with a panel 826 that may be folded over an opening 827 of the brace and coupled with an opposite side of the brace to close the brace. When the panel 826 is uncoupled from the opposite side of the brace, the spring may cause the entire panel 826 to swing open. To close the brace, the user may grasp the panel 826, fold the panel 826 over the opening 827, and couple the panel 826 with the opposite side of the brace. In some embodiments, panel 826 may include a male or female component, such as those described herein, that couples with a corresponding male or female component attached to the opposite side of the brace.

Figure 8H:
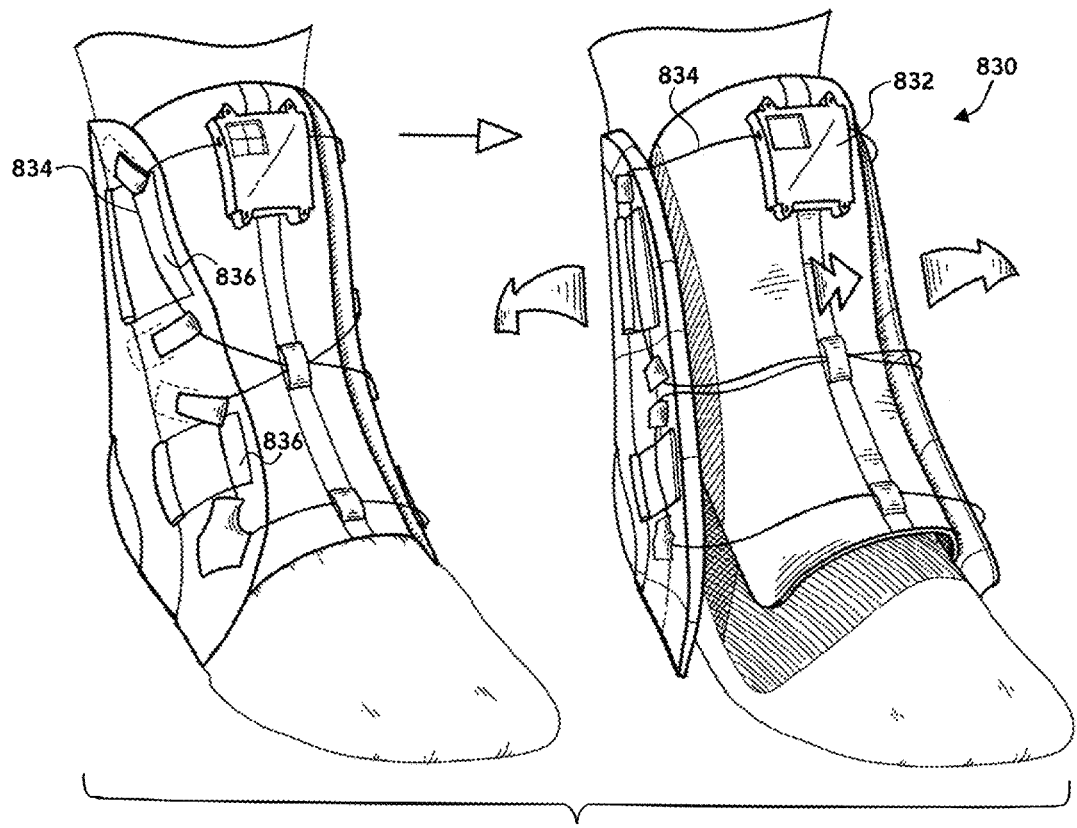

FIG. 8H illustrates another embodiment 830 of a system that may be used to automatically open a brace. Embodiment 8H includes a spring member 836 that is positioned under the lace 834 of the lacing system. Spring member 836 is configured to press against the lace 834 such that when tension is released from lace 834, spring member 836 causes the lace 834 to unwind from a spool within the motorized closure system 832. As the lace 834 unwinds from the spool, pressure is removed from the patient's body part and the brace opens. In some embodiments, a spring member 836 is coupled with the eyestay of the brace such that removal of tension from lace 834 causes the eyestay, and thus the brace, to open via spring member 836. As briefly described above, the embodiments of FIGS. 8A-H provide a form of lace management to reduce or eliminate tangling of the lace as tension is removed from the lace.

As previously described, in some embodiments the brace may be fit with one or more sensors that communicate with an electronic device (e.g., a smart phone, tablet pc, personal computer, and the like) or external computing device to monitor physical characteristics of the patient. The sensors may communicate with the electronic device via Bluetooth, dated cord, USB, or using any other method known in the art.

Figure 9C:
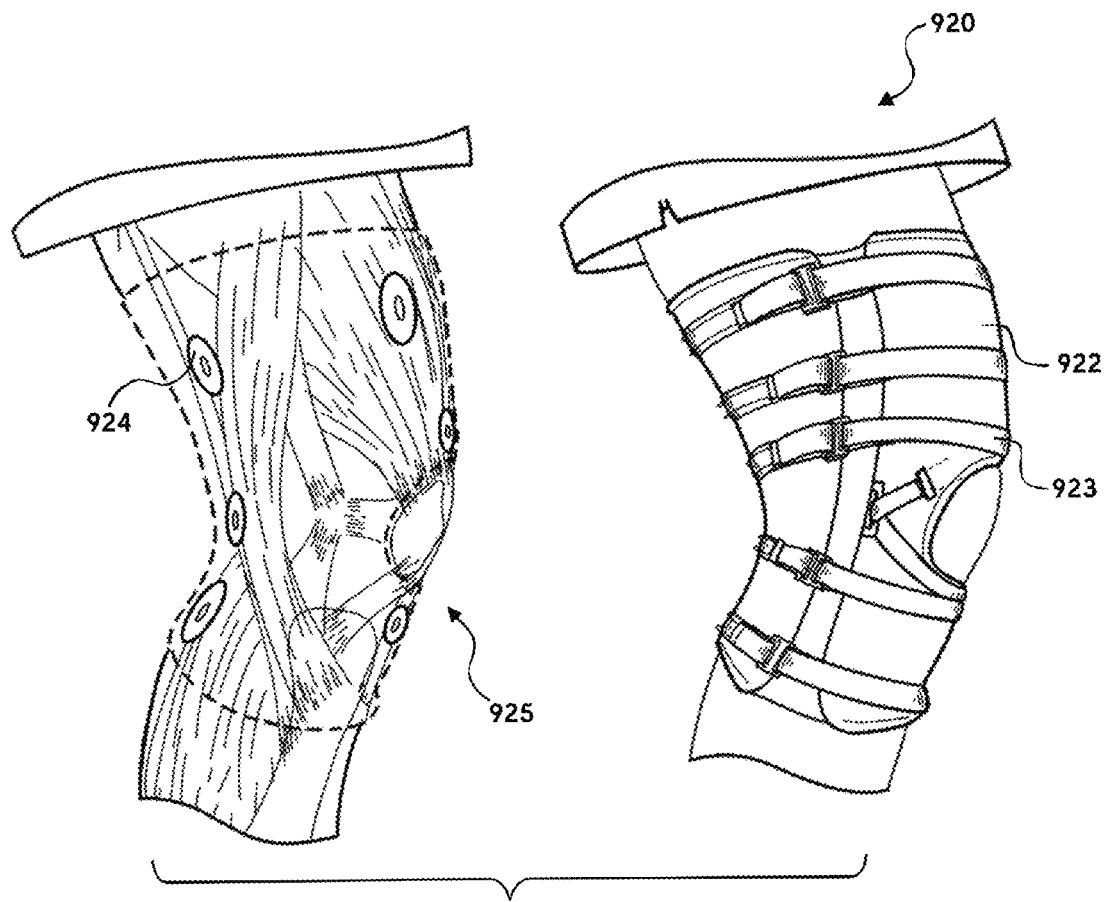
Figure 9D:
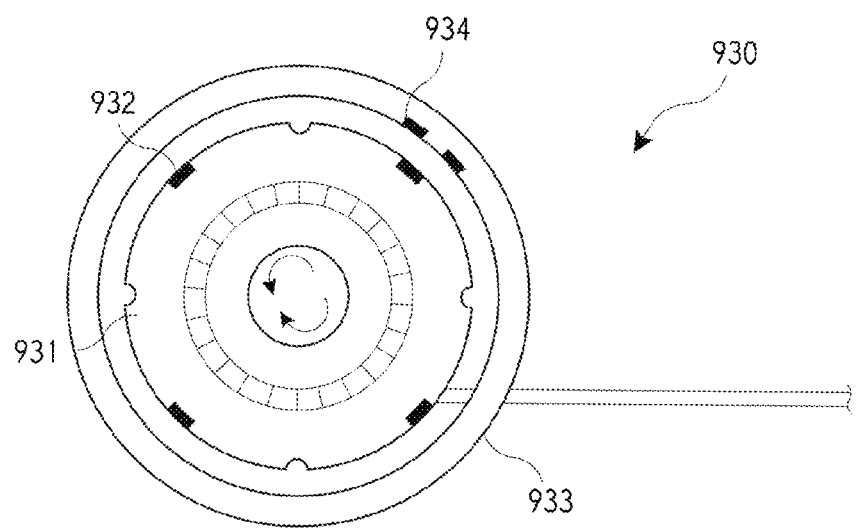
Figure 9E:
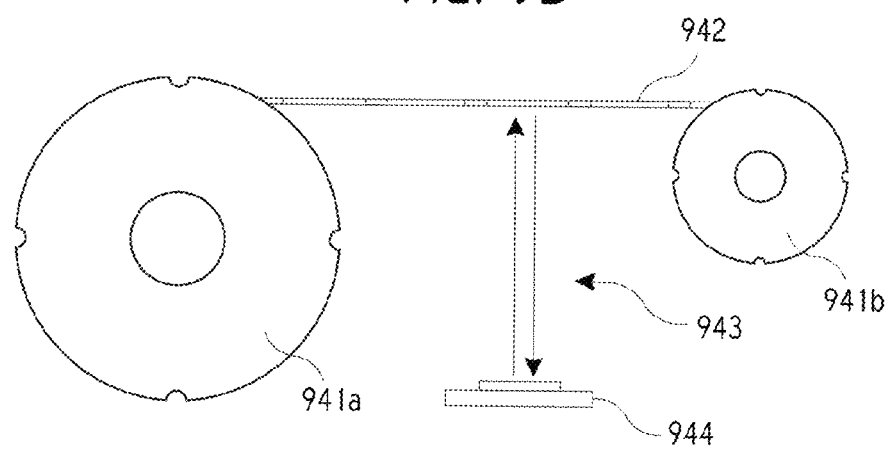
Figure 9F:
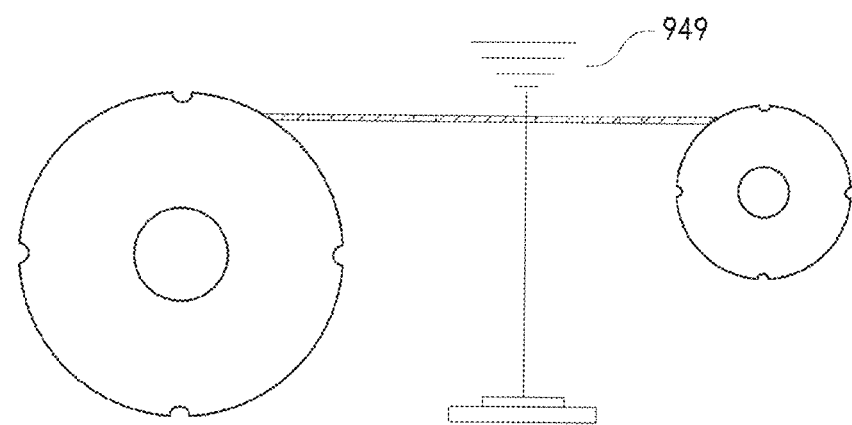
Figure 9G:
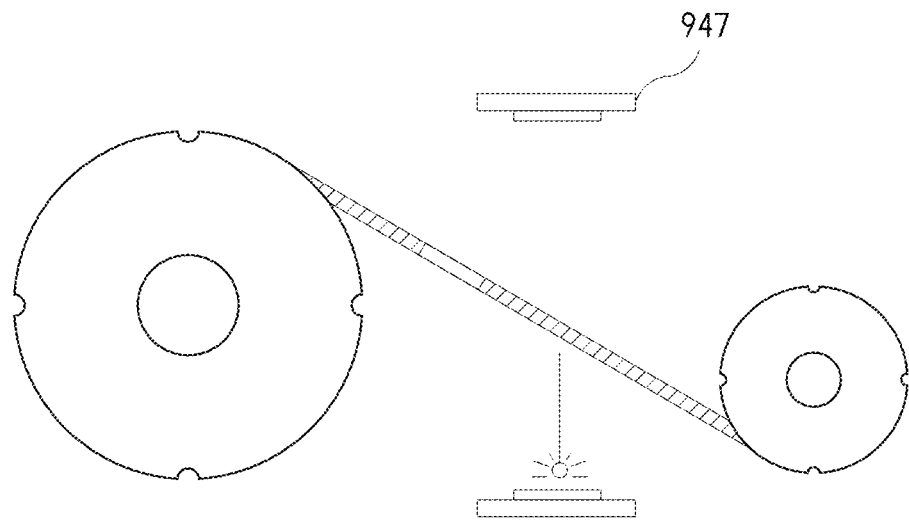
Figure 9H:
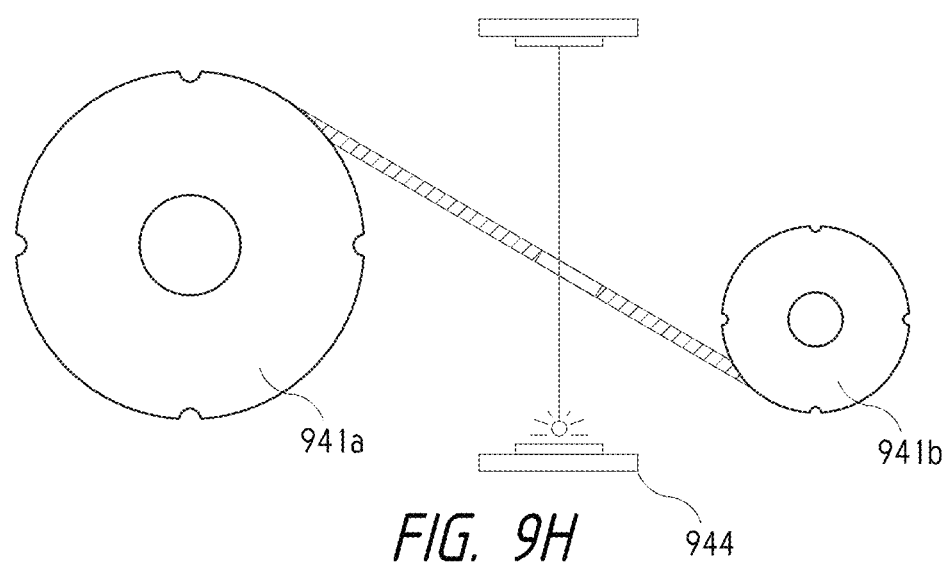
Figure 91:
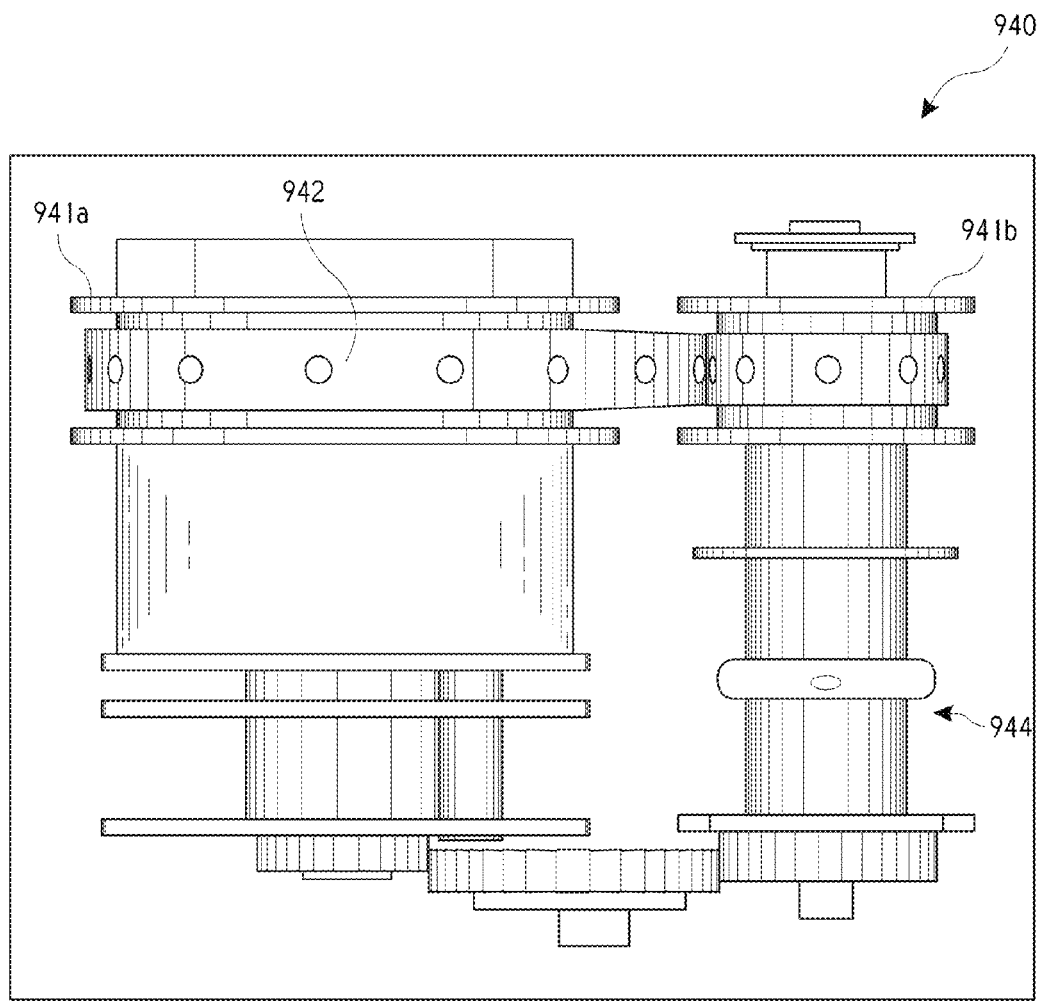
Figure 9J:
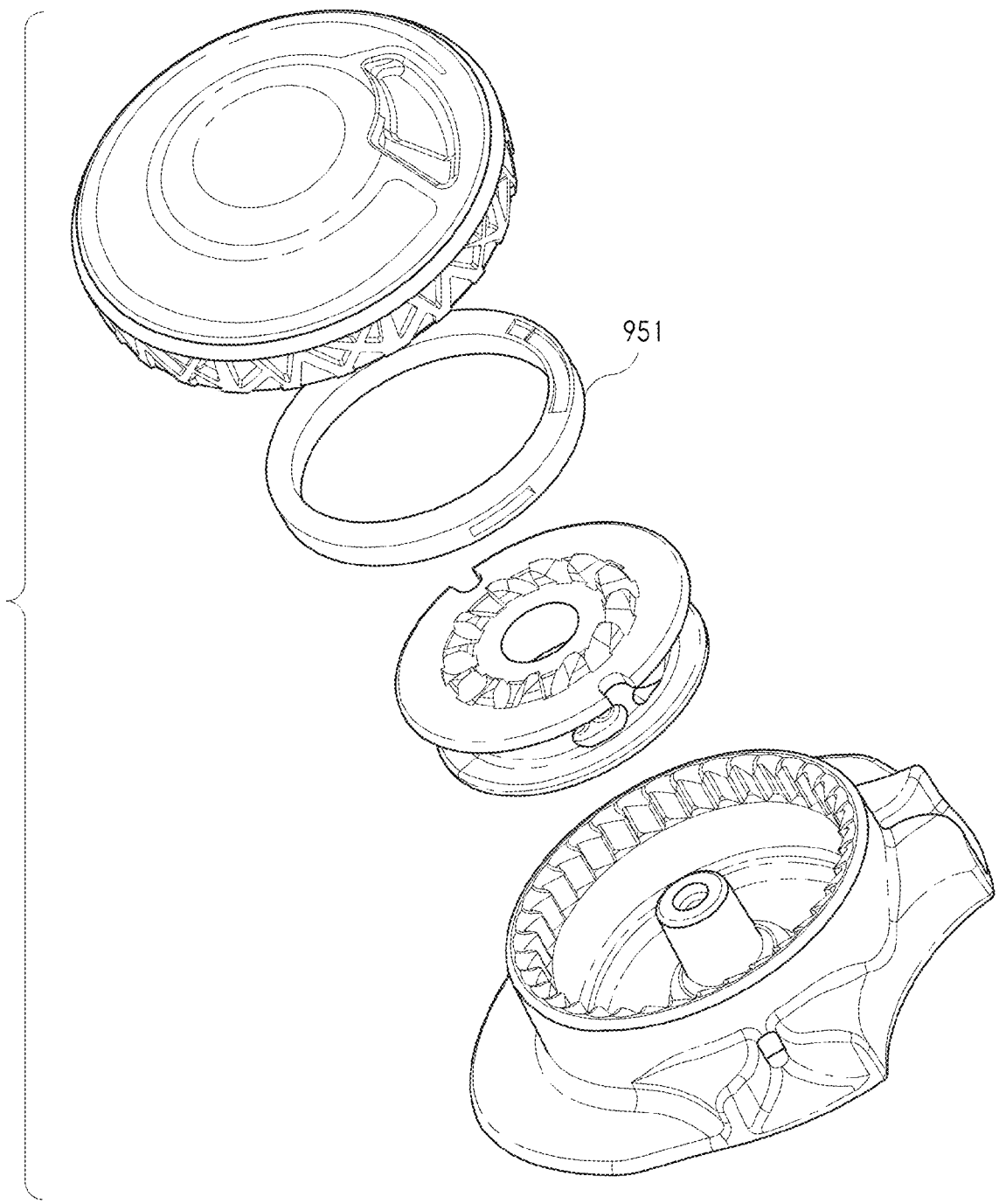
Figure 9K:
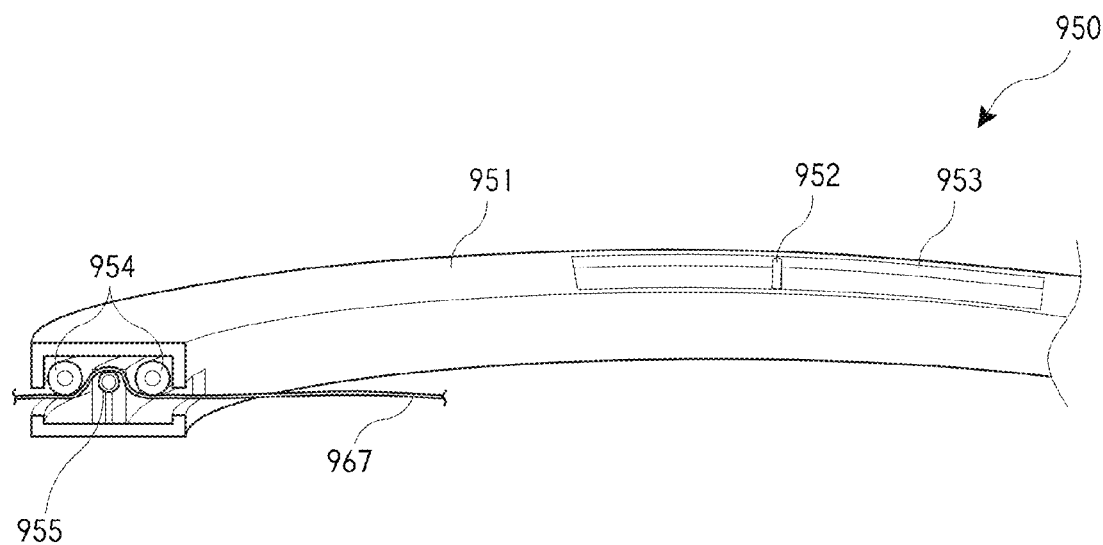
Figure 9L:
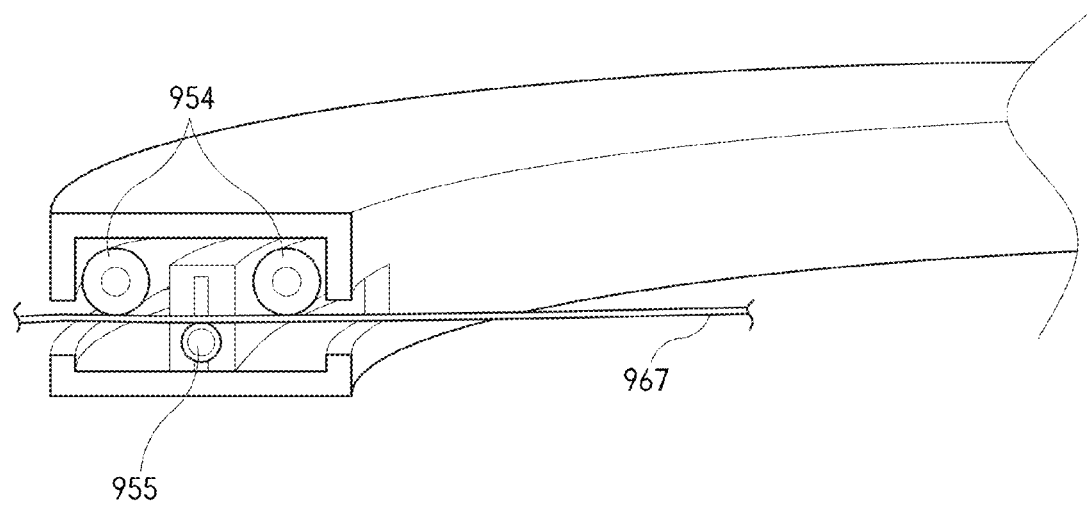
Figure 9M:
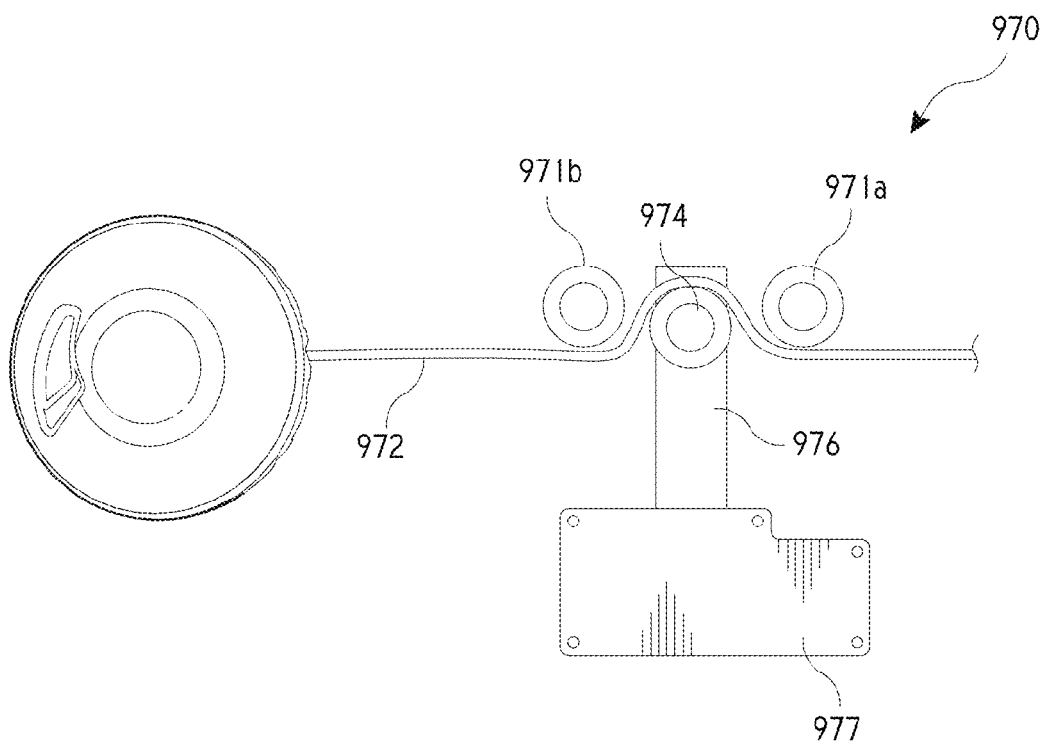
Figure 9N:
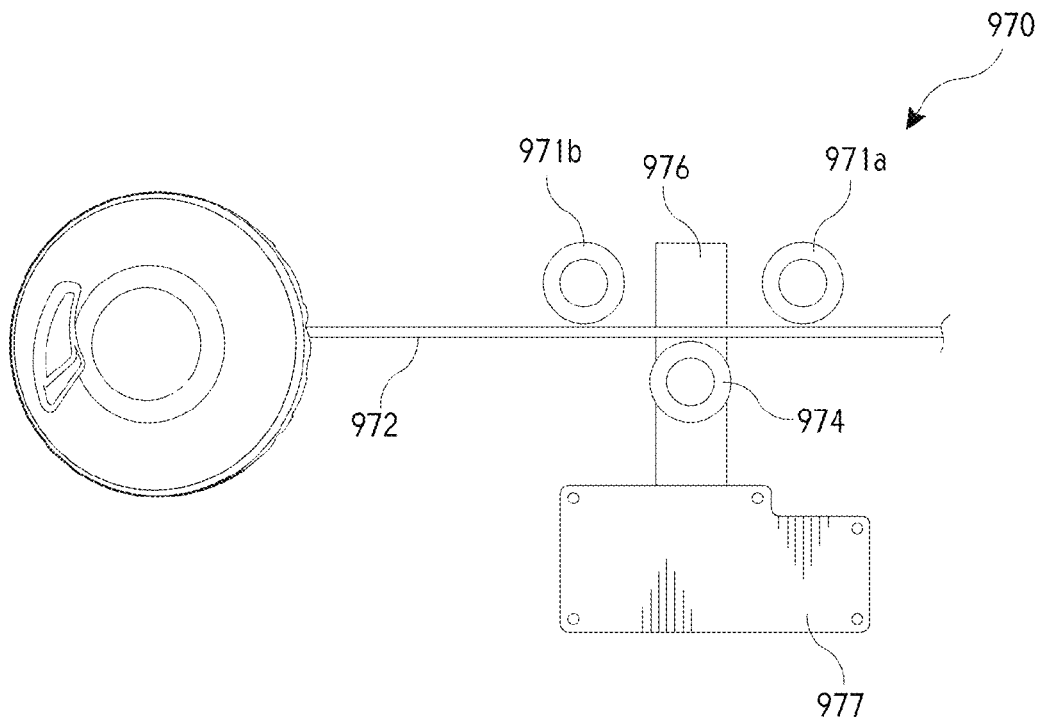
Figure 9O:
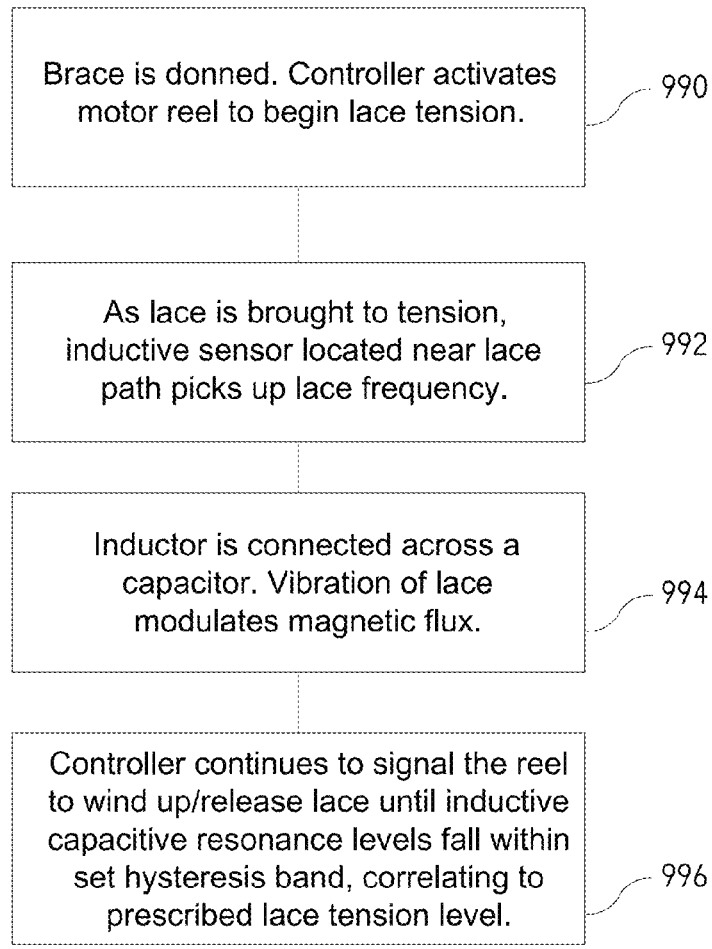
Figure 9P:
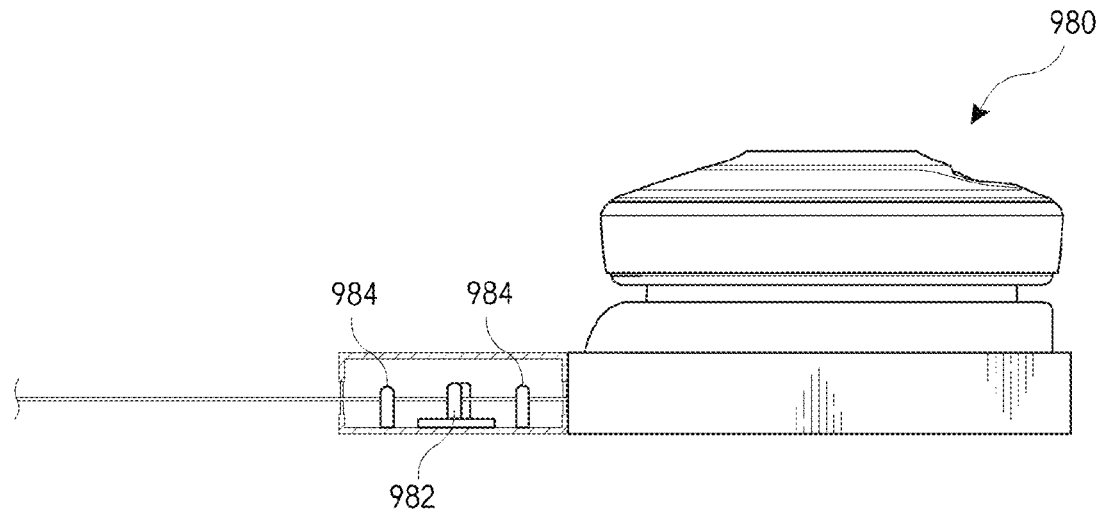

Referring now to FIGS. 9A-P, illustrated are various embodiments of sensors that may be used with a brace to monitor physical conditions of the patient. FIG. 9A illustrates a first embodiment 900 of a brace 902 that includes a plurality of sensor bands 904 that stretch across a gap 905 of the brace. Sensor bands 904 may be used to determine a pressure exerted on the patient's body part, such as to determine an amount that the brace is open or closed. In some embodiments, the sensor bands 904 may be used to determine the pressure in different zones of the brace, such as by measuring the pressure near the wrist and/or adjacent the elbow.

In some embodiments, an elastic material 906 may be placed under the sensor bands 904 to support the brace and/or prevent the sensor bands from rubbing against the user's skin. The sensor bands 904 function as formation strain gauges such that brace tension may be detected through deformation of the sensor bands. Stated differently, brace tension is detected as the sensor bands 904 stretch. The material characteristics of the sensor bands 904 are known so that the brace tension may be calculated based on the stretch of the sensor bands 904. The sensor bands 904 may crisscross the gap 905 of the brace to provide accurate monitoring of that brace tension. The sensor bands 904 may be electrically coupled with the motorized closure devices, or with any other unit, so as to provide electrical signals that may be interpreted to calculate the brace tension.

FIG. 9B illustrates another embodiment of a brace 910 having one or more sensors 912 attached to an inner surface of the brace 910. The sensors 912 may be configured to monitor conditions of the patient upon stretching, compression, or other deformation of the sensors. The sensors 912 may be configured to monitor tension, temperature, pressure, and the like. By placing the sensors 912 on the inner surface of the brace 910, the sensors 912 are positioned adjacent the user's body and are thus able to accurately monitor the physical conditions of the patient. The monitored conditions of the patient may be recorded by a motorized closure device or some other component of the brace. In some embodiments, the brace 910 may include a manual closure device instead of a motorized closure device. A benefit of using sensors 912 is that brace 910 may have a low profile due to the sensors 912 being positioned on the interior surface of brace 910. In some embodiments, sensors 912 may be made of a relatively sticky or tacky substance to help prevent migration of the brace 910 about the patient's body part.

Data monitored by sensors 912 may enable the brace fit to be automatically adjusted as described herein, may enable tension feedback to be provided to the user, and/or may enable the data to be analyzed by a physician to monitor the effectiveness of a prescribed therapy.

In some embodiments, the sensors may be small circuits that are printed on an insert that is fit or placed within the brace (i.e., thin film pressure sensor), such as within a foot bed of the brace. The printed sensors may monitor pressure or other conditions of the patient as desired. In some embodiments, the sensors may be printed on a flexible membrane or material that may be placed on the patient's skin or included within the brace. FIG. 9C illustrates one embodiment 920 of a brace 922 that includes an insert 925 that is applied next to the body part of the patient. Insert 925 includes individual sensors 924 that may be used to sense individual muscle movement and/or tendon/ligament activity. Insert 925 may include a sufficient number of sensors 924 such that the entire activity of the body part supported by brace 922 may be monitored and recorded. In this manner if individual parts of the body are of a particular concern, these parts of the body may be more closely monitored or abnormalities detected. In some embodiments, brace 922 may include individual tension control units or devices 923 that may be individually tightened to apply zonal pressure to the body part. For example, if it is determined that an upper region of the patient's limb needs additional support based on data collected by sensors 924, the tension in the upper tension control units 923 may be increased so as to provide the additional support to the upper regions of the patient's limb.

FIGS. 9D-P illustrate embodiments in which the pressure on the patient's body may be indirectly measured. Indirect measurement of pressure means that the pressure is being calculated or implied based on one or more measurements. These measurements are typically obtained from the reel system or motor of the motorized or manual closure device. FIG. 9D illustrates one embodiment 930 in which magnets are placed on a spool 931 and housing 933 of the motorized or manual closure device and used to obtain measurements via a Hall effect. Specifically, spool 931 includes a plurality of magnets 932 spaced circumferentially around the spool 931. Housing 933 includes a pair of magnets 934 placed on an interior wall of the housing. Magnets 934 of housing 933 detect rotation of spool 931 as magnets 932 rotate around and pass magnets 934. As magnets 932 pass magnets 934, an electrical signal is generated which is used to interpolate or calculate lace displacement and direction. The displacement and direction of the lace is used to calculate an amount of tension or pressure applied to the user's limb via the brace. The use of two magnets 934 on the interior of housing 933 allows the direction of the spool 931 to be determined. In other embodiments, the magnets may be placed on the lace itself, included as a part of a separate spool, used in the knob and housing, included within a guide of the lacing system, and the like.

FIGS. 9E-I illustrate another embodiment 940 of a system for indirectly measuring a pressure applied to the patient's body part. Specifically, the motorized or manual reel system includes an arrangement of spools, 941*a* and 941*b*, around which a spring or strip of material 942 is wound. Spring 942 includes a plurality of holes evenly spaced along a longitudinal length thereof. A light source 944 is positioned beneath the spring 942 and is used to determine the displacement of the spring 942. The displacement of spring 942 corresponds to a displacement of lace of the lace winding system. For example, as the lace is wound around a spool (not shown), the spring 942 is likewise wound around a spool (i.e., 941*a* or 941*b*). The light source 944 emits a beam 943 that contacts spring 942 and is reflected back towards light source 944. As the spring 942 displaces, beam 943 eventually encounters and passes through one of the holes of spring 942 and is detected by a light sensor 949 or conversely, is not detected by light source 944. The displacement of spring 942 may be monitored by measuring the number of times the light source passes through one of the holes spring 942. This information is used to calculate or interpolate the displacement and/or tension of the lace, which is in turn used to calculate the pressure applied by the brace. FIG. 9I illustrates a top view of a motorized tensioning device that includes the embodiment 940 for indirectly measuring a pressure applied to the patient's body part.

FIGS. 9J-L illustrate another embodiment 950 of measuring lace tension. In this embodiment lace 967 is inserted through a tension meter ring 951 and threaded around a plurality of posts, 954 and 955, which are used to measure the tension of lace 967. Specifically, two of the posts 954 are fixed in relation to tension meter ring 951 while a third post 955 is movable within the tension meter ring 951. As the lace tension increases, the third post 955 is pressed downward within tension meter ring 951. Third post 955 may in turn be coupled with a landing pad (not shown) which is threadingly coupled to a gear (not shown). As the third post 955 moves downward within tension meter ring 951, the landing pad may be forced downward which causes the gear to spin via threaded rods (not shown). Rotation of the gear may cause a second gear (not shown) too also rotate. The second gear may be coupled with a rack (not shown) via a pinion, which causes the rack to move longitudinally within tension meter ring 951. The rack may be coupled with a pin 952 that moves within a slot 953 of tension meter ring 951 so as to visually display the tension applied to lace 967. In this manner the tension applied by the user may be visually displayed to the user as a knob of the closure device is rotated or as the motor of the motorized closure device is operated. In some embodiments, the landing pad may be coupled with a top surface of the tension meter ring 951 so that loosening the tension of lace 967 causes the landing pad to be pulled toward the top surface of tension meter ring 951.

FIGS. 9M and 9N illustrate another embodiment 970 that may be used to measure tension applied to lace of the lace winding system. Specifically, embodiment 970 includes a tension measuring device 977 having a plurality of posts that are positioned along a path of lace 972 and used to monitor or measure the tension of lace 972. Tension measuring device 977 includes a first post 971*a* and second post 971*b* that are fixedly coupled in relation to lace 972. A third post 974 is coupled with a longitudinal strip 976 that is movable in relation to tension measuring device 977. Third post 974 is positioned along the lace 972 so as to be movable in relation thereto. Specifically, as the tension in lace 972 is increased, the third post 974 and longitudinal strip 976 are moved in relation to tension measuring device 977. The movement of longitudinal strip 976 and third post 974 is measured via tension measuring device 977 and used to calculate the tension applied by the brace to the patient's limb. In some embodiments the tension applied by the brace may be output to the user via tension measuring device 977. The measurements may likewise be provided to a motorized closure system, such as those described herein, so that the system may automatically adjust the tension of the lace 972 and/or perform any of the functions described herein.

FIG. 9P illustrates an embodiment 980 in which the tension of a brace may be automatically applied by a motorized closure system in a relatively quick manner. The motorized closure system includes a proportional integral derivative (PID) controller that is communicatively coupled with one or more inductors and capacitors 982 that measure a voltage signal as tension is applied to the lace. Specifically, the motorized closure system includes lace stabilizers 984 across which the lace stretches. The inductor capacitor system 982 is positioned between the lace stabilizers 984. As the lace is tensioned, the lace stabilizers 984 cause the lace to vibrate. The vibration of the lace is measured by the inductor-capacitor system 982 and a corresponding voltage signal is determined. The motorized closure system winds the lace until the measured voltage falls within a hysteresis band of a predetermined voltage level, which corresponds to a voltage of a desired lace tension.

FIG. 9O illustrates a method of automatically closing a brace using a PID control system. Specifically, at block 990, the brace is donned and the PID control system activates the motor of the motorized real system to begin winding of the lace around a spool. At block 992, as the lace is tension, the inductive sensor located along the lace path measures the lace frequency. A block 994, the inductor is connected across the capacitor and vibration of the lace modulates the magnetic flux. At block 996, the PID continues to instruct the motor to wind the lace until the inductive capacitive resonance level falls within the hysteresis band corresponding to the prescribed lace tension level.

In other embodiments, the tension on the lace may be measured or the current or voltage of the motor of the motorized closure device may be measured and the measured readings may be equated with a corresponding pressure applied on the body part by the brace.

In some embodiments, an indicator may be used to display the tension applied by the brace. For example, in the embodiments that involve tensioning multiple zones, a color may be associated with each of the zones to indicate the pressure level in the corresponding zone. For example, a green color could be displayed to indicate that the pressure in the corresponding zone is within a preferred range, or the color could be yellow or red to indicate that the pressure in a corresponding zone is too great or insufficient.

In addition to those uses of the sensors previously described, the sensors may be used to determine how a person is walking, to determine the pressure they are applying to a body part, to determine the individual's gait or other characteristics, and the like. In one embodiment, the sensors may be used to facilitate donning and doffing of the brace. For example, a pressure sensor may be placed inside the brace so that when no pressure is applied by the patient's body part, the brace is automatically opened. As pressure is applied by the body part, such as when a patient steps into a foot brace, the brace may be configured to automatically close about a patient's body part. In this manner, patients with disabilities and/or that have difficulty manually adjusting the brace may easily don and doff the brace.

In some embodiments the motorized closure device may use low-power batteries, such as Bluetooth low-power optimized coin cells. These batteries may allow the motorized closure device to be used repeatedly over an extended period of time. The batteries may be rechargeable so that the user is able to recharge the batteries after each use or after an extended period of time.

Figures 10A, 10B:
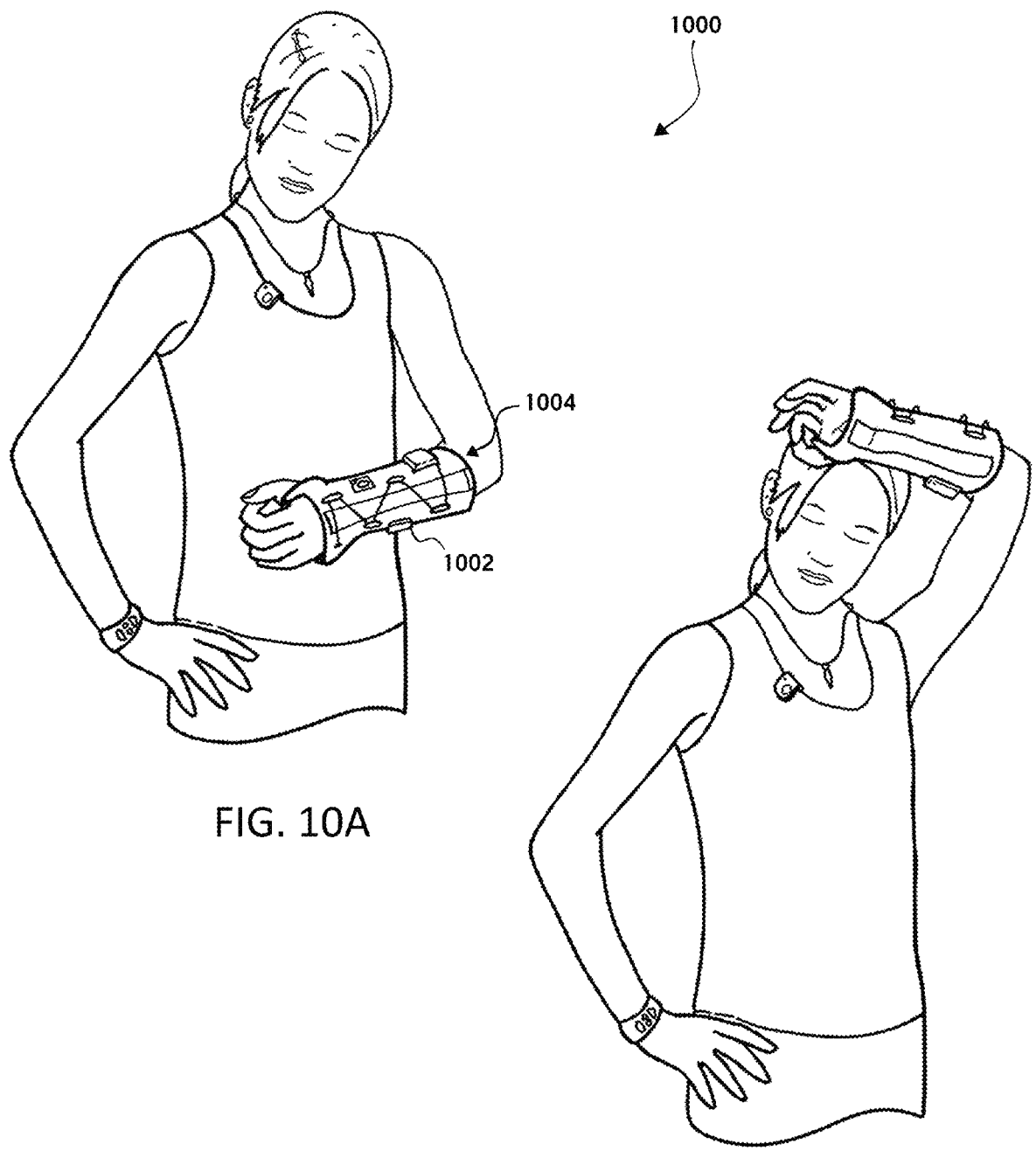
FIGS. 10A-E illustrate various embodiments in which a brace may be used to provide physical therapy to a patient.

As described briefly above, in some embodiments, the brace and sensors may be configured to provide physical therapy to the patient. Referring now to FIGS. 10A-E, illustrated are various embodiments in which the brace may be used to provide physical therapy to a patient. FIGS. 10A and 10B illustrate an embodiment 1000 in which a brace component is used to sense an orientation of a brace 1004 with respect to the patient's body and/or to sense a motion of the brace with respect to the patient's body. The brace 1004 may include an accelerometer 1002, gyroscope, or other sensor that measures the orientation and/or motion of the brace 1004. For example, in some embodiments the gyroscope may measure the brace 1004's position to determine if the brace 1004 is in an elevated or lowered position with respect to the patient's heart. The fit of the brace about the patient's limb may be adjusted according to the measurements of the gyroscope. Similarly, a physical therapy regimen may be dependent on the orientation of the brace 1004 with respect to the patient's heart. The patient may be required to maintain the brace 1004 in an elevated orientation for a specified amount of time, which can be measured or calculated via the gyroscope. The gyroscope may be a mechanical gyroscope, an optical gyroscope, a microelectromechanical systems (hereinafter MEMS) gyroscope, or any other orientation measuring device known in the art. The MEMS gyroscope and optical gyroscope provide the advantage of being inexpensive and low-profile. An accelerometer may similarly be used to measure the motion of the brace 1004 with respect to the patient's body to determine an activity level of the patient.

Figure 10C:

FIG. 10C illustrates another embodiment 1010 in which the orientation of the brace 1014 may be measured relative to the patient's body. Specifically, the brace 1014 may include a sensor 1012a that is detected by a second sensor, 1012b or 1012c, to determine an orientation of the brace 1014 relative to the patient's body and/or to determine the motion of the brace 1014 with respect to the patient's body. The brace 1014 may include an alarm that is used to signal when the patient is not complying with a prescribed regimen. This information may be recorded and transmitted to a physician for subsequent analysis and/or adjustment of a prescribed regimen.

Figure 10D:
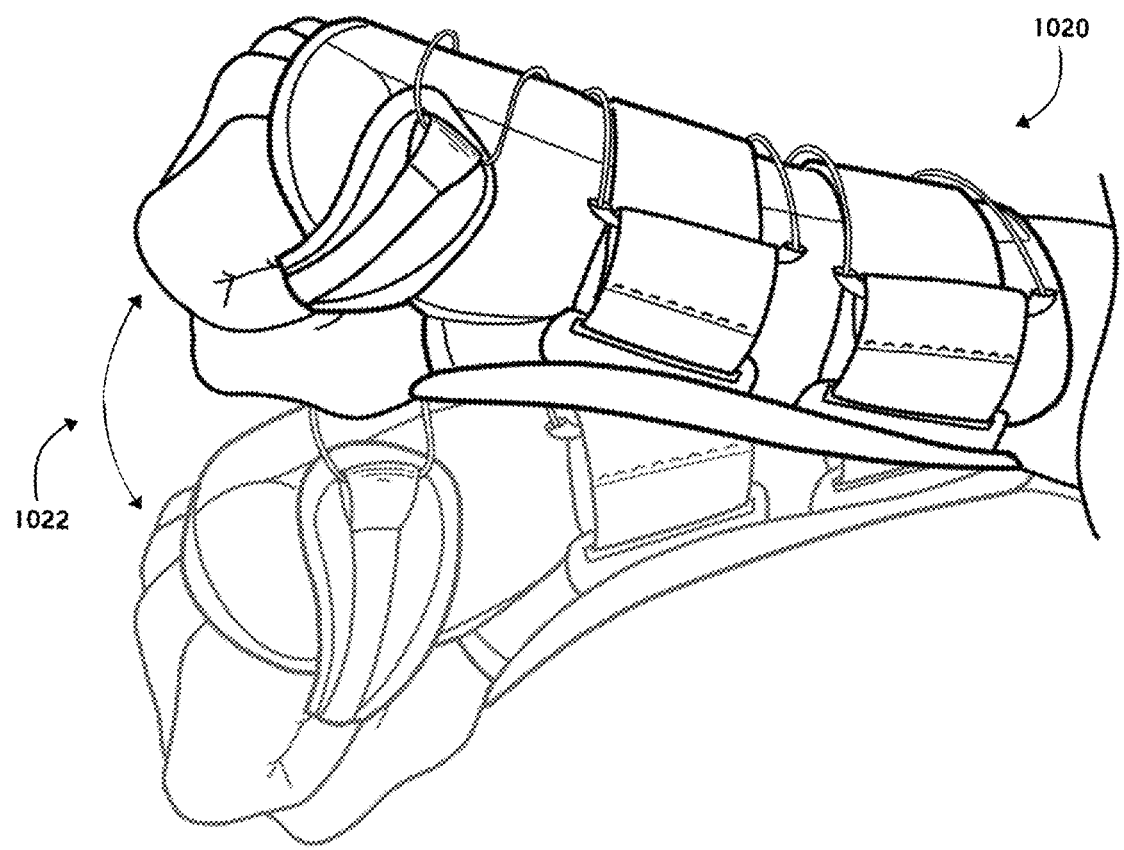
Figure 10E:
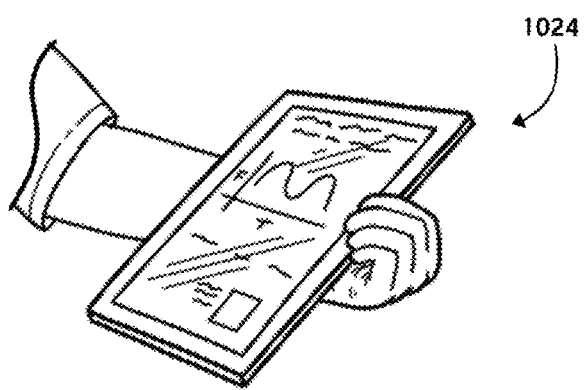

FIG. 10D illustrates a brace 1020 being used to provide resistance so as to provide physical therapy for a limb of the patient, such as a wrist. The brace 1020 could be programmed to provide cycling or repetitive therapy, forcible therapy, spring therapy, and the like. These therapies could be provided by allowing the brace to flex within a certain range and/or in response to a defined force. The motorized closure device may be configured to allow the brace to flex within a defined range or in response to a defined force. Similarly, the motorized closure device may allow the brace to flex at a defined speed. For example, a wrist brace may be designed to allow the patient's wrist to flex as the patient flexes his or her forearm muscles. This may help prevent the muscles from atrophying and/or may help the muscles recuperate from an injury. As shown in FIG. 10E, in some embodiments, the physician may create a therapy regimen on an electronic device 1024 and the therapy regimen may be transmitted to the motorized closure device of the brace. The physician may create the therapy regimen by merely swiping a finger across the screen of the electronic device 1024 or by otherwise entering this information into the electronic device.

In some embodiments, the brace 1020 may be used to provide physical therapy for the patient. As previously described the motorized closure device can be configured to function as a constant or variable force spring so that the brace provides a force or load against which the patient presses. The force or load applied by the brace 1020 may be increased over time according to a prescribed therapy regimen so that the body part continues to grow stronger as desired. A PID controller, such as that previously described, may be used to provide the physical therapy. The range of motion of the brace 1020 may likewise be increased as the patient's body part grows stronger and/or heals. In some embodiments, physical therapy may only be allowed during a specified time period. The brace may be rigidly configured when physical therapy is not being performed to provide a maximum amount of support to the limb.

The brace 1020 may be configured with a prescribed therapy regimen in a variety of ways. For example, in some embodiments, the physical therapy regimen may be transmitted wirelessly (e.g., via Bluetooth and the like) or may be transmitted via one or more data cords. The brace 1020 may include a user interface that displays various information to the user, such as the prescribed physical therapy regimen, one or more parameters of the closure device, the tension applied by the brace, and the like. The user interface may also include one or more inputs that the user can select to adjust the various parameters of the brace, input one or more messages to a physician, access one or more menu pages, and the like.

As previously described, data on the usage of the brace may be monitored and transmitted to a database so that a physician may be able to determine how the patient is complying with a physical therapy regimen. Compliance with the regimen may be monitored by measuring the activity of the body part per a unit time. The amount of flex of the body part may also be measured.

In some embodiments the sensors may operate with a display that displays to the patient when an appropriate amount of physical therapy has been performed. For example, the brace may include a green LED light that is illuminated when the patient has flexed the body part, such as a wrist, by an appropriate amount according to a prescribed regimen. When the LED is illuminated, the patient may recognize that the body part has been flexed to a sufficient degree to promote healing of the body part. Such braces may allow a physician to quickly and inexpensively treat a patient in addition to stabilizing the body part. Since the brace is able to both stabilize and provide rehab to the body part, the number of visits the patient must make to be physician's facility is greatly reduced.

As previously described, in some embodiments the brace may be designed to provide feedback to the doctor regarding the patient's compliance in wearing the brace and/or the patient's compliance with a physical therapy regimen. If the patient is not complying with either the regimen or with wearing the brace, the physician may contact the patient and question the patient regarding the patient's activities. The physician may adjust the physical therapy regimen and/or the brace wearing requirements based on the patient's compliance.

In some embodiments, the movement or motion sensor may be combined with a force sensor so that the system is able to track both the range of motion of the brace and the force required to achieve that range of motion. This information can be provided to the physician so that the physician knows both the amount of movement the patient is making and the force required to achieve that movement. This information may help the physician prescribe and/or adjust a physical therapy regimen.

In some embodiments, the data collected from the motorized closure device may be collected and recorded in a centralized database. In this manner, large amounts of data may be analyzed to determine the effects or effectiveness of various prescribed physical therapy regimens and/or used to adjust or generate one or more regimens. In this manner a physical therapy regimen prescribed by a physician may be tailored to the individual needs of a specific patient.

Figure 11A:
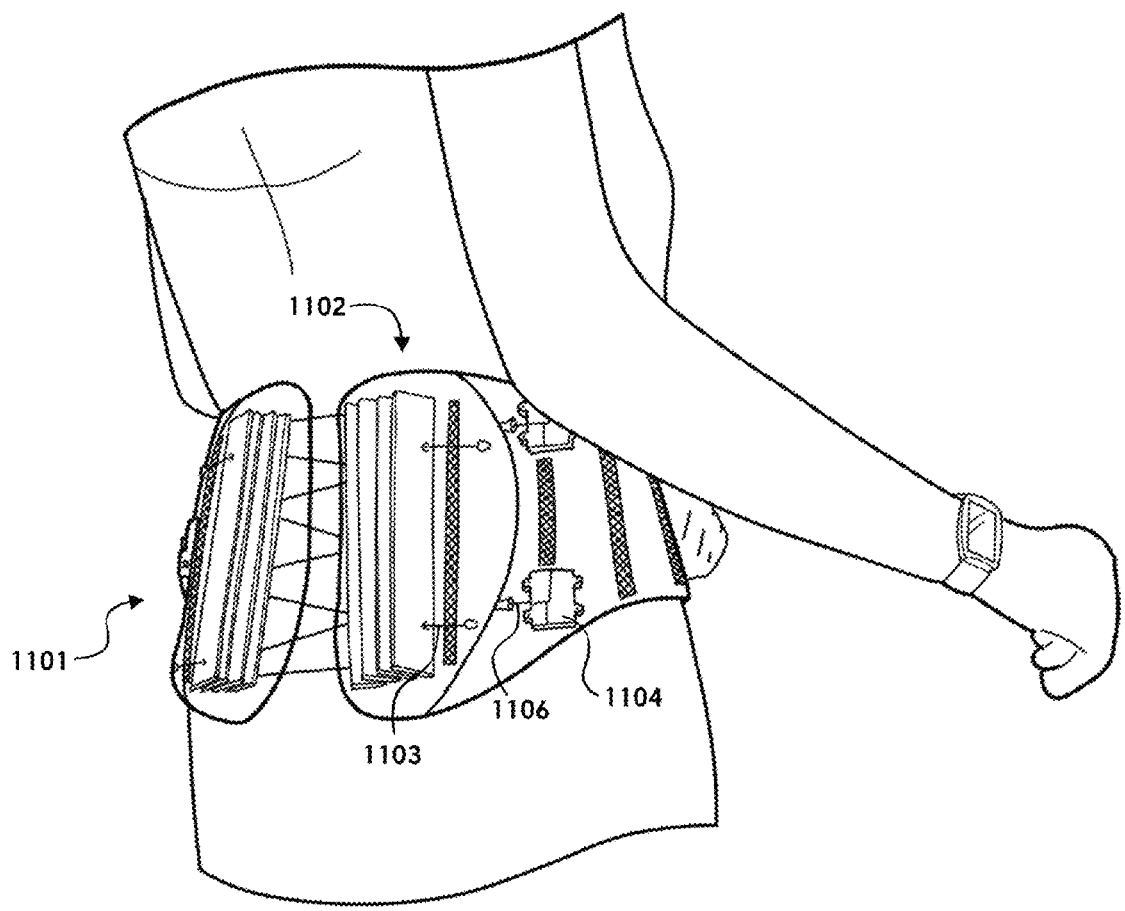
FIGS. 11A-C illustrate an embodiment of adjusting a stiffness of a brace via a motorized tensioning device.
Figure 11B:
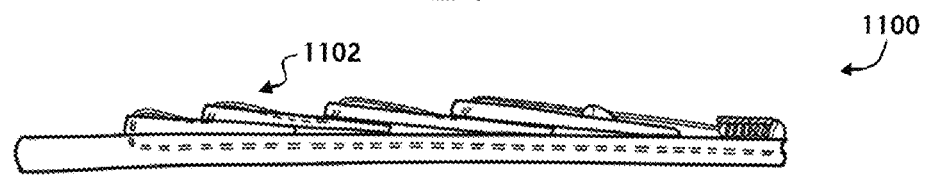
Figure 11C:
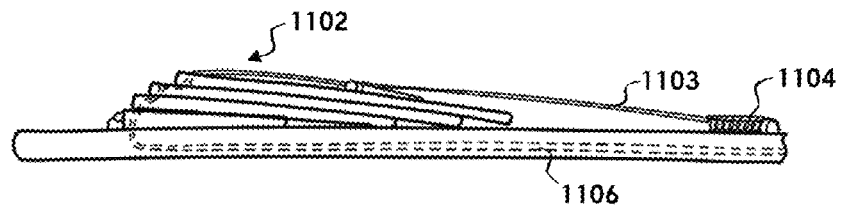

Referring now to FIGS. 11A-M, illustrated are various other implementations of a motorized closure system on a brace. FIGS. 11A-C illustrate a back brace 1101 having a motorized closure device 1104 that may be used to adjust a flexibility of the brace 1101. Specifically, the motorized closure device 1104 is coupled to a plurality of panels 1102 that are stacked atop one another so as to slide relative to one another. The motorized closure device 1104 is coupled to the panels 1102 via a first lace 1103 and a second lace 1106. The first lace 1103 is connected to a proximal panel and maybe tensioned to pull the plurality of panels 1102 apart. In this configuration the panels 1102 and back brace 1101 are relatively flexible. The second lace 1106 is wrapped around a distal panel and coupled with the proximal panel. The second lace may be tensioned to pull the panels 1102 together. In this configuration the panels 1102 and back brace 1101 are relatively rigid.

In some embodiments, a plurality of motorized closure devices may be coupled with individual panels to provide zonal support and/or flexibility. The back brace 1101 may also include sensors that measure the pressure, posture, support, tension, and the like. The sensors may provide this information to the motorized closure device 1104 and/or another component, which may use this information to determine if the brace 1101 needs to be more rigid or more flexible.

Figure 11D:
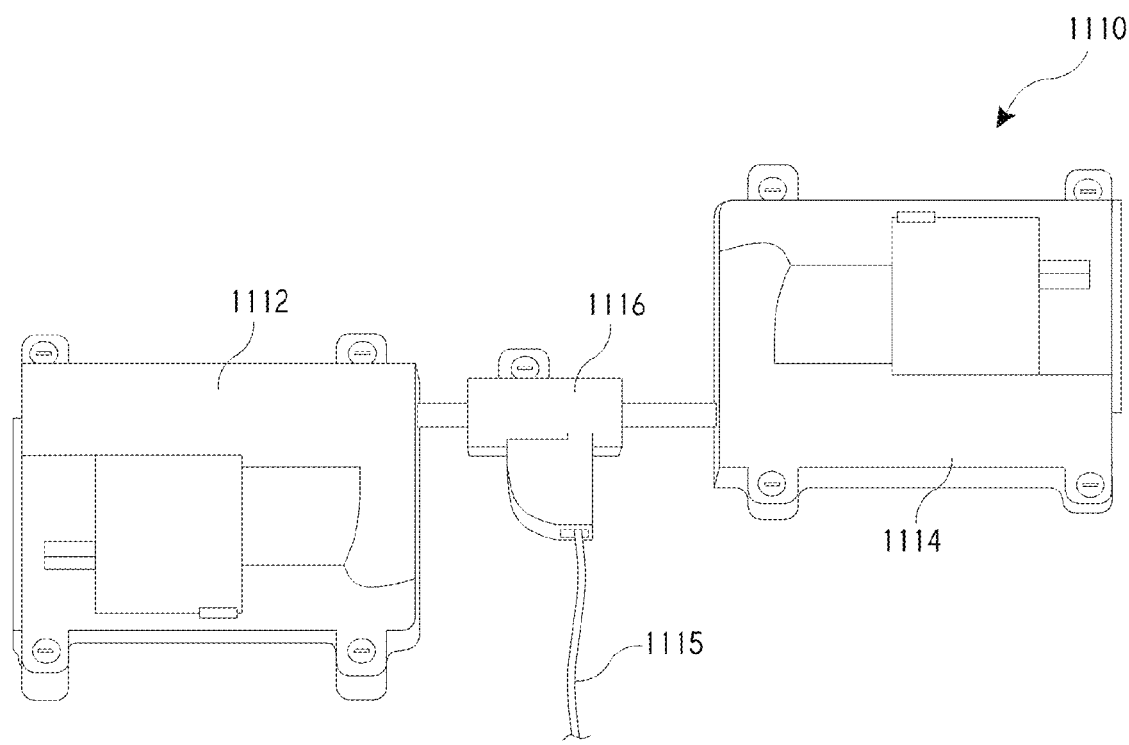
FIG. 11D illustrates a motorized tensioning device including two motorized units.

FIG. 11D illustrates an embodiment 1110 that includes a plurality of motorized closure devices. Specifically, embodiment 1110 includes a first motorized closure device 1112 and a second motorized closure device 1114. The first motorized closure device 1112 may be used to quickly wind the lace 1115 about a spool 1116. The second motorized closure device 1114 may be used to provide fine or micro adjustment of the tension applied to lace 1115. In some embodiments the two motors may be configured to run at different gear ratios so as to quickly or more fine-tunely wind the lace 1115. In another embodiment, the first motorized closure device 1112 may be used to wind and unwind the lace and the second motorized closure device 1114 may be used only when a force greater than that provided by the first motorized closure device 1112 is required.

Figure 11E:
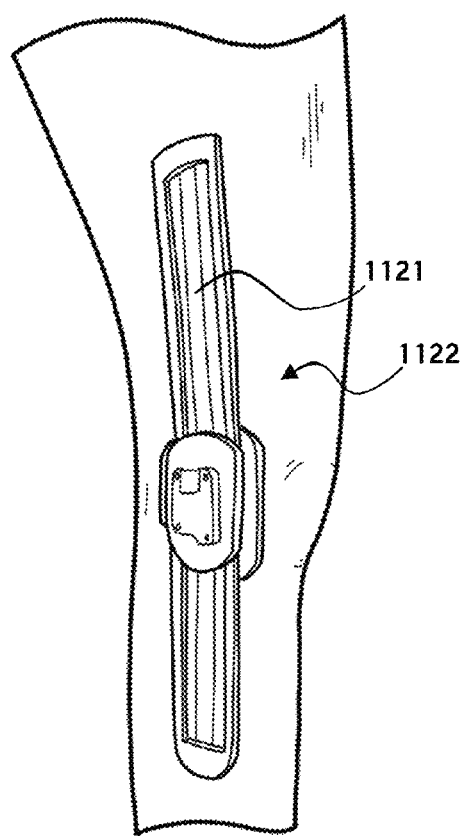
FIGS. 11E-G illustrate an embodiment of a brace including individual and zonally tensionable units.
Figure 11F:
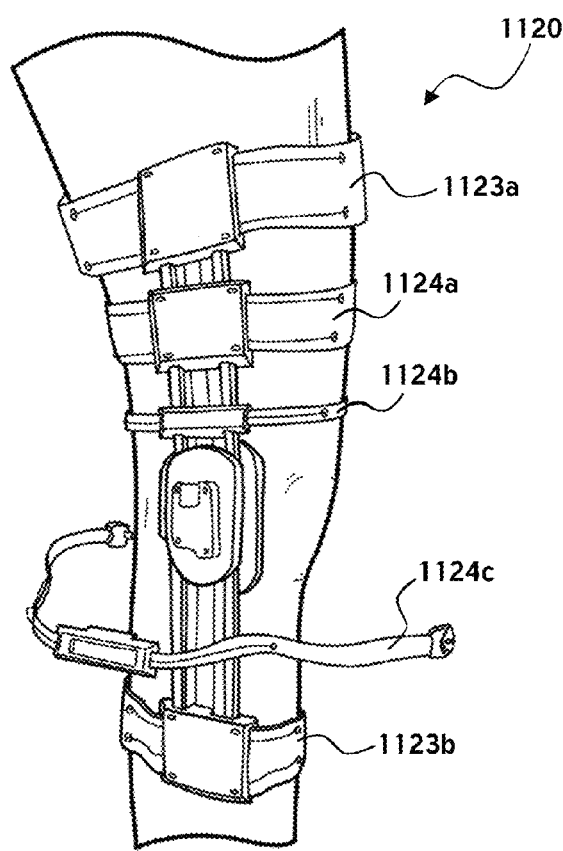

FIGS. 11E and 11F illustrate a brace 1120 that includes a base frame 1122 that may be coupled about a patient's body part, such as a knee, via a first fastening member 1123a and a second fastening member 1123b. Base frame 1122 is configured so that one or more motorized closure devices (i.e., 1124a, 1124b, 1124c, etc.) may be attached to the base frame 1122 and wrapped around the patient's body part. Base frame 1122 may include a central post 1121 along which the motorized closure devices (i.e., 1124a, 1124b, 1124c, etc.) are attached. The individual motorized closure devices (i.e., 1124a, 1124b, 1124c, etc.) may be individually tensioned so that zonal pressure is applied to the patient's body part as desired. For example, if the lower portion of the patient's body part needs additional pressure, the motorized closure devices positioned adjacent to the lower portion of the patient's body part may be tensioned while the other motorized closure devices remain relatively loose.

Figure 11G:
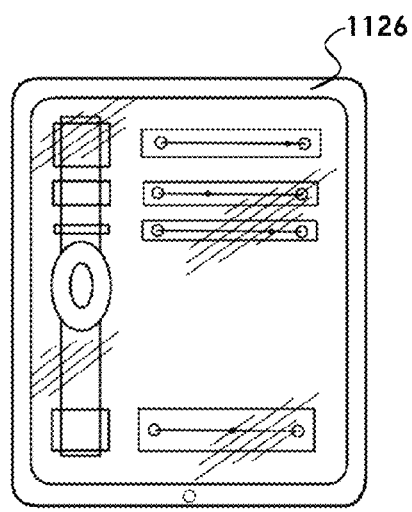

In some embodiments, the first fastening member 1123a and/or the second fastening member 1123b may also function as motorized closure devices so as to provide additional zonal pressure points. As shown in FIG. 11G, the individual motorized closure devices and/or first and second fastening members (i.e., 1123a, 1123b, 1124a, 1124b, 1124c, etc.) may be individually controlled via an electronic device 1126 (e.g., smart phone, tablet, laptop, and the like), via controls on the individual units, via a wrist band or other band worn by the patient, and the like. When a motorized closure device is coupled with the base frame 1122, the motorized closure device and its position relative to the other motorized closure devices may be detected by the electronic device 1126 or other device that is used to individually tension the motorized closure devices. In some embodiments, central post 1121 may include electronic components that help detect the position of a recently attached motorized closure device.

Figure 11H:
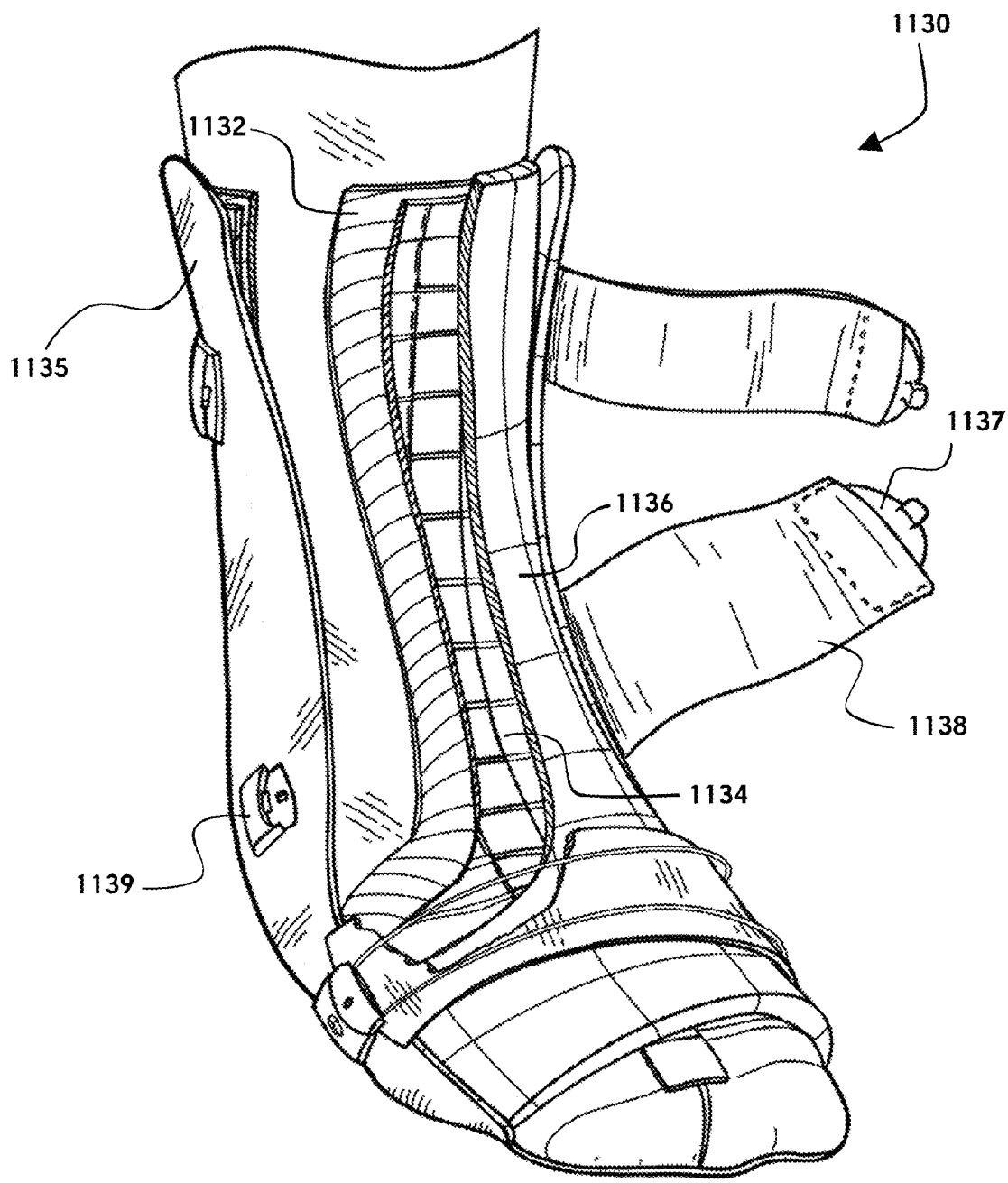
FIG. 11H illustrates a brace having a plurality of nitinol wires that are used to tighten the brace.

FIG. 11H illustrates a brace 1130 having an alternative closure mechanism. Specifically, brace 1130 uses nitinol wires to close the brace about the patient's body part, which in the illustrated example is a patient's foot. Nitinol materials exhibit a unique property of contracting upon the application of an electric current. The shrinkage of such wires typically corresponds to the current applied. As such, brace 1130 includes a plurality of nitinol wires that wrap around the patient's body part that may be activated with an electric current to contract and apply pressure to the patient's body part.

Brace 1130 includes an inner layer 1132 of material that directly contacts the patient's skin or other material, such as a sock. Inner layer 1132 may insulate the patient's body from the nitinol wires so as to protect the patient from any heat generated upon the application of an electric current and/or to minimize any point pressures that may be created from the nitinol wires. Brace 1130 also includes a second layer 1134 of nitinol wires. The second layer 1134 may be a sock and the nitinol wires may be wrapped circumferentially around the sock. Brace 1130 may also include a third layer 1136 of material that covers the second layer 1134 of nitinol wires to protect the wires and/or to insulate the wires from any external objects. Brace 1130 may further include an outer layer or shell 1135 that provides structural support to the brace 1130 and/or that protects the inner layers and components. Outer shell 1135 may be coupled with straps 1137 that are placed and coupled over an opening of the brace 1130 to close the brace about the patient's body part. The straps 1138 may include male and female coupling components, 1137 and 1139, such as those described herein.

A benefit of using the nitinol wires of brace 1130 is that such wires may be individual activated to provide localized pressure to the patient's body part. In addition, the individual wires may be activated in sequence as described in more detail below to provide additional benefits, such as pumping of the blood, or other fluid, to or from the body part.

Figure 11J:
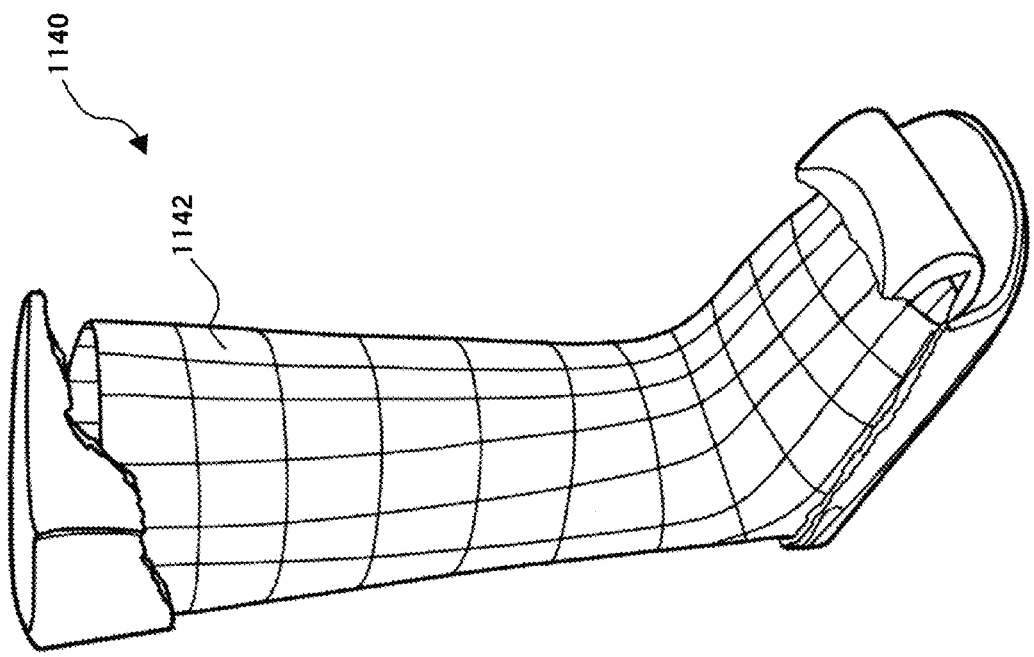
FIGS. 11I-K illustrate various embodiments of braces having pressure and/or other sensors.
Figure 11I:
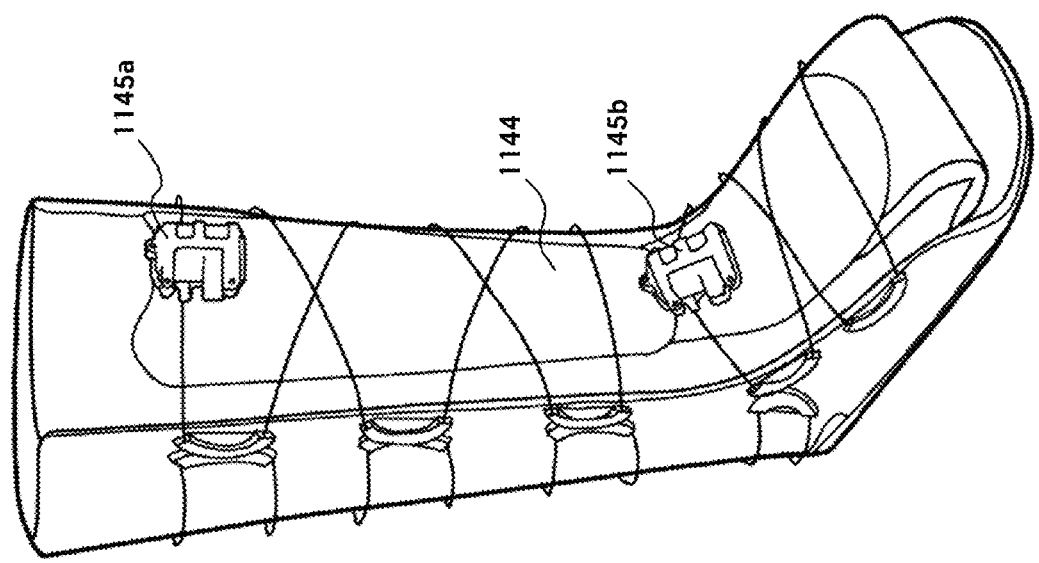

FIGS. 11I and 11J illustrate another embodiment 1140 of a brace 1144. Brace 1144 is similar to the braces described previously in that brace 1144 includes a first motorized closure device 1145a, a second motorized closure device 1145b, and/or other motorized closure devices that may be individually operated to provide zonal tensioning and pressure. Brace 1144 also includes a sensor sock 1142 that is positioned within an interior region of brace 1144 and adjacent the patient's body. Sensor sock 1142 includes a grid of sensors that is used to detect various characteristics of the patient's body, such as the temperature of the body part, blood pressure, pulse rate, and the like. The grid of sensors may also be used to measure localized pressure within the brace 1144 so that pressure points within the brace may be detected and appropriate action performed. For example, if a localized pressure point is detected, information about the pressure point can be transmitted to one or more of the motorized closure devices, or to a computing device or controller that controls the motorized closure device, so that one or more zones of the brace may be loosened to reduce or eliminate the pressure point. Similar actions could occur if high or low temperatures are detected, pooling of blood is detected, and the like, so as to eliminate blisters or other problems from developing.

Figure 11K:
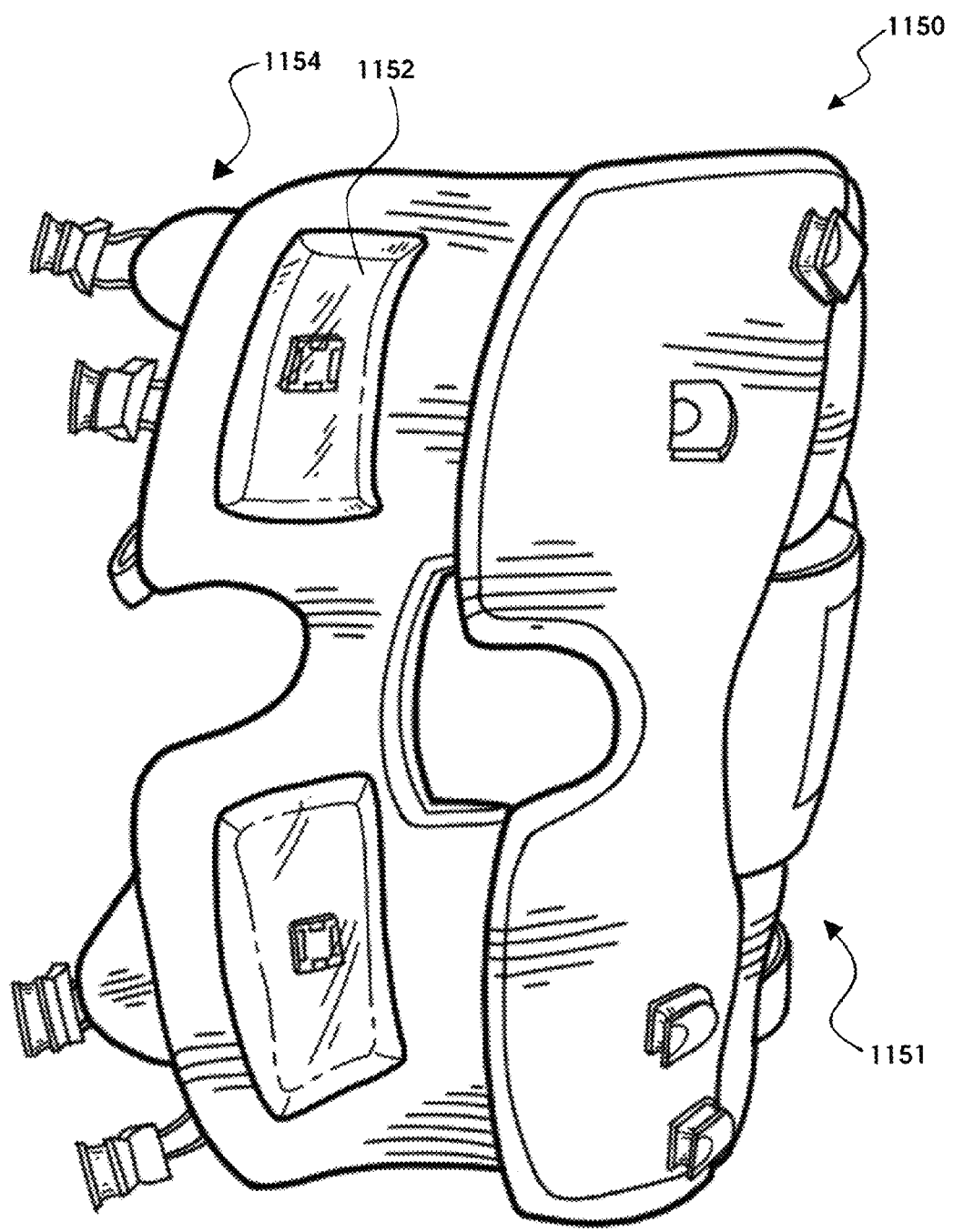

FIG. 11K illustrates another embodiment 1150 of a brace 1151 that may be fit about a patient's body part to provide support and/or for any other reason. Brace 1151 is similar to the other braces described herein in that brace 1151 includes one or more motorized closure devices and may also include straps 1154 that provide macro or gross closure of the brace 1151. Brace 1151 also includes a plurality of sensors 1152 that are used to detect various conditions of the body, such as those described herein. In one embodiment, sensors 1152 include MEMS sensors that are encapsulated in an airtight, gel, or H20 filled bladder or pack. The bladder detects and measure hydrostatic pressure changes that result from the pressure exerted by the brace 1151 on the patient's body and/or from changes in the patient's body, such as swelling, atrophying, and the like. Any measured data may be transmitted to one or more motorized closure devices and/or to a controller of the motorized closure devices so that the pressure applied by the brace can be appropriately adjusted.

In some embodiments, the brace may include one or more motorized closure devices, and preferably two or more such devices, that may be used to provide zonal tensioning of lace to apply zonal pressure to a patient's body part. One or more of the motorized closure devices may be electrically coupled with a sensor device, such as those described above, via one or more electrical connections. The sensor device may include a MEMS sensor or sensors encapsulated in a Gel, H20, or air pack as described herein. The sensor device may measure pressure changes and communicate these changes to the motorized closure device(s). The motorized closure device(s) may use this data to automatically adjust the tension in the lace and the pressure applied by the brace. In some embodiments, the motorized closure device(s) may be attached to an inner layer or material of the brace under a tongue or in some other location so as to be adjacent the patient's skin.

Figure 11L:
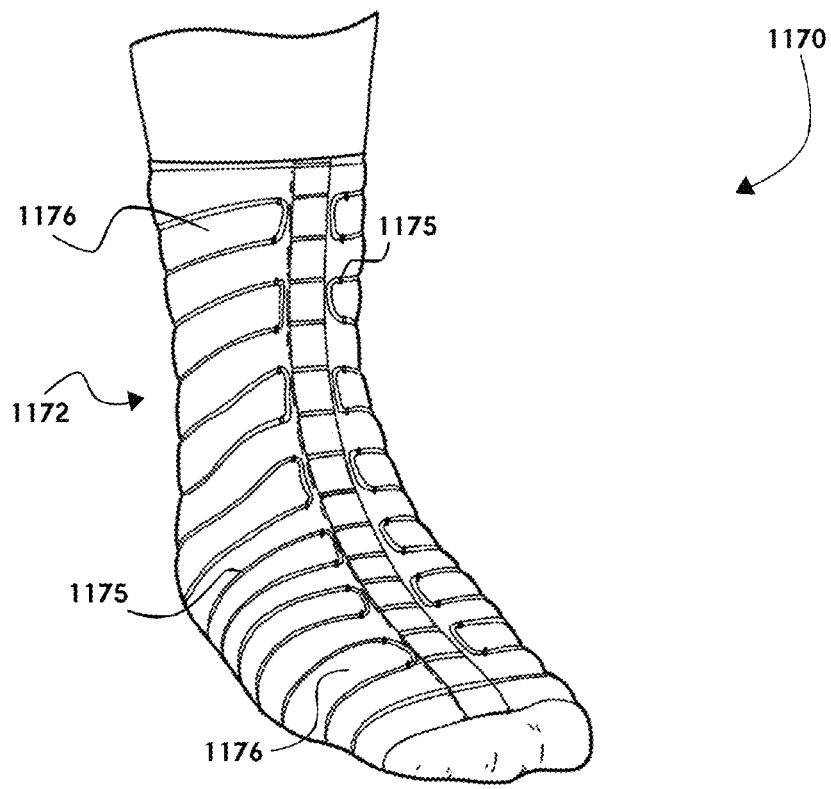
FIGS. 11L and 11M illustrate an embodiment of a sock that may be used to facilitate blood or other bodily fluid flow.
Figure 11M:
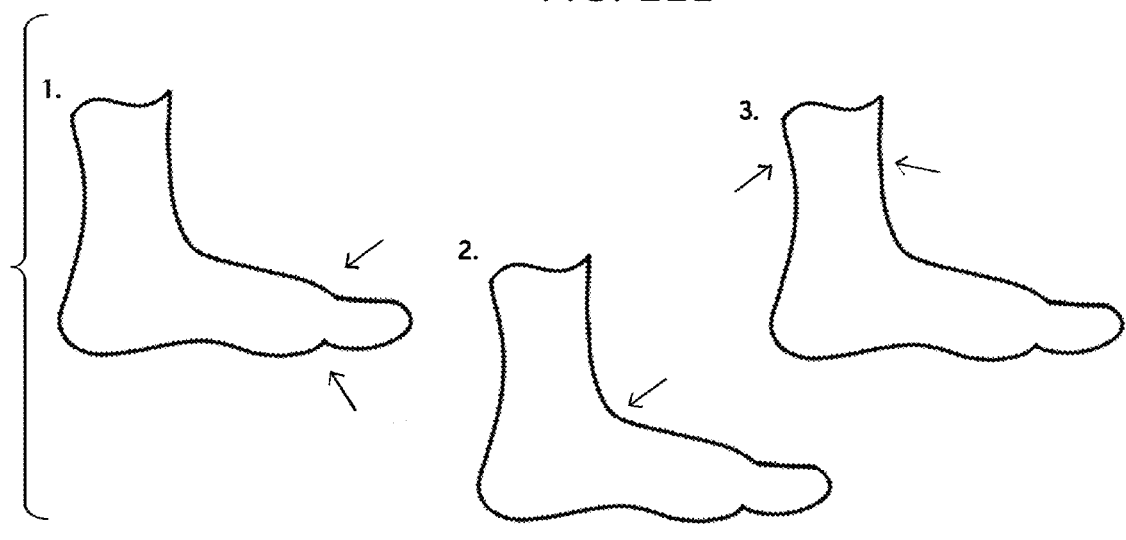

FIGS. 11L and 11M illustrate an embodiment 1170 of a sock 1172 that may be worn by a patient for support and/or for various other reasons, such as to help facilitate blood or other bodily fluid flow to and from a part of the body, such as the foot. In one embodiment, sock 1172 includes a plurality of nitinol wires 1175 that are wrapped circumferentially around the sock 1172 and spaced longitudinally along the sock. As previously described, the nitinol wires may be individually activated electrically to cause the wires to contract and compress the body part. In some embodiments, the wires may be activated in sequence to squeeze the body part (e.g., foot and/or leg) and thereby force blood, or other bodily fluids, to flow to or from the body part. This action of the sock 1172 may help prevent or reduce edema in the body part. The sock 1172 may be worn inside a brace or without a brace.

In some embodiments, the nitinol wires may be attached to strips of material 1176 filled with gel, H20, air, and the like so that actuation of the nitinol wires presses on the strips and the strips press against the patient's skin. In this manner, localized or point pressures that may result from the nitinol wires are minimized or eliminated. In one embodiment, the sock 1172 may include a plurality of such strips 1176 (e.g., 90 strips) spaced longitudinally along the sock. Some or each of the strips 1176 may include an MEMS sensor that may be used to sense conditions of the patient, such as body temperature, localized pressure, blood flow, pulse rate, and the like, as previously described. The MEMS sensors may function as an electrical gate to manage the activation of individual nitinol wires and thereby provide zonal pressure and/or the pumping action described herein. In some embodiments, the individual strips 1176 may be electrically or physically sealed or insulated with respect to adjacent strips so that the strips may be individually electrically actuated and compressed.

In one embodiment, the sock 1172 or a brace may include a power source (not shown) that is used to provide electrical power to the nitinol wires. The MEMS sensor may be electrically coupled with the power source (e.g., battery and the like) so as to manage the activation of individual nitinol wires. In a specific embodiment, an individual MEMS sensor may not be powered until an MEMS sensor directly adjacent the MEMS sensor is powered. This process may result in the sequential triggering of individual strips 1176 and nitinol wires as previously described and may ensure that the sequential triggering essentially always begins at a distal end of the sock 1172 (e.g., positioned near the toes) and proceeds toward a proximal end of the sock (e.g., positioned near the calve or knee) as shown in FIG. 11M. In some embodiments, the MEMS sensors may monitor heart rate and blood or other fluid flow within the body. This data may be transmitted to a local or external controller that may monitor the conditions of the patient and adjust settings of the system as needed. A physician or centralized server may also have access to this data, which may be used for the various reasons described herein.

Figure 12:
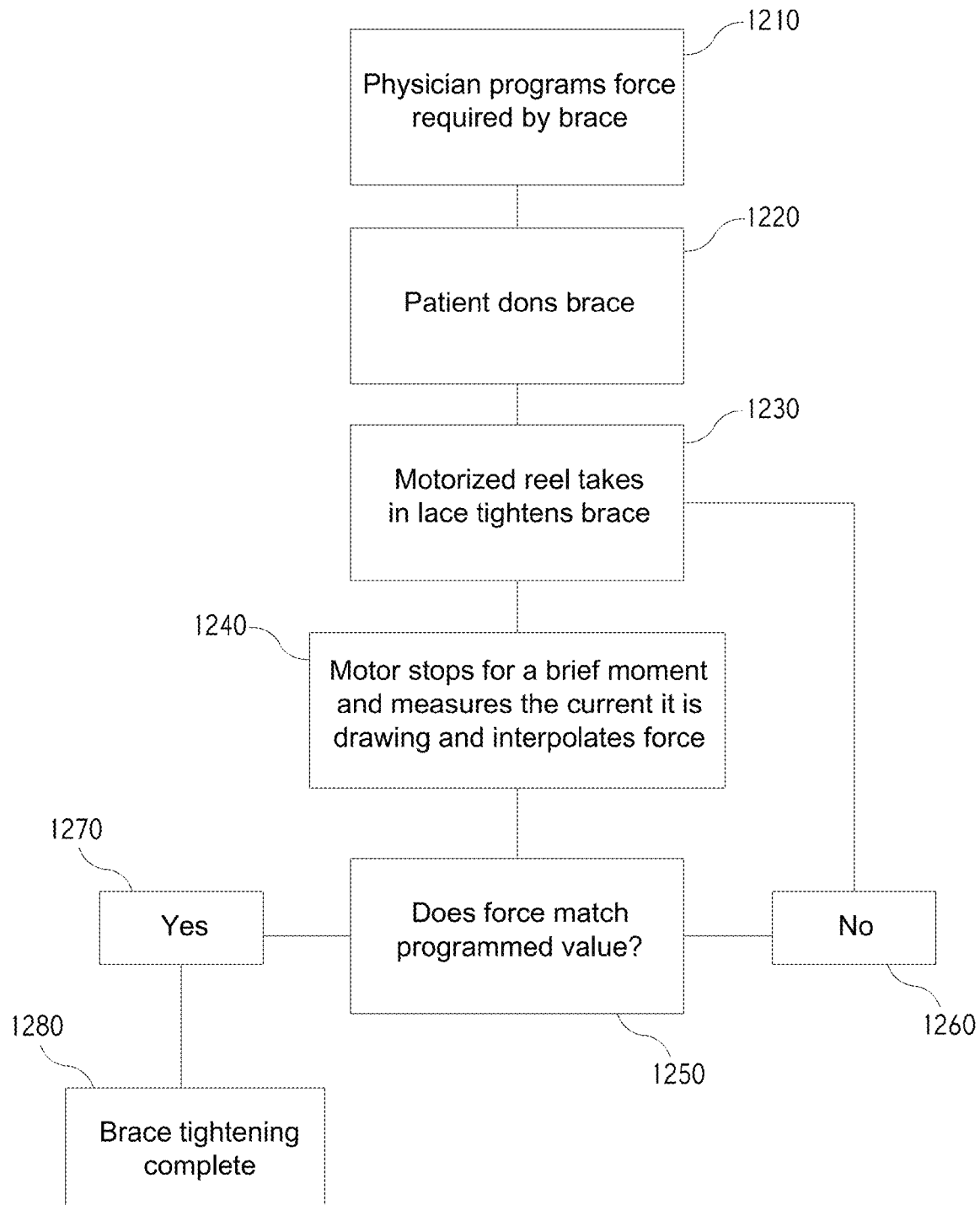
FIG. 12 illustrates a method of adjusting a brace by measuring a current of a motor of a motorized closure device.

FIG. 12 illustrates a method of adjusting a brace by measuring a current of a motor of a motorized closure device. At block 1210, a physician may program or input a force into a controller or other component that is required or desired for the brace. At block 1220, the patient may don the brace. At block 1230, a motorized reel or closure device may take in lace, such as by winding the lace around a spool, to tighten the brace. At block 1240, the motor may briefly stop and measure or calculate the current it is drawing. In some embodiments, the current measurements or calculations may be made in real time without stopping the motor. The measured or calculated current may be interpolated with a force. At block 1250, a determination is made as to whether the force matches the force programmed or input by the physician. At block 1260, if the measured or calculated force does not match the input or programmed force, the process continues to block 1230 and the motor continues to take in lace. At block 1270, if the measured or calculated force does match the input or programmed force, the process continues to block 1280 and brace tightening is complete. This process may be followed each time a user dons the brace and/or when the pressure or lace tension is adjusted by a user and/or by the physician.

Referring now to FIGS. 13A-C, illustrated is an example of a report of a patient's usage of a brace that may be generated based on data collected by the motorized tensioning device and/or a control unit communicatively coupled therewith. As described herein, the data may be transmitted to a central database and the reports of FIGS. 13A-C may be generated at central database. FIG. 13A illustrates a report of an amount of time that a patient wears a brace. The report may be segmented into hours of the day, days of the week, weeks of the month, or any other time period as desired. The report may also be segmented into a night and day usage of the brace. As shown in FIG. 13A, the report may show a number of hours each day and night that the user wears the brace. The report may be coded to illustrate a proper and improper usage of the brace. For example, different colors may show when the brace is worn for an insufficient time and when the brace is worn for sufficient time. In FIG. 13A, the hashed boxes may designate a usage of the brace that is approaching or that exceeds an unacceptable level while the unmarked or clear boxes designate a proper usage of the brace. The dashed boxes may designate days or time periods in which the brace was not worn at all. A physician may quickly analyze the report of FIG. 13A to determine if the patient is properly using the brace.

FIG. 13B illustrates another report that may be generated to show the amount of tension or tightness, or the average tension or tightness, applied while the brace is worn. As with the report FIG. 13A, the report of FIG. 13B may be segmented into a tension level for the day and/or for the night. Hashed boxes (or color-coded boxes) may designate an amount of tension or tightness that is approaching an unacceptably high level while solid colored boxes designate the amount of tension or tightness that is approaching an unacceptably low level. The determination of unacceptably high and/or unacceptably low levels of tightness or tension may be based on a prescribed therapeutic regimen that is designed to promote healing of the limb. A physician may quickly and conveniently review the report FIG. 13B to determine if the brace is being appropriately used to promote healing of the limb.

FIG. 13C illustrates a similar report that may be generated to show an activity level of the patient. The report may be segmented into a high level of activity, a medium level of activity, and a low level of activity. The motorized tensioning device and/or a control unit communicatively coupled therewith may monitor and record various activity levels throughout the day and generate the report FIG. 13C, which a physician can quickly and conveniently review to determine if a patient is engaging in an excessive amount of activity or not engaging in enough activity to promote healing of the limb.

Figure 14A:
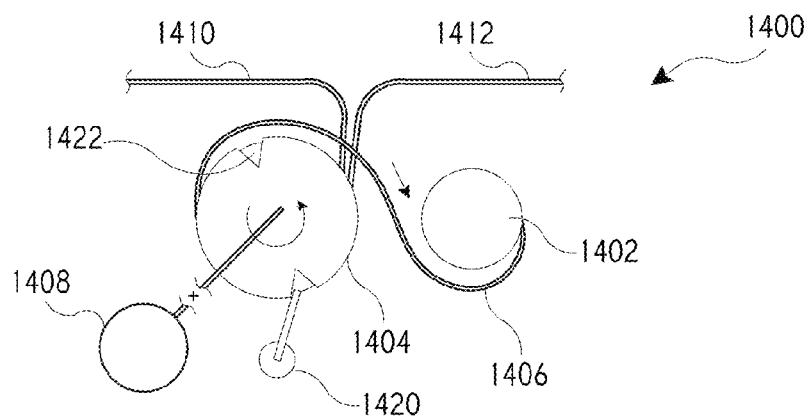
FIGS. 14A-C illustrate an embodiment of a mechanism that may be used with a motorized tensioning device to hold or maintain a brace or other apparel in an open configuration.
Figure 14B:
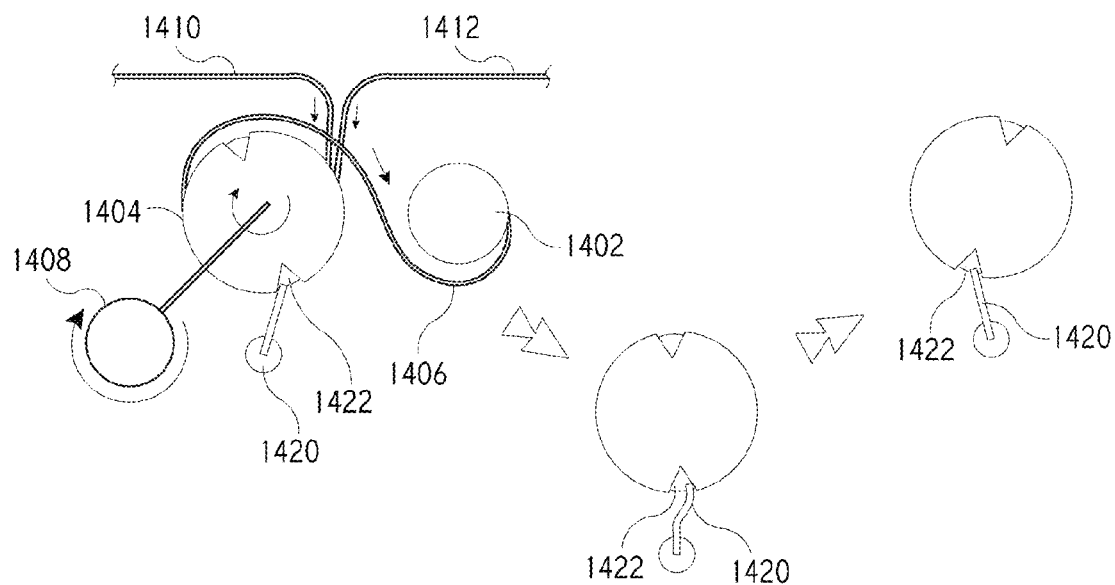
Figure 14C:
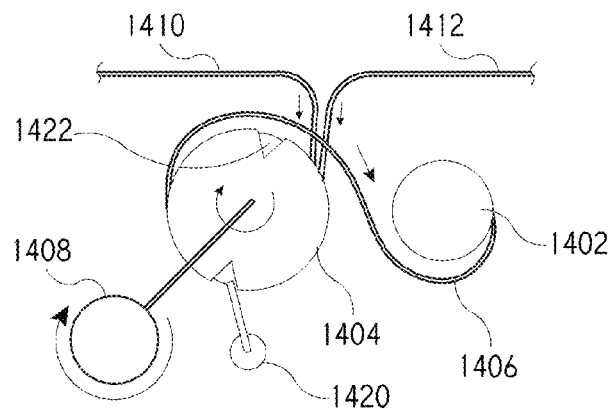

Referring now to FIGS. 14A-C, illustrated is an embodiment of a mechanism that may be used with a motorized tensioning device to hold or maintain a brace or other apparel in an open configuration. The mechanism of FIGS. 14A-C may be particularly useful for secondary winding assemblies of motorized tensioning devices that are used to quickly wind up lace. For example, the mechanism of FIGS. 14A-C may be particularly useful for the secondary winding assembly 260, and in particular spring member 262, of FIG. 1B. In addition to brace applications, the mechanism may find particular usefulness in shoes where a user desires to open opposing eyestays of the shoe and maintain the eyestays in an open configuration until the shoe is fit about the user's foot.

As shown in FIG. 14A, the mechanism 1400 includes a pawl 1420 or other member that is configured to catch and mechanically locked within a detent 1422 or recess of a spool 1404, such as the spool shown in FIG. 1B. The spool 1404 is coupled with a constant force spring 1402 via a spring component 1406. The constant force spring 1402 is configured to rapidly wind the spool 1404 via the spring component 1406 as described in FIG. 1B. To prevent automatic winding of the spool 1404 via constant force spring 1402, pawl 1420 engages with detent 1422 and locks or maintains spool 1404 in position. This allows a first lace 1410 and/or second lace 1412 and to remain relatively loose and/or un-tensioned, which aides in donning of the brace or other apparel (e.g., shoe). FIG. 14A shows the pawl 1420 being positioned in a rightward orientation relative to spool 1404 and within detent 1422 to prevent clockwise rotation of spool 1404 and thereby hold or maintain the spool 1404 in position. The rotational force exerted on spool 1404 via constant force spring 1402 and spring component 1406 is not sufficient to overcome the force imparted on spool 1404 by pawl 1420. Stated differently, pawl 1420 counteracts rotation of spool 1404. As such, the spool 1404 remains stationary while the pawl 1420 is positioned in the rightward orientation.

After the brace or shoe is donned and the user wishes to close and tighten the brace or shoe, the motor 1408 may be actuated to move the pawl 1420 into a disengaged position relative to spool 1404 and detent 1422. Specifically, as shown in FIG. 14B, the motor 1408 may be engaged to rotate spool 1404 clockwise. The force of the motor 1408 is sufficient to cause the pawl 1420 to buckle within detent 1422 or otherwise move relative thereto. As shown in FIG. 14B, buckling or moving of the pawl 1420 causes the pawl 1422 shift from the rightward orientation to a leftward orientation in which the pawl 1420 does not prevent clockwise rotation of spool 1404. Rather, in the leftward orientation, the detent 1422 may cause the pawl 1420 to deflect as the spool 1404 is rotated clockwise. Movement of the pawl 1420 from the rightward orientation to the leftward orientation allows the constant force spring 1402 to quickly wind spool 1404 clockwise via spring component 1406, which allows the first lace 1410 and/or second lace 1412 to be quickly wound around the spool 1404. Further tensioning of the first lace 1410 and/or second lace 1412 may be achieved via motor 1408 as described in FIG. 1B.

FIG. 14C illustrates the pawl 1420 in the leftward orientation relative to spool 1404. FIG. 14C also illustrates the pawl 1420 being positioned within one of the detents 1422 in the leftward orientation. Positioning of the pawl 1420 within one of the detents 1422 may aid in preventing counter rotation of the spool 1404 (e.g., counterclockwise rotation of spool 1404). To unwind or loosen the first lace 1410 and/or second lace 1412, the reverse of the above process may be performed. Specifically, motor 1408 may be actuated to cause spool 1404 to rotate in a counterclockwise direction, which causes pawl 1420 to buckle or move from the leftward orientation to the rightward orientation shown in FIG. 14A. The first lace 1410 and/or second lace 1412 may then be loosened via motor 1408 or via pulling open the brace or shoe. Pawl 1420 then functions to maintain the brace or shoe in an open configuration as described above.

Figure 15:
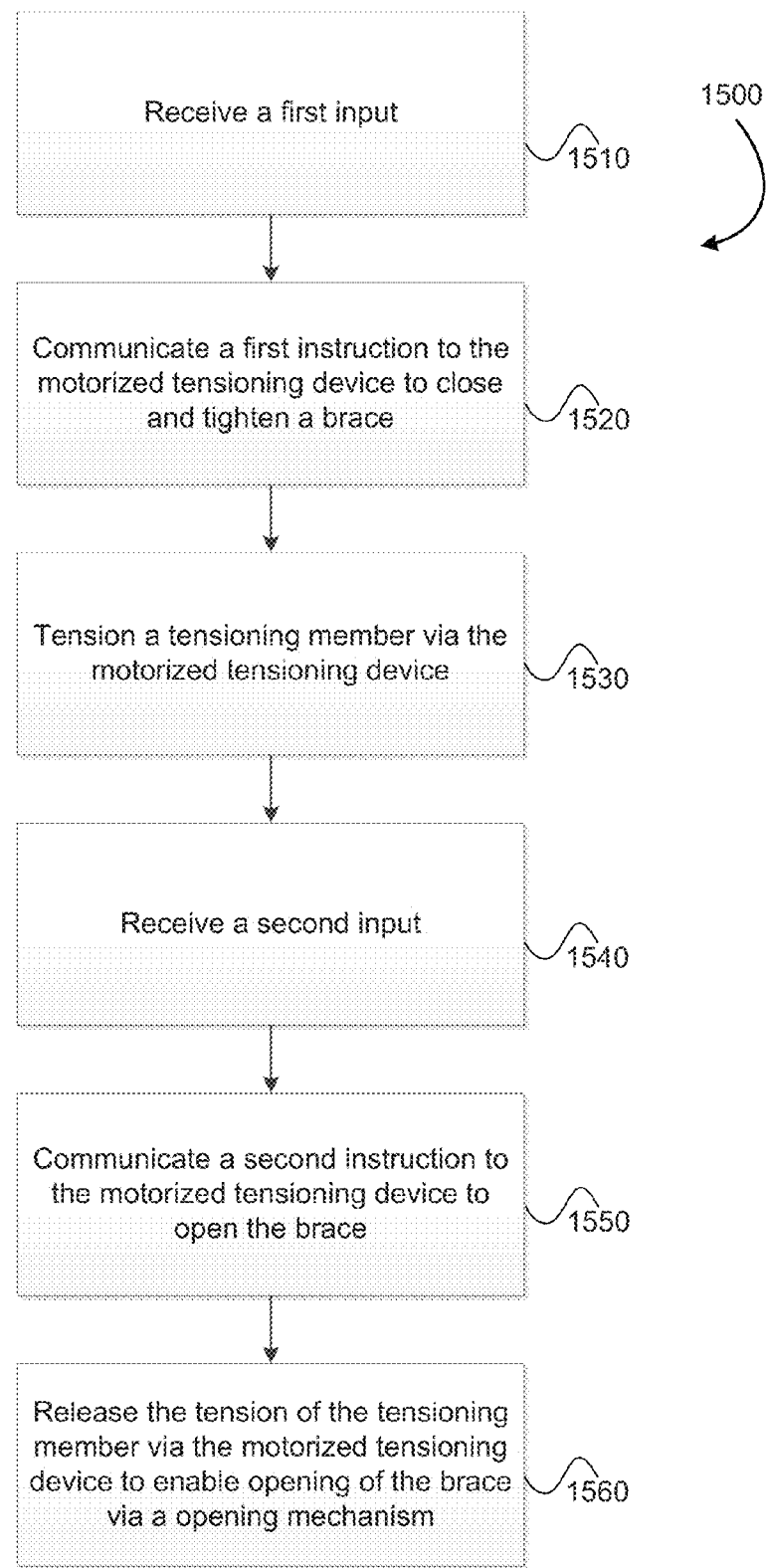
FIG. 15 illustrates a method for automatically opening and closing a brace about a limb.

Referring now to FIG. 15, illustrated is a method 1500 for automatically opening and closing a brace about a limb. The method is achieved via brace having an opening mechanism such as those described in FIGS. 9A-H. The brace may be in an initially open configuration to allow a user to easily don the brace. As described herein the brace may include a motorized tensioning device, a control unit communicatively coupled with the motorized tensioning device, and an opening mechanism that opens the brace as the tension of the tensioning member tension is reduced. The motorized tensioning device and control unit may be configured to adjust a tension of a tensioning member of the brace to close and tighten the brace about a limb or to allow the brace to be opened and removed from the limb. According to the method, at block 1510 a first input is received via the control unit. The first input may be received in response to a user selecting a button or other actuation control, may be a preconfigured value stored in a memory device of the control unit, or may be automatically generated by the control unit in response to a therapeutic regimen, prescribed parameter, or a detection of the user donning the brace.

At block 1520, a first instruction is communicated from the control unit to the motorized tensioning device. The first instruction may include a tension value for the tensioning member that is input by a user, automatically generated by the control unit, provided by a physician, and the like. The first instruction may be communicated via a wired or wireless transmission as described herein above. At block 1530, the tensioning member is tensioned to substantially the tension value via the motorized tensioning device to close and tighten the brace about the limb. Tensioning the tension member to substantially the tension value implies that the tension member's tension is at or near the tension value, but not necessarily exactly equal to the tension value. For example, as known in the art, small deviations from a value may be acceptable for balancing the operation time of the motorized tensioning device while achieving a desired outcome. In some embodiments, the tension member may be tensioned to within ±0.5 pounds of the tension value since a deviation of the tightness of the brace within this range is typically unnoticeable to a user.

At block 1540, a second input is received via the control unit. At block 1550, a second instruction is communicated from the control unit to the motorized tensioning device. The second instruction may be communicated via a wireless or wired transmission as described herein above. At block 1560, the tension of the tensioning member is reduced via the motorized tensioning device to loosen the brace about the limb and to enable automatic opening of the brace via the opening mechanism. Automatic opening of the brace via the opening mechanism aids in doffing of the brace. The automatic opening and closing of the brace as described in FIG. 15 enables dexterity challenged individuals to easily don and doff and tighten and loosen a brace about a limb.

In reducing the tension member's tension, the motorized tensioning device may reduce the tension until a specified tension is achieved, may reduce the tension for a specified period of time, and/or may reduce the tension until a limit switch is contacted. A timed reduction in a tension member's tension may be useful when the goal is to merely lower the tension value, such as for relief. Reduction in tension to a specified value may be useful when a controlled output is desired, such as achieving a minimum tension (i.e., allowing tension adjustment within a specified range). Reducing tension until a limit switch is contacted may be useful in instances where tension is released until the occurrence of an event, such as releasing of a Weston clutch or other component within the motorized tensioning device is achieved.

In some embodiments, the tensioning member is a first lace that is guided by one or more guides positioned on the brace. The first lace may be configured to tighten the brace about the limb upon tensioning of the first lace. In such embodiments, the brace may further include a second lace that is operably coupled with the opening mechanism and with the motorized tensioning device. The motorized tensioning device may tension the second lace as the tension of the first lace is reduced. Tensioning of the second lace may effect opening of the brace via the opening mechanism. In other embodiments, the opening mechanism may include a spring mechanism that is coupled with the brace so as to effect opening of the brace as the tensioning member's tension is reduced.

In some embodiments, the first input and/or the second input may be received from a user. In another embodiment, the first input may be automatically generated based on input from a sensor corresponding to the brace being positioned about the limb. In some embodiments, the second input may be automatically generated based on input from a sensor corresponding to a dangerous condition associated with the brace. The dangerous condition that is detected may include a relatively high lace tension, high temperature within the brace, the formation of one or more boils, and the like.

In donning and doffing of the brace, the limb may be inserted within the brace along an axis. In such embodiments, opening of the brace may include increasing a cross sectional area of the brace about a plane orthogonal to the axis by between 25% and 50%. For example, as shown in FIG. 9B, a user may insert a limb (e.g., wrist) along an axis A. In opening of the brace, a cross sectional area of the brace about plane B, that is orthogonal to axis A, may be opened by between about 25% and 50% to allow the user to quickly and easily doff the brace. In other embodiments, the cross sectional area of the brace about plane B may be opened by between about 30% and 40%.

In some embodiments, a brace having a motorized tensioning device, a tensioning member operationally coupled with the motorized tensioning device to tighten the brace about a limb, and a control unit communicatively coupled with the motorized tensioning device to control adjustment of a tension of the tensioning member may be configured to perform the method illustrated in FIG. 15. Specifically, the control unit may be configured to perform some or all of the operations of FIG. 15 to close and tighten a brace about a limb and open the brace therefrom. An opening mechanism of the brace may be configured to automatically open the brace as the tension of the tensioning member tension is reduced and the brace is loosened.

Figure 16:
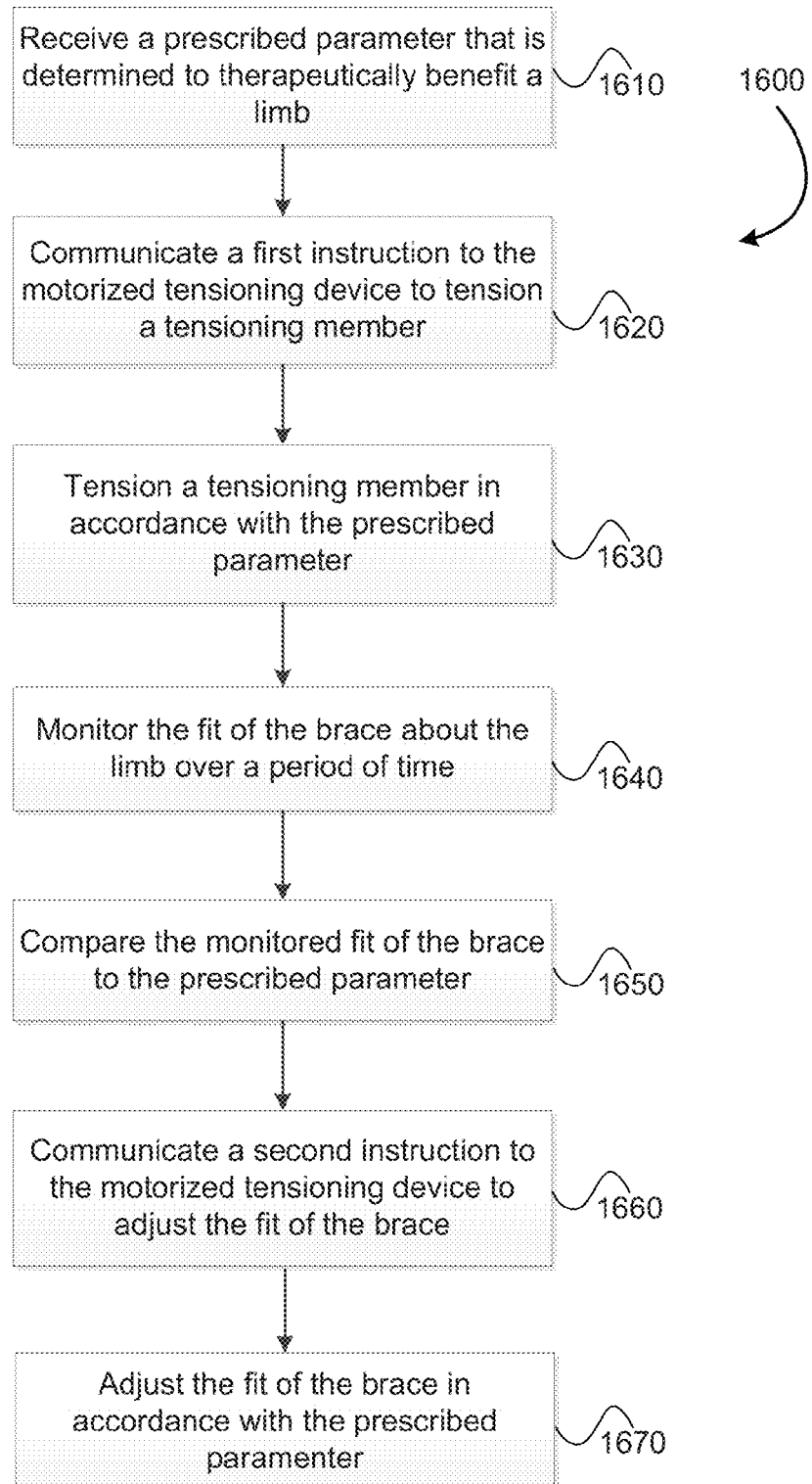
FIG. 16 illustrates a method for tightening a brace about a limb.

Referring now to FIG. 16, illustrated is a method 1600 for tightening a brace about a limb. As described herein, the brace includes a motorized tensioning device and a control unit communicatively coupled with the motorized tensioning device. The motorized tensioning device and control unit are configured to adjust a tension of a tensioning member of the brace to tighten the brace about the limb. According to the method, at block 1610 a prescribed parameter is received at the control unit for the brace. The prescribed parameter is a parameter that is determined to therapeutically benefit the limb, such as a prescribed tension of the tensioning member or a tightness and/or pressure to be exerted on the limb by the brace. The prescribed parameter may be input by a physician or maybe automatically generated based on a therapeutic regimen that is designed for healing of the limb by a physician or other professional. In some embodiments, a physician may fit the brace of the limb to tension the brace until the desired tightness or pressure is achieved. The physician may use their fingers or another device to measure the tightness or pressure of the brace. The physician may then record the lace tension and use the lace tension as the prescribed parameter or may select a button that automatically measures the lace tension and uses this tension as the prescribed parameter.

At block 1620, a first instruction is communicated from the control unit to the motorized tensioning device to tension the tensioning member to a tension value that is determined from the prescribed parameter. At block 1630, the tensioning member is tensioned via the motorized tensioning device to substantially the tension value to adjust a fit of the brace about the limb in accordance with the prescribed parameter. As described previously, the tensioning member may be tensioned to the tension value accounting for some common or accepted deviation from the exact tension value. At block 1640, the fit of the brace about the limb is monitored via the control unit over a period of time, which may be measured in terms of seconds, minutes, hours, multiple hours, days, and the like. At block 1650, the monitored fit of the brace is compared to the prescribed parameter to determine that the fit of the brace exceeds a variance threshold for the fit. At block 1660, a second instruction is communicated from the control unit to the motorized tensioning device to adjust the fit of the brace about the limb. At block 1670, the tension of the tensioning member is adjusted via the motorized tensioning device so that the fit of the brace about the limb is in accordance with the prescribed parameter.

In the above manner, the fit of the brace about the limb is always in accordance with a prescribed parameter that therapeutically benefits the limb. For example, a pressure or tightness of the brace is maintained at a value that is designed to promote healing of the limb. The brace may need to automatically adjust to maintain a desired pressure or tightness of the brace due to swelling or other conditions of the limb. For example, limbs often swell or contract due to water retention, dehydration, inflammation, swelling, atrophy, and the like, which affect the tightness or pressure that is exerted on the limb from a brace. Conventional braces are unable to adjust to such conditions and thus are may be unable to maintain a tightness or pressure that facilitates in improved healing.

In some embodiments, the prescribed parameter includes the tension value for the tensioning member (e.g., includes a tension value for the lace of the motorized tensioning device). In some embodiments, the step of monitoring the fit of the brace may include monitoring the tension of the tensioning member (e.g., lace) over the period of time and the step of comparing the monitored fit of the brace may include comparing the tension of the tension member to the tension value to determine that the tension exceeds a tension threshold. In some embodiments, the prescribed parameter may also include a duration of tensioning for the tensioning member, which may be measured in terms of minutes, hours, days, weeks, and the like. The prescribed tension parameter may further include an acceptable variation of the tension over the period of time. In some embodiments, the prescribed parameter may include a tension range that defines an upper tension value and a lower tension value within which a user may adjust the tensioning member's tension.

In other embodiments, the prescribed parameter may include a prescribed pressure or tightness of the brace about the limb. In such embodiments the method may further include determining the tension value for the tensioning member based on the pressure of the brace about the limb. In such embodiments, determining the tension value for the tensioning member may include tensioning the tensioning member via the motorized tensioning device until a pressure or tightness of the brace achieves the prescribed pressure. In other embodiments, determining the tension value for the tensioning member may include calculating a value that corresponds to the prescribed brace pressure or tightness. For example, a lace tension that corresponds to the prescribed brace tightness or pressure may be calculated by the control unit and transmitted to the motorized tensioning device to tighten the brace to the prescribed parameter.

In some embodiments, monitoring the fit of the brace may include monitoring the tension of the tensioning member over the period of time and the method may further include: transmitting data corresponding to the monitored tension to an external computing device and determining via the transmitted data one or more of the following: that the user is wearing the brace for a prescribed duration, that the tension of the tension member complies with the prescribed tension parameter, and/or a level of healing of the limb. In some embodiments, the method may additionally include receiving data at a central database regarding the fit of a plurality of braces about corresponding limbs and the therapeutic effects of the usage of the braces and determining a recommended brace usage based on the therapeutic effects.

In some embodiments, the prescribed parameter may be a parameter that is identified from a recommended brace usage. The recommended brace usage may be determined from data that is analyzed at a central database regarding the fit of a plurality of braces about corresponding limbs and the therapeutic effects of the usage of the braces. Stated differently, information about the fit of braces (e.g., pressure, stiffness, tightness, and the like of the brace) and the effectiveness of the fit in promoting healing and/or recovery of a limb may be collected and used to determine effective therapies for future use in fitting braces about the limbs. The prescribed parameter that is input into the brace may be based on an effective therapy that is developed from collected and analyzed data. Charts, graphs, or other information providing documents may be used to disseminate information on the effective therapies that are developed from such data collection and analysis. Charts or graphs may be provided to doctors or physicians for use in prescribing parameters that are determined to promote healing of the limb as described in FIG. 16.

Figure 17:
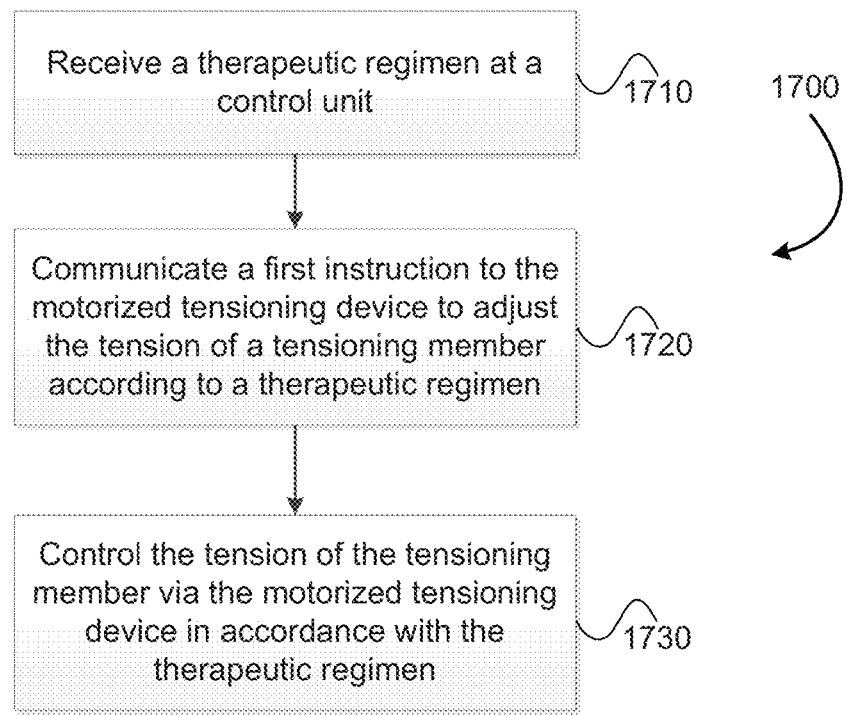
FIG. 17 illustrates a method for providing therapy with a brace fitted about a limb.

Referring now to FIG. 17, illustrated is a method 1700 for providing therapy with a brace fitted about a limb. As described herein the brace includes a motorized tensioning device, a tensioning member that is operationally coupled with the motorized tensioning device to tighten the brace about the limb, and a control unit communicatively coupled with the motorized tensioning device to control adjustment of a tension of the tensioning member. According to the method, at block 1710 a therapeutic regimen is received at the control unit. The therapeutic regimen may be a therapy that is prescribed by a physician to promote healing of the limb and/or to prevent weakening of the limb being supported by the brace. The therapeutic regimen may be designed to aid in recovery of the limb via repetitive movement of the limb. For example, the brace may be used to prevent atrophy of the limb, to increase muscle strength, and/or to increase a range of motion of the limb such as after surgery and/or ligament or tendon damage. Step 1710 is an optional step that does not need to be included in every embodiment. For example, in some embodiments the control unit may monitor the activity of the brace and formulate or otherwise devise a therapeutic regimen that will promote healing of the limb. In some embodiments, receiving the therapeutic regimen may include preprogramming the control unit to include the therapeutic regimen or may include receiving the therapeutic regimen via a wired or wireless transmission after the user has donned and tightened the brace.

At block 1720, a first instruction is communicated from the control unit to the motorized tensioning device to adjust the tension of the tensioning member in accordance with the therapeutic regimen. The first instruction may instruct the motorized tensioning device to repetitively or cyclically adjusted the tension of the tensioning member to promote repetitive movement of the limb. At block 1730, the tension of the tensioning member is controlled via the motorized tensioning device in accordance with the therapeutic regimen to enable flexing of the brace and thereby promote repetitive movement and therapeutic healing of the limb. In some embodiments, controlling the tensioning the tension member may include providing a desired resistance via the motorized tensioning device in response to the user flexing the brace via flexing of the limb or repetitively or cyclically increasing and decreasing the tension of the tensioning member to effect repetitive or cyclical movement of the brace and limb.

In some embodiments, the method may further include alerting the user that the user's flexing of the brace via flexing of the limb is not in compliance with the therapeutic regimen. In other embodiments, the method may further include alerting the user to perform the therapeutic regimen. Alerting the user may include an audible or visual signal that indicates the compliance or noncompliance with the therapeutic regimen. In some embodiments, the user may flex a limb until an audible and/or visual signal is provided to the user to indicate compliance with the therapeutic regimen. In some embodiments, the resistance provided by the motorized tensioning device may be increased over time in accordance with the therapeutic regimen, or the cyclical or repetitive increasing and decreasing of the tensioning member's tension may be increased over time in accordance with the therapeutic regimen. In some embodiments, the method may additionally include transmitting data regarding the therapeutic regimen to an external database. In some embodiments, the method may additionally include displaying information related to the therapeutic regimen on a user interface of the brace.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method for automatically opening and closing an article about a body part, the method comprising:
   an article in an initially open configuration that aids in donning of the article, the article including:
   a motorized tensioning device;
   a control unit communicatively coupled with the motorized tensioning device, the motorized tensioning device and control unit being configured to adjust a tension of a tensioning member of the article; and
   an opening mechanism that opens the article as the tension of the tensioning member tension is reduced;
   receiving a first input at the control unit;
   communicating a first instruction from the control unit to the motorized tensioning device, wherein the first instruction comprises a tension value that is provided by a user or that is a preconfigured value stored in a memory device of the control unit;
   in response to the first instruction, tensioning the tensioning member via the motorized tensioning device so as to close and tighten the article about the body part;
   receiving a second input via the control unit;
   communicating a second instruction from the control unit to the motorized tensioning device; and
   in response to the second instruction, reducing the tension of the tensioning member via the motorized tensioning device so as to loosen the article about the body part and to enable opening of the article via the opening mechanism to aid in doffing of the article.

2. The method of claim 1, wherein the tensioning member is a first lace that is guided by one or more guides positioned on the article, the first lace being configured to tighten the article about the body part upon tensioning of the first lace, and wherein the article further includes a second lace that is operably coupled with the opening mechanism and with the motorized tensioning device, wherein the motorized tensioning device tensions the second lace as the tension in the first lace is reduced, and wherein tensioning of the second lace effects opening of the article via the opening mechanism.

3. The method of claim 1, wherein the opening mechanism includes a spring mechanism that is coupled with the article so as to effect opening of the article as the tensioning member's tension is reduced.

4. The method of claim 1, wherein either or both the first input or the second input is received from a user.

5. The method of claim 1, wherein the first input is automatically generated based on input from a sensor corresponding to the article being positioned about the body part.

6. The method of claim 1, wherein the second input is automatically generated based on input from a sensor corresponding to a dangerous condition associated with the article.

7. The method of claim 1, wherein in donning and doffing of the article, the body part is inserted within the article along an axis, and wherein opening of the article includes increasing a cross sectional area of the article about a plane orthogonal to the axis by between 25% and 50%.

8. An article comprising:
   a motorized tensioning device;
   a tensioning member operationally coupled with the motorized tensioning device to tighten the article about a body part;
   a control unit communicatively coupled with the motorized tensioning device to control adjustment of a tension of the tensioning member, wherein the control unit is configured to:
   receive a first input;
   communicate a first instruction to the motorized tensioning device to tension the tensioning member and thereby close and tighten the article about the body part;
   receive a second input; and
   communicate a second instruction to the motorized tensioning device to reduce the tension of the tensioning member and thereby loosen the article about the body part; and
   an opening mechanism configured to automatically open the article as the tension of the tensioning member tension is reduced and the article is loosened;
   wherein the opening mechanism includes a spring mechanism that is coupled with the article so as to effect opening of the article as the tensioning member's tension is reduced.

9. The article of claim 8, wherein the tensioning member is a first lace that is guided by one or more guides positioned on the article, the first lace being configured to tighten the article about the body part upon tensioning of the first lace, and wherein the article further includes a second lace that is operably coupled with the opening mechanism and with the motorized tensioning device, wherein the motorized tensioning device tensions the second lace as the tension in the first lace is reduced, and wherein tensioning of the second lace effects opening of the article via the opening mechanism.

10. The article of claim 8, wherein either or both the first input or the second input is received from a user.

11. The article of claim 8, wherein the article further comprises a sensor that is configured to sense when the article is positioned about the body part, the sensor being communicatively coupled with the control unit such that the first input is automatically generated based on input from the sensor of the article being positioned about the body part.

12. The article of claim 8, wherein the control unit is further configured to automatically generate the second input based on information from a sensor of a dangerous condition associated with the article.

13. The article of claim 8, wherein in donning and doffing of the article, the body part is inserted within the article along an axis, and wherein opening of the article includes increasing a cross sectional area of the article about a plane orthogonal to the axis by between 25% and 50%.

14. A method for tightening a brace about a limb comprising:
a brace including:
a motorized tensioning device; and
a control unit communicatively coupled with the motorized tensioning device, the motorized tensioning device and control unit being configured to adjust a tension of a tensioning member of the brace to tighten the brace about the limb;
receiving, at the control unit, a prescribed parameter for the brace that is determined to therapeutically benefit the limb;
communicating a first instruction from the control unit to the motorized tensioning device to tension the tensioning member to a tension value determined from the prescribed parameter;
tensioning, via the motorized tensioning device, the tensioning member to substantially the tension value so as to adjust a fit of the brace about the limb in accordance with the prescribed parameter;
monitoring, via the control unit, the fit of the brace about the limb over a period of time;
comparing the monitored fit of the brace to the prescribed parameter to determine that the fit of the brace exceeds a variance threshold for the fit;
communicating a second instruction from the control unit to the motorized tensioning device to adjust the fit of the brace about the limb; and
adjusting the tension of the tensioning member via the motorized tensioning device so that the fit of the brace about the limb is in accordance with the prescribed parameter.

15. The method of claim 14, wherein the prescribed parameter includes the tension value for the tensioning member.

16. The method of claim 14, wherein monitoring the fit of the brace comprises monitoring the tension of the tensioning member over the period of time; and comparing the monitored fit of the brace comprises comparing the tension of the tension member to the tension value to determine that the tension exceeds a tension threshold.

17. The method of claim 14, wherein the prescribed parameter further comprises a duration of tensioning for the tensioning member.

18. The method of claim 14, wherein the prescribed tension parameter further comprises a variation of the tension over the period of time.

19. The method of claim 14, wherein the prescribed tension parameter further comprises a tension range that defines an upper tension value and a lower tension value within which a user may adjust the tensioning member's tension.

20. The method of claim 14, wherein the prescribed parameter includes a prescribed pressure of the brace about the limb, and wherein the method further comprises:
determining the tension value for the tensioning member based on the pressure of the brace about the limb.

21. The method of claim 20, wherein determining the tension value for the tensioning member includes tensioning the tensioning member via the motorized tensioning device until a pressure of the brace achieves the prescribed pressure.

22. The method of claim 20, wherein determining the tension value for the tensioning member includes calculating a value that corresponds to the prescribed pressure.

23. The method of claim 14, wherein monitoring the fit of the brace comprises monitoring the tension of the tensioning member over the period of time, and wherein the method further comprises:
transmitting data corresponding to the monitored tension to an external computing device; and
determining via the transmitted data one or more of the following:
that the user is wearing the brace for a prescribed duration;
that the tension of the tension member complies with the prescribed tension parameter; or
a level of healing of the limb.

24. The method of claim 14, further comprising:
receiving data at a central database regarding the fit of a plurality of braces about corresponding limbs and therapeutic effects of the usage of the braces; and
determining a recommended brace usage based on the therapeutic effects.

25. The method of claim 14, wherein the prescribed parameter is a parameter identified from a recommended brace usage, the recommended brace usage being determined from data analyzed at a central database regarding the fit of a plurality of braces about corresponding limbs and therapeutic effects of the usage of the braces.

* * * * *